United States Patent
Mengeling et al.

(10) Patent No.: US 6,641,819 B2
(45) Date of Patent: Nov. 4, 2003

(54) PORCINE REPRODUCTIVE AND RESPIRATORY SYNDROME VACCINE, BASED ON ISOLATE JA-142

(75) Inventors: William L. Mengeling, Ames, IA (US); Ann Vorwald, Ames, IA (US); Kelly Lager, Neveda, IA (US); Kelly Burkhart, Radcliffe, IA (US); David E. Gorcyca, St. Joseph, MO (US); Mike Roof, Ames, IA (US)

(73) Assignees: USDA, Peoria, IL (US); Boehringer Ingelheim Corp., Ridgefield, CT (US)

( * ) Notice: Subject to any disclaimer, the term of this patent is extended or adjusted under 35 U.S.C. 154(b) by 0 days.

(21) Appl. No.: 09/981,282

(22) Filed: Oct. 18, 2001

(65) Prior Publication Data

US 2003/0119170 A1 Jun. 26, 2003

Related U.S. Application Data

(63) Continuation-in-part of application No. 09/461,879, filed on Dec. 15, 1999, now abandoned, which is a continuation-in-part of application No. 09/298,110, filed on Apr. 22, 1999, now abandoned.

(51) Int. Cl.[7] .......................... A61K 39/12; C12P 21/06
(52) U.S. Cl. ............... 424/204.1; 424/184.1; 424/815; 435/69.1; 435/6; 435/235.1
(58) Field of Search .................. 424/204.1, 184.1, 424/815, 218.1; 435/6, 69.1, 5, 235.1

(56) References Cited

U.S. PATENT DOCUMENTS

| | | | |
|---|---|---|---|
| 4,554,159 A | * | 11/1985 | Roizman et al. ......... 424/205.1 |
| 5,476,778 A | | 12/1995 | Chladek et al. |
| 5,510,258 A | | 4/1996 | Sanderson et al. |
| 5,587,164 A | | 12/1996 | Sanderson et al. |
| 5,698,203 A | * | 12/1997 | Visser et al. ............. 424/218.1 |
| 5,840,563 A | | 11/1998 | Chladek et al. |
| 5,846,805 A | | 12/1998 | Collins et al. |

FOREIGN PATENT DOCUMENTS

| | | |
|---|---|---|
| EP | 0595436 | 5/1994 |
| EP | 0676467 A2 * | 4/1995 |
| WO | 9303760 | 3/1993 |
| WO | 9418311 | 8/1994 |

OTHER PUBLICATIONS

Wesley et al, in Proceedings. Annul Meet Am Assoc Swine Pract, 1996; 27:141–143.*

Andreyev, et al.; Genetic variation and phylogenetic relationships of 22 porcine reproductive and respiratory syndrome virus (PRRSV) field strains based on sequence analysis of open reading frame 5; Arch Virol (1997) 142: 993–1001.

* cited by examiner

*Primary Examiner*—Ali R. Salimi
(74) *Attorney, Agent, or Firm*—Hovey Williams LLP

(57) ABSTRACT

Substantially avirulent forms of atypical porcine reproductive and respiratory syndrome (PRRS) virus and corresponding vaccines are provided which result from cell culture passaging of virulent forms of PRRS. The resultant avirulent atypical PRRS virus is useful as a vaccine in that PRRS specific antibody response is elicited by inoculation of host animals, thereby conferring effective immunity against both previously known strains of PRRS virus and newly isolated atypical PRRS virus strains. The preferred passaging technique ensures that the virus remains in a logarithmic growth phase substantially throughout the process, which minimizes the time required to achieve attenuation. The present invention also provides diagnostic testing methods which can differentiate between animals infected with field strains and attenuated strains of PRRSV.

6 Claims, 2 Drawing Sheets

US 6,641,819 B2

PORCINE REPRODUCTIVE AND RESPIRATORY SYNDROME VACCINE, BASED ON ISOLATE JA-142

RELATED APPLICATION

This is a continuation-in-part of application Ser. No. 09/461,879 filed Dec. 15, 1999 now abandoned, which is a continuation-in-part of application Ser. No. 09/298,110 filed Apr. 22, 1999 now abandoned.

SEQUENCE DISCLOSURE

A paper copy of the "Sequence Listing" is enclosed herein and is hereby incorporated by reference.

BACKGROUND OF THE INVENTION

1. Field of the Invention

The present invention is broadly concerned with attenuated avirulent atypical porcine reproductive and respiratory syndrome (PRRS) virus (PRRSV), and corresponding live virus vaccines for administration to swine in order to confer effective immunity in the swine against PRRSV. The invention also includes methods of immunizing swine against PRRSV, and a new, highly efficient method of passaging viruses to attenuation. Furthermore, the invention provides methods of detecting and differentiating between field strains and an attenuated strain of PRRSV.

2. Description of the Prior Art

PRRS emerged in the late 1980's as an important viral disease of swine. PRRSV causes severe reproductive failure in pregnant sows, manifested in the form of premature farrowings, increased numbers of stillborn, mummified and weak-born pigs, decreased farrowing rate, and delayed return to estrus. Additionally, the respiratory system of swine infected with PRRSV is adversely affected, which is evidenced by lesions that appear in the lungs of infected swine. To combat the problems associated with PRRSV infection, vaccines have been developed which conferred immunity to then extant PRRSV strains.

Epidemics of an unusually severe form of PRRS, referred to hereafter as "atypical PRRS", were first recognized in North America in the latter part of 1996. They differed from epidemics of "typical PRRS" in that: 1) clinical signs were more prolonged as well as more severe; 2) the incidence of abortion was greater, especially during early and middle gestation; 3) there was a higher incidence of gilt and sow mortality; 4) PRRSV was less often isolated from aborted fetuses, stillborn pigs, and liveborn pigs—perhaps because abortions were more often the result of acute maternal illness rather than transplacental infection; 5) lung lesions of young affected pigs were more extensive; and 6) commercially available vaccines provided little or no protection. Collectively these observation indicated the emergence of more virulent and antigenically distinct strains of PRRSV and the need for a new generation of PRRS vaccines.

The most frequently used method for producing attenuated, live-virus vaccine is to serially passage the virus in a substrate (usually cell culture) other than the natural host (S) until it becomes sufficiently attenuated (i.e., reduced in virulence or diseases-producing ability) to be used as a vaccine. For the first passage, a cell culture is infected with the selected inoculum. After obtaining clear evidence of virus replication (e.g., virus-induced cytopathic effects [CPE] in the infected cells), an aliquot of the cell culture medium, or infected cells, or both, of the first passage are used to infect a second cell culture. The process is repeated until one or more critical mutations in the viral genome cause sufficient attenuation so that the virus can be safely used as a vaccine. The degree of attenuation is usually determined empirically by exposing the natural host (S) to progressively greater passage levels of the virus.

The above procedure is fundamentally sound and has been successfully used for the development of numerous vaccines for human and veterinary use. However, it is relatively inefficient because the logarithmic phase of virus replication, during which mutations are most likely to occur, is often completed long before evidence of virus replication becomes visibly obvious.

Therefore, there is a decided need in the art for a vaccine that confers effective immunity against PRRSV strains, including recently discovered atypical PRRSV strains. There is also a need in the art for a method of making such a vaccine. Finally, what is needed is a method of passaging a virus that attenuates the virus more efficiently than was heretofore thought possible with the resulting attenuated virus eliciting PRRSV specific antibodies in swine thereby conferring effective immunity against subsequent infection by PRRSV.

SUMMARY OF THE INVENTION

The present invention overcomes the problems outlined above, and provides attenuated, atypical PRRSV strains, and corresponding improved modified-live vaccines which confer effective immunity to newly discovered atypical PRRSV strains. "Effective immunity" refers to the ability of a vaccine to prevent swine PRRSV infections, including atypical PRRSV infections, which result in substantial clinical signs of the disease. That is to say, the immunized swine may or may not be serologically positive for PRRSV, but do not exhibit any substantial clinical symptoms. "Atypical PRRSV" refers to these new strains of PRRSV that are substantially more virulent than typical PRRSV strains.

In preferred forms, the vaccine of the invention includes live virus which has been attenuated in virulence. The resulting attenuated virus has been shown to be avirulent and to confer effective immunity. A particularly virulent strain of atypical PRRS (denominated JA-142) which caused especially severe symptoms of PRRS and represents the dominant strain of atypical PRRSV, was chosen for subsequent attenuation through passaging. The resultant attenuated virus has been deposited in the American Type Culture Collection (ATCC), Rockville, Md. on Feb. 2, 1999, and was accorded ATCC Accession No. VR-2638. This attenuated virus is a preferred Master Seed Virus (MSV) which has been subsequently passaged and developed as an effective PRRSV vaccine.

The name given the unattenuated virus, JA-142, arises from the restriction enzyme pattern. The 1 represents the inability of the enzyme MLU I to cleave the virus in open reading frame 5 (ORF 5). The 4 represents cleavage by Hinc II at base pair positions 118 and 249 of ORF 5 and short contiguous sequences. The 2 represents cleavage by Sac II at base pair position 54 of ORF 5 and short contiguous sequences.

Additionally, the present invention provides another way to differentiate between field strains of PRRSV and strain JA-142. The method is based upon differences in RNA cleavage by a restriction enzyme, NspI. Briefly, isolated PRRSV RNA is subjected to digestion by NspI. Digestion of the attenuated strain, JA-142, results in at least one additional fragment in comparison to field strains of PRRSV. In preferred methods, the RNA is isolated and RT-PCR is performed on the isolated RNA. This RNA is then subject to electrophoresis and a 1 Kd product is identified and purified for digestion by NspI. This digestion results in three fragments for JA-142 and either one or two fragments for PRRSV field strains.

Passaging of the virus to attenuation was accomplished using a novel method which resulted in increased efficiency. Specifically, the virus was kept in the logarithmic phase of replication throughout multiple cell culture passages in order to materially shorten the time to attenuation. This is achieved by ensuring that in each cell culture there is a substantial excess of initially uninfected cells relative to the number of virus present. Thus, by transferring only small numbers of virus from passage-to-passage, logarithmic replication is assured.

In practice, the process is normally initiated by inoculation of several separate cell cultures with progressively smaller viral aliquots (i.e., lesser numbers of virus in each culture.) For example, starting cultures could contain 200 μl, 20 μl and 2 μl viral aliquots. After an initial short incubation period (e.g., ~24 hours), the same viral aliquots (in the example, 200 μl, 20 μl and 2 μl) from each cell culture are transferred to individual fresh (previously uninfected) cultures, while the starting cultures are monitored until cytopathic effect (CPE) is or is not observed. This process is continued in serial order for multiple passages, using the same viral aliquots in each case and preserving the cultures for CPE observation. If all of the serial culture passages exhibit CPE after a selected number of passages are complete, the larger viral aliquot series may be terminated (in the example 200 μl and 20 μl), whereupon another series of progressively smaller viral aliquots are employed (e.g., 2 μl, 0.2 μl and 0.02 μl) and the process is again repeated, again keeping the cell cultures after transfer for CPE observation.

At some point in this successively smaller viral aliquot inoculation process, CPE will not be observed in a given cell culture. When this occurs, the next higher viral aliquot level showing CPE is substituted for the passage in which CPE was not observed, whereupon subsequent passages will be inoculated using previously employed viral aliquots.

Inasmuch as a virus will tend to become more efficient at infecting cells and also replicate to a higher infectivity titer for cell cultures over time, (which is especially true with RNA viruses such as PRRSV), it will be seen that smaller and smaller viral aliquots are required to maintain infection during serial transfer. The use of the smallest aliquot that maintains infection helps to assure that viral replication remains in a logarithmic phase throughout the process.

The DNA sequence of the attenuated passaged virus from the 201 st passage was then determined using conventional methods. The sequence of this attenuated virus was designated as MSV JA-142 Passage No. 201, the sequence of which is given as SEQ ID No. 1. The sequence of the virulent virus, JA-142, is given as SEQ ID No. 2.

As used herein, the following definitions will apply: "Sequence Identity" as it is known in the art refers to a relationship between two or more polypeptide sequences or two or more polynucleotide sequences, namely a reference sequence and a given sequence to be compared with the reference sequence. Sequence identity is determined by comparing the given sequence to the reference sequence after the sequences have been optimally aligned to produce the highest degree of sequence similarity, as determined by the match between strings of such sequences. Upon such alignment, sequence identity is ascertained on a position-by-position basis, e.g., the sequences are "identical" at a particular position if at that position, the nucleotides or amino acid residues are identical. The total number of such position identities is then divided by the total number of nucleotides or residues in the reference sequence to give % sequence identity. Sequence identity can be readily calculated by known methods, including but not limited to, those described in Computational Molecular Biology, Lesk, A. N., ed., Oxford University Press, New York (1988), Biocomputing: Informatics and Genome Projects, Smith, D. W., ed., Academic Press, New York (1993); Computer Analysis of Sequence Data, Part I, Griffin, A. M., and Griffin, H. G., eds., Humana Press, New Jersey (1994); Sequence Analysis in Molecular Biology, von Heinge, G., Academic Press (1987); Sequence Analysis Primer, Gribskov, M. and Devereux, J., eds., M. Stockton Press, New York (1991); and Carillo, H., and Lipman, D., SIAM J. Applied Math., 48: 1073 (1988), the teachings of which are incorporated herein by reference. Preferred methods to determine the sequence identity are designed to give the largest match between the sequences tested. Methods to determine sequence identity are codified in publicly available computer programs which determine sequence identity between given sequences. Examples of such programs include, but are not limited to, the GCG program package (Devereux, J., et al., Nucleic Acids Research, 12(1):387 (1984)), BLASTP, BLASTN and FASTA (Altschul, S. F. et al., J. Molec. Biol., 215:403–410 (1990). The BLASTX program is publicly available from NCBI and other sources (BLAST Manual, Altschul, S. et al., NCVI NLM NIH Bethesda, Md. 20894, Altschul, S. F. et al., J. Molec. Biol., 215:403–410 (1990), the teachings of which are incorporated herein by reference). These programs optimally align sequences using default gap weights in order to produce the highest level of sequence identity between the given and reference sequences. As an illustration, by a polynucleotide having a nucleotide sequence having at least, for example, 95% "sequence identity" to a reference nucleotide sequence, it is intended that the nucleotide sequence of the given polynucleotide is identical to the reference sequence except that the given polynucleotide sequence may include up to 5 point mutations per each 100 nucleotides of the reference nucleotide sequence. In other words, in a polynucleotide having a nucleotide sequence having at least 95% identity relative to the reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence. Analogously, by a polypeptide having a given amino acid sequence having at least, for example, 95% sequence identity to a reference amino acid sequence, it is intended that the given amino acid sequence of the polypeptide is identical to the reference sequence except that the given polypeptide sequence may include up to 5 amino acid alterations per each 100 amino acids of the reference amino acid sequence. In other words, to obtain a given polypeptide sequence having at least 95% sequence identity with a reference amino acid sequence, up to 5% of the amino acid residues in the reference sequence may be deleted or substituted with another amino acid, or a number of amino acids up to 5% of the total number of amino acid residues in the reference sequence may be inserted into the reference sequence. These alterations of the reference sequence may occur at the amino or the carboxy terminal positions of the reference amino acid sequence or anywhere between those terminal positions, interspersed either individually among residues in the reference sequence or in the one or more contiguous groups within the reference sequence. Preferably, residue positions which are not identical differ by conservative amino acid substitutions. However, conservative substitutions are not included as a match when determining sequence identity.

Similarly, "sequence homology", as used herein, also refers to a method of determining the relatedness of two sequences. To determine sequence homology, two or more sequences are optimally aligned as described above, and gaps are introduced if necessary. However, in contrast to "sequence identity", conservative amino acid substitutions are counted as a match when determining sequence homology. In other words, to obtain a polypeptide or polynucleotide having 95% sequence homology with a reference sequence, 95% of the amino acid residues or nucleotides in the reference sequence must match or comprise a conservative substitution with another amino acid or nucleotide, or a number of amino acids or nucleotides up to 5% of the total amino acid residues or nucleotides, not including conservative substitutions, in the reference sequence may be inserted into the reference sequence.

A "conservative substitution" refers to the substitution of an amino acid residue or nucleotide with another amino acid residue or nucleotide having similar characteristics or properties including size, hydrophobicity, etc., such that the overall functionality does not change significantly.

Isolated" means altered "by the hand of man" from its natural state., i.e., if it occurs in nature, it has been changed or removed from its original environment, or both. For example, a polynucleotide or polypeptide naturally present in a living organism is not "isolated," but the same polynucleotide or polypeptide separated from the coexisting materials of its natural state is "isolated", as the term is employed herein.

Preferably, sequences sharing at least about 75%, more preferably at least about 85%, still more preferably at least about 90% and most preferably at least about 95% sequence homology with SEQ ID No. 1 are effective as conferring immunity upon animals vaccinated with attenuated viruses containing such homologous sequences. Alternatively, sequences sharing at least about 65%, more preferably at least about 75%, still more preferably at least about 85%, and most preferably at least about 95% sequence identity with SEQ ID No. 1 are also effective at conferring immunity upon animals vaccinated with attenuated viruses containing such identical sequences.

DETAILED DESCRIPTION OF THE PREFERRED EMBODIMENT

Figure 1:
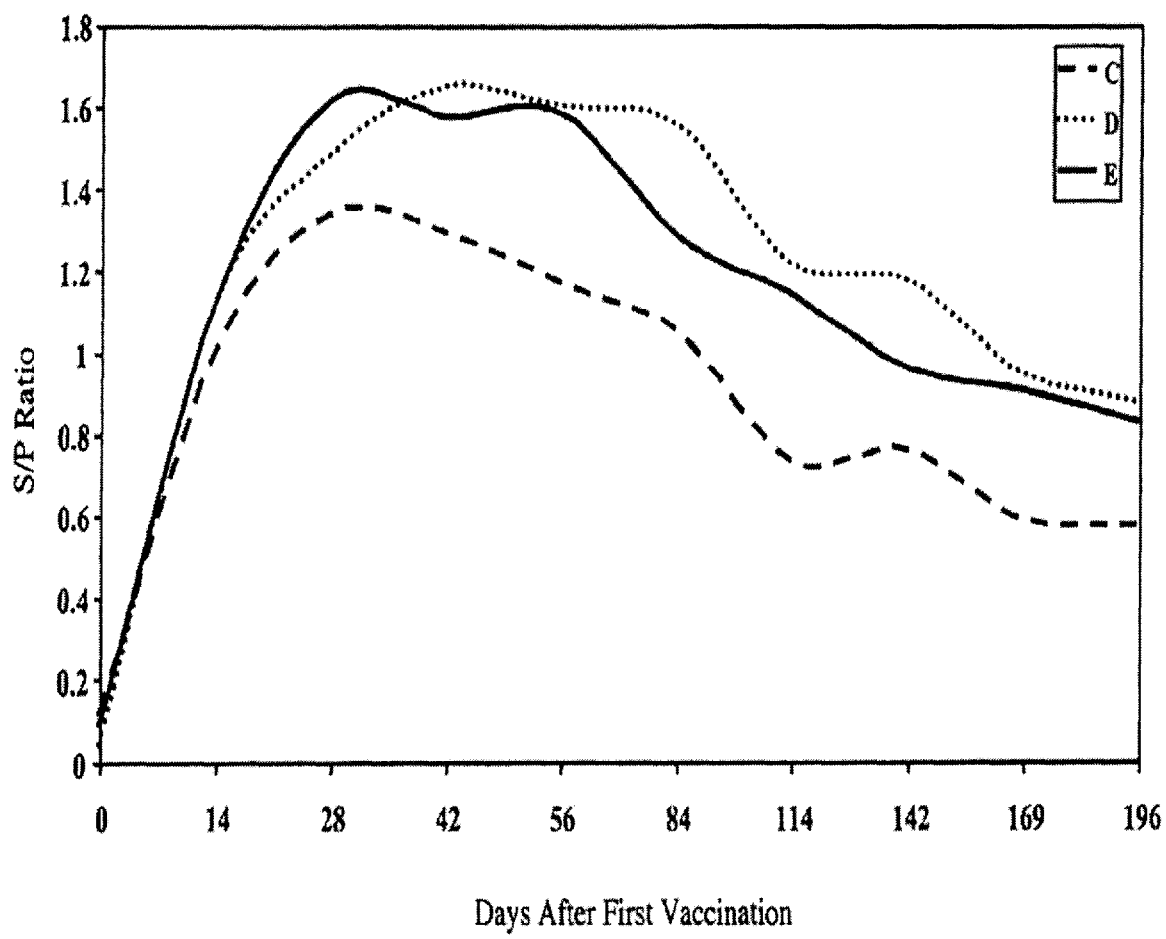
FIG. 1 is a graph illustrating the ratio of samples which tested positive for antibodies against PRRSV to the total number of samples over a 196 day testing period.

The following examples set forth preferred embodiments of the present invention. It is to be understood, however, that these examples are provided by way of illustration and nothing therein should be taken as a limitation upon the overall scope of the invention.

EXAMPLE 1

Materials and Methods

This example describes a passage method of attenuating viruses which maximizes attenuation efficiency by ensuring that the virus is preferably in a logarithmic phase of replication. Virus was passed (i.e. an aliquot of nutrient medium including the virus, unattached cells, and cell debris from a virus-infected cell culture was added to the nutrient medium of a non infected culture) at daily intervals. Different amounts of virus were added at each interval by using multiple cultures. For example, at the beginning, 200 $\mu$l was transferred to one non infected culture, 20 $\mu$l was added to a second noninfected culture, and 2 $\mu$l to a third noninfected culture. The goal was to have a sufficient amount of susceptible cells so that the replication cycles could continue until the next transfer. The procedure was deemed successful if the cells eventually showed CPE. However, because PRRSV-induced CPE do not appear until sometime after the logarithmic growth phase, passages were made before it was known whether or not they would be ultimately successful ("blind passages"). Passages that resulted in virus induced CPE were said to have resulted in a "take". If a passage did not result in a take, the passage was restarted using the highest dilution from the last passage which did result in a take. As more and more passages were made, the virus became more adapted to replicate in the cell line and less able to produce disease symptoms in its original host. These changes occur through random mutations that occur during replication.

Using this method, the following procedures were used to passage an exemplary virus in accordance with the present invention, MSV, JA-142. This strain was passaged in MARC-145 cell cultures at daily intervals. Twenty-four-well plates were used for the process to minimize the amount of cells and nutrient medium required, and to simplify the multiple-aliquot passage technique. Cells and nutrient medium were added to each well and the cells were allowed to form, or nearly form (greater than about 70%), a confluent monolayer. The nutrient medium comprised approximately 90% Earle's balanced salt solution minimal essential medium (MEM), 10% fetal calf serum and 0.05 mgm/ml of gentamicin sulfate. The volume of nutrient medium used was approximately 1 ml. Usually, three wells of a column were used for each amount of virus that was transferred. An aliquot of nutrient medium from the previous passage was transferred to the first well in the column at 48 or 72 hours, after the cell cultures had been prepared, nutrient medium from the first well was transferred to the second well of the same column at 72 or 96 hours and the third well of the same column at 96 or 120 hours. Plates were usually set up twice a week so sometimes the fourth well of the column was used and sometimes it was not used. Passaging conditions were maintained at 37° C. in a moist atmosphere containing 5% $CO_2$.

Different sized aliquots (having different amounts of virus) for each passage were tested to determine if the amount of virus was sufficient to induce CPE. For example, a separate series of aliquot transfers (passages) of 200 $\mu$l, 20 $\mu$l, and 2 $\mu$l, respectively, was used until the smaller aliquots consistently exhibited CPE with the goal being to transfer the smallest aliquot that produced CPE. When the smallest aliquot (e.g. 2 $\mu$l) of the group of aliquots being tested consistently resulted in CPE, smaller amounts were tested (e.g. 0.2 $\mu$l and 0.02 $\mu$l). When a certain dilution did not exhibit CPE, that series of cultures was restarted with the next lower amount which did result in CPE at that passage (i.e. if the 2 µl transfer was unsuccessful at producing CPE in the 25th passage but the 20 µl transfer in the 25th passage was successful, the 2 µl transfer was repeated using 20 µl with 2 µl transfers resuming for the 26th passage.)

Using this method, the smallest amount of virus necessary to transfer to obtain CPE was determined. Virus was passed successfully at daily intervals using the following amounts of virus-infected nutrient medium (which reflect the highest dilution [i.e., smallest aliquot] which resulted in CPE keeping in mind that other dilutions would also work):

| Passage Number | Amount Transferred |
|---|---|
| 3–21 | 200 µl |
| 22, 23 | 20 µl |
| 24–41 | 200 µl |
| 42–83 | 20/200 µl (alternating) |
| 84–90 | 20 µl |
| 91–112 | 2 µl |
| 113 | 0.2 µl |
| 114–116 | 2 µl |
| 117 | 0.2 µl |
| 118–120 | 2 µl |
| 121 | 0.2 µl |
| 122–124 | 2 µl |
| 125–167 | 0.2 µl |
| 168 | 0.02 µl |
| 169–171 | 0.2 µl |
| 172 | 0.02 µl |
| 173–175 | 0.2 µl |
| 176 | 0.02 µl |
| 177–179 | 0.2 µl |
| 180 | 0.02 µl |
| 181–183 | 0.2 µl |
| 184 | 0.02 µl |
| 185–187 | 0.2 µl |
| 188 | 0.02 µl |
| 189–191 | 0.2 µl |
| 192 | 0.02 µl |
| 193–195 | 0.2 µl |
| 196 | 0.02 µl |
| 197 | 0.2 µl |

Results and Discussion

The passaging of the virus using the above method resulted in an attenuated PRRSV, JA-142. As is apparent, the virus became more adapted to replicate in the cell culture and therefore required a smaller amount of virus-infected nutrient medium to be transferred as passaging continued. For transfers using a very small amount of virus infected nutrient medium (e.g. 0.2 µl or 0.02 µl), a separate dilution was required. This dilution was accomplished by adding a small amount of virus-infected nutrient medium to a larger amount of nutrient medium. For example, to obtain a transfer of 0.2 µl, 2 µl of virus infected nutrient medium was added to 20 µl of nutrient medium and 2 µl of this dilution was added to the next culture in the series. Using this approach, the highest dilution which resulted in CPE was used and the time necessary for passaging the virus was minimized. Passaging at daily intervals ensured that the virus was always in a logarithmic phase of replication. Daily transferring also ensured that there was an adequate number of cells for virus replication.

Because the mutations (which are probably cumulative) that are likely to result in attenuation only occur during replication, there is no advantage to having substantially all cells infected and replication either proceeding at a slower rate or stopping before the next transfer. Based on previous studies of PRRSV, it was known that the replication cycle is about 8 hours, therefore, transferring a minimal amount of virus from virus-infected nutrient medium to uninfected nutrient medium at daily intervals results in the virus always having plenty of cells within which to replicate.

As can be readily appreciated, passaging using this method results in a savings of time that was heretofore thought impossible (i.e. each passage required less time). This is especially important when a high number of passages are required for adequate virus attenuation. If each passage, using old methods, was performed at a 3 day interval, a procedure requiring 200 passages would take 400 fewer days using the method of the present invention.

EXAMPLE 2

Materials and Methods

This example determined if passage 200 of PRRS Virus, JA-142, would revert in virulence when passed in the host animal six times. This study consisted of six groups. Five pigs from group 1 (principle group) were inoculated intra-nasally with PRRS MSV, JA-142 passage 200, while three pigs from group 1A, (control group) were inoculated intra-nasally with sterile diluent. The animals were provided commercial feed and water ad libitum throughout the study. Pigs of both treatment groups were monitored daily for clinical signs (appearance, respiratory, feces, etc.). After six days, the animals were weighed, bled and sacrificed. After scoring the lungs for lesions, lung lavages were collected from each animal. The lung lavages were frozen and thawed one time, and a pool was prepared using 2.0 ml of serum and 2.0 ml of lung lavage from each animal within a group to prepare Backpassage 1 and 1A, respectively. This pool was used to challenge (intra-nasally) the animals in group 2 and group 2A, respectively. This process was repeated for groups 3 and 3A through 6 and 6A. Animals in each group were housed in separate but identical conditions.

Following inoculation, blood samples were collected and body temperatures were monitored. Rectal temperatures were measured for each animal periodically from −1 DPE (days post exposure) to 6 DPE and averaged together with other animal temperatures from the same group. The health status of each animal was monitored daily for the duration of the study. Results were compiled and scored on a daily observation form. The scoring parameters are as follows:

1. Appearance
   normal=0; depressed=1; excited=2; comatose/death=30.
2. Respiration
   normal=0; sneeze=1; cough=1; rapid/short=2; labored=3.
3. Feces
   normal=0; dry=1; loose=2; fluid=3.
4. Eyes
   normal=0; watery=1; matted=2; sunken=3.
5. Nostrils
   normal=0; watery discharge=1; red/inflamed=2; crusted ulcers=3.
6. Mouth
   normal=0; slobbers=2; ulcer=3.
7. Activity
   NA
8. Appetite
   normal=0; decreased=1; anorexic (none)=3. 9. Other Animals were also weighed prior to inoculation and at necropsy. Average weight gains for each group were calculated for comparison. PRRS Enzyme Linked Immuno-Absorbent Assays (ELISA) and serum neutralization (SN) assays were performed following the exposures of the animals with test and control articles. Attempts to isolate PRRSV from serum samples were performed on MA-104 cells. Prior to and following vaccination, total white blood cell counts were determined using COULTER COUNTER MODEL Z1, Coulter Corp., Miami, Fla. At necropsy, the lungs of each animal were scored. Lung scoring was done by separating the lung into 7 sections and determining the percentage of lung involvement (the percentage of the lung area affected as shown by lesions or redness for each section and multiplying by the approximate area of the whole lung) that percentage of total lung area that the section encompasses. Parameters for lung scoring are as follows:

| | | | |
|---|---|---|---|
| Left Apical Lobe % of involvement | X | 0.10 | = __ |
| Left Cardiac Lobe % of involvement | X | 0.10 | = __ |
| Left Diaphragmatic Lobe % of involvement | X | 0.25 | = __ |
| Right Apical Lobe % of involvement | X | 0.10 | = __ |
| Right Cardiac Lobe % of involvement | X | 0.10 | = __ |
| Right Diaphragmatic Lobe % of involvement | X | 0.25 | = __ |
| Intermediate Lobe of Right Lung % of involvement | X | 0.10 | = __ |
| Total (Sum of all values in the far right column) | | | = __ |

Results and Discussion

Each group of pigs was monitored for six days following vaccination. Clinical scores were low in all groups. Clinical score results are given in Table 1.

TABLE 1

Daily Clinical Scores

| Treatment | Pig # | Day-1 | Day 0 | Day 1 | Day 2 | Day 3 | Day 4 | Day 5 | Day 6 | Average |
|---|---|---|---|---|---|---|---|---|---|---|
| Group 1 | | | | | | | | | | |
| JA-142 psg 200 | 545 | 0 | 0 | 2 | 0 | 0 | 0 | 0 | 0 | 0.25 |
| | 551 | 0 | 0 | 0 | 0 | 0 | 0 | 0 | 0 | 0 |
| | 561 | 0 | 0 | 0 | 0 | 0 | 0 | 0 | 0 | 0 |
| | 565 | 0 | 0 | 0 | 0 | 0 | 0 | 0 | 0 | 0 |
| | 806 | 0 | 0 | 0 | 0 | 0 | 0 | 0 | 0 | 0 |
| | Average | 0 | 0 | 0.4 | 0 | 0 | 0 | 0 | 0 | 0.05 |
| Saline | 550 | 0 | 0 | 0 | 0 | 0 | 0 | 0 | 0 | 0 |
| | 568 | 0 | 0 | 0 | 0 | 0 | 0 | 0 | 0 | 0 |
| | 801 | 0 | 0 | 0 | 0 | 0 | 0 | 0 | 0 | 0 |
| | Average | 0 | 0 | 0 | 0 | 0 | 0 | 0 | 0 | 0 |
| Group 2 | | | | | | | | | | |
| Backpassage 1 | 546 | 0 | 0 | 0 | 0 | 0 | 0 | 0 | 0 | 0 |
| | 553 | 0 | 0 | 0 | 0 | 0 | 0 | 0 | 0 | 0 |
| | 562 | 0 | 0 | 0 | 0 | 0 | 1 | 0 | 0 | 0.125 |
| | 572 | 0 | 0 | 0 | 0 | 0 | 0 | 0 | 0 | 0 |
| | 573 | 0 | 0 | 0 | 0 | 2 | 0 | 0 | 0 | 0.25 |
| | Average | 0 | 0 | 0 | 0 | 0.4 | 0.2 | 0 | 0 | 0.075 |
| Backpassage 1 | 556 | 0 | 0 | 0 | 0 | 0 | 0 | 0 | 0 | 0 |
| | 566 | 0 | 0 | 0 | 0 | 0 | 0 | 0 | 0 | 0 |
| | 802 | 0 | 0 | 0 | 0 | 0 | 0 | 0 | 0 | 0 |
| | Average | 0 | 0 | 0 | 0 | 0 | 0 | 0 | 0 | 0 |
| Group 3 | | | | | | | | | | |
| Backpassage 2 | 548 | 0 | 0 | 0 | 0 | 0 | 0 | 0 | 0 | 0 |
| | 567 | 0 | 0 | 0 | 0 | 0 | 0 | 0 | 0 | 0 |
| | 569 | 0 | 0 | 0 | 0 | 1 | 1 | 0 | 0 | 0.25 |
| | 574 | 0 | 0 | 0 | 0 | 0 | 0 | 0 | 0 | 0 |
| | 804 | 0 | 0 | 0 | 0 | 0 | 0 | 0 | 0 | 0 |
| | Average | 0 | 0 | 0 | 0 | 0.2 | 0.2 | 0 | 0 | 0.05 |
| Backpassage 2A | 547 | 0 | 0 | 0 | 0 | 0 | 0 | 0 | 0 | 0 |
| | 5564 | 0 | 0 | 0 | 0 | 0 | 0 | 0 | 0 | 0 |
| | 805 | 0 | 0 | 0 | 0 | 0 | 0 | 0 | 0 | 0 |
| | Average | 0 | 0 | 0 | 0 | 0 | 0 | 0 | 0 | 0 |
| Group 4 | | | | | | | | | | |
| Backpassage 3 | 549 | 0 | 0 | 0 | 0 | 0 | 0 | 0 | 0 | 0 |
| | 554 | 0 | 0 | 0 | 0 | 0 | 0 | 0 | 0 | 0 |
| | 563 | 0 | 0 | 0 | 0 | 0 | 0 | 0 | 0 | 0 |
| | 570 | 0 | 0 | 0 | 0 | 0 | 0 | 0 | 0 | 0 |
| | 803 | 0 | 0 | 0 | 0 | 0 | 0 | 0 | 0 | 0 |
| | Average | 0 | 0 | 0 | 0 | 0 | 0 | 0 | 0 | 0 |
| Backpassage 3A | 560 | 0 | 0 | 0 | 0 | 0 | 0 | 0 | 0 | 0 |
| | 571 | 0 | 0 | 0 | 0 | 0 | 0 | 0 | 0 | 0 |
| | 575 | 0 | 0 | 0 | 0 | 0 | 0 | 0 | 0 | 0 |
| | Average | 0 | 0 | 0 | 0 | 0 | 0 | 0 | 0 | 0 |
| Group 5 | | | | | | | | | | |
| Backpassage 4 | 1 | 0 | 2 | 0 | 0 | 2 | 0 | 2 | 2 | 1 |
| | 2 | 0 | 0 | 0 | 0 | 0 | 0 | 0 | 0 | 0 |
| | 3 | 2 | 0 | 2 | 2 | 2 | 2 | 2 | 2 | 1.75 |

TABLE 1-continued

Daily Clinical Scores

| Treatment | Pig # | Day-1 | Day 0 | Day 1 | Day 2 | Day 3 | Day 4 | Day 5 | Day 6 | Average |
|---|---|---|---|---|---|---|---|---|---|---|
| | 4 | 0 | 0 | 0 | 0 | 0 | 0 | 0 | 0 | 0 |
| | 5 | 0 | 0 | 0 | 0 | 0 | 0 | 0 | 0 | 0 |
| | Average | 0.4 | 0.4 | 0.4 | 0.4 | 0.8 | 0.4 | 0.8 | 0.8 | 0.55 |
| Backpassage 4A | 6 | 0 | 0 | 0 | 0 | 0 | 0 | 0 | 0 | 0 |
| | 7 | 0 | 0 | 2 | 2 | 2 | 2 | 2 | 2 | 1.5 |
| | 8 | 0 | 0 | 0 | 0 | 0 | 0 | 0 | 0 | 0 |
| | Average Group 6 | 0 | 0.08 | 0.48 | 0.48 | 0.56 | 0.48 | 0.56 | 0.56 | 0.4 |
| Backpassage 5 | 10 | 0 | 0 | 0 | 0 | 2 | 0 | 0 | 2 | 0.5 |
| | 12 | 0 | 0 | 0 | 2 | 2 | 0 | 0 | 2 | 0.75 |
| | 14 | 0 | 0 | 0 | 0 | 0 | 0 | 0 | 0 | 0 |
| | 15 | 2 | 2 | 2 | 0 | 0 | 0 | 0 | 2 | 1 |
| | 16 | 2 | 2 | 2 | 0 | 0 | 1 | 1 | 2 | 1.25 |
| | Average | 0.8 | 0.8 | 0.8 | 0.4 | 0.8 | 0.2 | 0.2 | 1.6 | 0.7 |
| Backpassage 5A | 9 | 0 | 0 | 0 | 0 | 0 | 0 | 0 | 0 | 0 |
| | 11 | 2 | 2 | 0 | 0 | 0 | 0 | 0 | 0 | 0.5 |
| | 13 | 0 | 0 | 0 | 0 | 0 | 0 | 0 | 0 | 0 |
| | Average | 0.666667 | 0.56 | 0.16 | 0.08 | 0.16 | 0.04 | 0.04 | 0.32 | 0.253333 |

There were no significant differences between groups for rectal temperatures or daily weight gains. All lung scores were negative.

Serologically, ELISA S/P ratios and SN titers were negative throughout each group's trial period. Virus isolation was attempted on all serum samples and lung lavages. By day 6, 60–100% of the serum samples from the groups given JA-142, passage 200, and subsequent back passes were positive. The groups given saline were negative. In the first three passes, virus was recovered in the lung lavages from only 20–40% of the pigs, but by the last three passes, the virus was recovered from 50–80% of the pigs.

Based on this data, JA-142 passage 200 did not revert to virulence when passed through pigs six times.

EXAMPLE 3

Materials and Methods

This example demonstrated that the level of attenuation of safety of MSV, JA-142, passage 200 did not change significantly during six backpassages in the host animal. Evaluation of level of attenuation or safety was performed using the pregnant sow model and monitoring the effect on reproductive performance. This model is the most sensitive test system and does not rely upon subjective factors for virulence testing. This example consisted of four groups (A, B, C & D) having seven sows per group. Group A was inoculated intra-nasally with PRRS MSV, JA-142 passage 200. Group B was inoculated intra-nasally with JA-142, passage 200, Backpassage 6. Group C was inoculated intra-nasally with sterile diluent, to act as normal controls. Group D was inoculated intra-nasally with PRRSV JA-142, passage 4. The test articles (challenge with JA-142, passage 4) were given at about 93 days gestation. Body temperatures of the sows were monitored for the first seven days following vaccination. Blood samples were collected from the sows once a week and at time of farrowing. Blood samples were collected and weights were recorded from piglets at birth, 7, and 14 days of age. The health status of each animal was monitored daily for the duration of the study up to and following farrowing for 14 days. The farrowing performance was evaluated by observing the health status of the piglets born.

PRRS ELISA assays were performed following the exposures of the sows with the test article. PRRS ELISA assays were also performed on the piglet sera weekly following farrowing. Following exposure to the test article, attempts to isolate PRRSV from serum samples were performed on MA-104 cells. Rectal temperatures were measured periodically from 0 days post vaccination (DPV) to 7 DPV and the average temperature of each group was determined. Prior to and after inoculation, total white blood cell counts were determined as in Example 1. Clinical observations of the sows, as in Example 2, were made from −1 DPV through farrowing. Clinical observations of the piglets were made from farrowing until 14 days of age. Finally, at necropsy, the lungs of each piglet were scored for percent lung involvement.

Results

The ELISA results indicate that the animals used in this study were naive to PRRSV. Those animals that received virus inocula, groups A, B, and D, sero-converted at 14 days post treatment. Three sows of group B remained negative at 14 days post treatment. At the time of farrowing, the negative sows of group B tested positive for antibody to PRRSV.

The pigs' ELISA results indicated that the majority of the piglets born to sows of group A and group B were sampled after they had nursed. Those pigs that were negative at zero days post farrowing (0 DPF) tested positive at 7 DPF. All pigs born to sows of group C tested sero-negative throughout the study. Only a few pigs were tested from group D, since the majority were either stillborn or mummies. Half of those pigs that were tested were sero-positive. This indicated that the sero-negative pigs were sampled prior to nursing or they were not capable of nursing. All piglets born to sows of group D died before 7 DPF. Isolations of PRRSV from the sows of groups A and B were sporadic. Although the results of the ELISA test indicated that these sows were successfully inoculated with the viral test articles, many remained negative for virus isolation from serum.

The majority of pigs born to sows from groups A and B tested positive for virus isolation during the performance of the study. The litter born to one sow of group A never tested positive and the litter born to one sow of group B had only two of eight piglets test positive for virus isolation. No virus was recovered from the piglets born to sows from group C. Virus was recovered from the majority (71%) of piglets born from sows of group D.

Post treatment rectal temperatures were unremarkable. The groups that were treated with either MSV, backpassage 6 or sterile diluent experienced no measurements exceeding 101.7° F. Group D, treated with JA-142, passage 4, had four (out of seven) sows that experienced temperatures that exceeded 102° F. with one sow reaching 103.4° F. for one of the days. The weight gain performance of the piglets born to sows of groups A (treated with MSV) and B (treated with MSV, backpassage 6) was greater than that of the pigs born to the control sows of group C. The average weight gain for the 14 day observation period was 7.9 lbs. For group A, it was 7.7 lbs; for group B and group C it was 6.9 lbs. The difference in the weight gain was not related to the size of the litter remaining at 14 days. The average litter sizes at 14 days post farrowing (DPF) were 9 for group A, 7 for group B, and 10 for group C. No pig born to the sows of group D survived beyond 3 DPF.

The white blood cell (WBC) counts for the sows of groups A, B, and C remained relatively constant. The average percentages of the pre-challenge values were equal to or greater than 92% for the duration of the observation period. Three sows of group D experienced WBC counts that were lower than the expected normal range ($7–20 \times 10^6$/ml).

The post inoculation clinical scores were unremarkable for the sows of groups A and B. Several sows of group C were observed to experience clinical signs over a period of several days. The majority of the clinical symptoms observed were in the category of decreased appetite, respiratory symptoms, and depression. One sow of group C died on trial day 31 of chronic bacterial pneumonia. Six of the seven sows of group D were observed to have clinical signs, primarily of varying degrees in severity, of lost appetite, ranging from decreased to anorexic. Results of the clinical scoring for the sows are given in Table 2.

TABLE 2

Sow Clinical Scores

| Treatment | Sow # | −3 | −2 | −1 | 0 | 1 | 2 | 3 | 4 | 5 | 6 | 7 | 8 | 9 | 10 | 11 | 12 |
|---|---|---|---|---|---|---|---|---|---|---|---|---|---|---|---|---|---|
| Group A | 98 | 0 | 0 | 0 | 0 | 0 | 0 | 0 | 0 | 0 | 0 | 0 | 0 | 0 | 0 | 0 | 0 |
| JA-142 MSV | 133 | 0 | 0 | 0 | 0 | 0 | 0 | 0 | 0 | 0 | 0 | 0 | 0 | 0 | 0 | 0 | 0 |
| Passage 200 | 147 | 0 | 0 | 0 | 0 | 0 | 0 | 0 | 0 | 0 | 0 | 0 | 0 | 0 | 0 | 0 | 0 |
| | 178 | 0 | 0 | 0 | 0 | 0 | 0 | 0 | 0 | 0 | 0 | 0 | 0 | 0 | 0 | 0 | 0 |
| | 215 | 0 | 0 | 0 | 0 | 0 | 0 | 0 | 0 | 0 | 0 | 0 | 0 | 0 | 0 | 0 | 0 |
| | 233 | 0 | 0 | 0 | 0 | 0 | 0 | 0 | 0 | 0 | 0 | 0 | 0 | 0 | 0 | 0 | 0 |
| | 243 | 0 | 0 | 0 | 0 | 0 | 0 | 0 | 0 | 0 | 0 | 0 | 0 | 0 | 0 | 0 | 0 |
| | Avg. | 0 | 0 | 0 | 0 | 0 | 0 | 0 | 0 | 0 | 0 | 0 | 0 | 0 | 0 | 0 | 0 |

| | | 13 | 14 | 15 | 16 | 17 | 18 | 19 | 20 | 21 | 22 | 23 | 24 | 25 | 26 | 27 | 28 |
|---|---|---|---|---|---|---|---|---|---|---|---|---|---|---|---|---|---|
| Group A | 98 | 0 | 0 | 0 | 0 | 0 | 0 | 0 | 0 | 0 | 0 | 0 | 0 | 0 | 0 | 0 | 0 |
| JA-142 MSV | 133 | 0 | 0 | 0 | 0 | 0 | 0 | 0 | 0 | 0 | 0 | 0 | 0 | 0 | 0 | 0 | 0 |
| Passage 200 | 147 | 0 | 0 | 0 | 0 | 0 | 0 | 0 | 0 | 0 | 0 | 0 | 0 | 0 | 0 | 0 | 0 |
| | 178 | 0 | 2 | 0 | 0 | 0 | 0 | 0 | 0 | 0 | 0 | 0 | 0 | 0 | 0 | 0 | 0 |
| | 215 | 0 | 0 | 0 | 0 | 0 | 0 | 0 | 0 | 0 | 0 | 0 | 0 | 0 | 0 | 0 | 0 |
| | 233 | 0 | 0 | 0 | 0 | 0 | 0 | 0 | 0 | 0 | 0 | 0 | 0 | 0 | 0 | 0 | 0 |
| | 243 | 0 | 2 | 0 | 0 | 0 | 0 | 0 | 0 | 0 | 0 | 0 | 0 | 0 | 0 | 0 | 0 |
| | Avg. | 0 | 0.6 | 0 | 0 | 0 | 0 | 0 | 0 | 0 | 0 | 0 | 0 | 0 | 0 | 0 | 0 |

| | | 29 | 30 | 31 | 32 | 33 | 34 | 35 | 36 | 37 | 38 | 39 | 40 | 41 | 42 | 43 | 44 |
|---|---|---|---|---|---|---|---|---|---|---|---|---|---|---|---|---|---|
| Group A | 98 | 0 | 0 | 0 | 0 | 0 | 0 | 0 | 0 | 0 | 0 | 0 | 0 | 0 | 0 | 0 | 0 |
| JA-142 MSV | 133 | 0 | 0 | 0 | 0 | 0 | 0 | 0 | 0 | 0 | 0 | 0 | 0 | 0 | 0 | 0 | 0 |
| Passage 200 | 147 | 0 | 0 | 0 | 0 | 0 | 0 | 0 | 0 | 0 | 0 | 0 | 0 | 0 | 0 | 0 | 0 |
| | 178 | 0 | 0 | 0 | 0 | 0 | 0 | 0 | 0 | 0 | 0 | 0 | 0 | 0 | 0 | 0 | 0 |
| | 215 | 0 | 0 | 0 | 0 | 0 | 0 | 0 | 0 | 0 | 0 | 0 | 0 | 0 | 0 | 0 | 0 |
| | 233 | 0 | 0 | 0 | 0 | 0 | 0 | 0 | 0 | 0 | 0 | 0 | 0 | 0 | 0 | 0 | 0 |
| | 243 | 0 | 0 | 0 | 0 | 0 | 0 | 0 | 0 | 0 | 0 | 0 | 0 | 0 | 0 | 0 | 0 |
| | Avg. | 0 | 0 | 0 | 0 | 0 | 0 | 0 | 0 | 0 | 0 | 0 | 0 | 0 | 0 | 0 | 0 |

| Treatment | Sow # | −3 | −2 | −1 | 0 | 1 | 2 | 3 | 4 | 5 | 6 | 7 | 8 | 9 | 10 | 11 | 12 |
|---|---|---|---|---|---|---|---|---|---|---|---|---|---|---|---|---|---|
| Group B | 49 | 0 | 0 | 0 | 0 | 0 | 0 | 0 | 0 | 0 | 0 | 0 | 0 | 0 | 0 | 0 | 0 |
| Backpassage 6 | 100 | 0 | 0 | 0 | 0 | 0 | 0 | 0 | 0 | 0 | 0 | 0 | 0 | 0 | 0 | 0 | 0 |
| | 135 | 0 | 0 | 0 | 0 | 0 | 0 | 0 | 0 | 0 | 0 | 0 | 0 | 0 | 0 | 0 | 0 |
| | 149 | 0 | 0 | 0 | 0 | 0 | 0 | 0 | 0 | 0 | 0 | 0 | 0 | 1 | 1 | 1 | 1 |
| | 209 | 0 | 0 | 0 | 0 | 0 | 0 | 0 | 0 | 0 | 0 | 0 | 0 | 0 | 0 | 0 | 0 |
| | 212 | 0 | 0 | 0 | 0 | 0 | 0 | 0 | 0 | 0 | 0 | 0 | 0 | 0 | 0 | 0 | 0 |
| | 226 | 0 | 0 | 0 | 0 | 0 | 0 | 0 | 0 | 0 | 0 | 0 | 0 | 0 | 0 | 0 | 0 |
| | Avg. | 0 | 0 | 0 | 0 | 0 | 0 | 0 | 0 | 0 | 0 | 0 | 0 | 0.1 | 0.1 | 0.1 | 0.1 |

| | | 13 | 14 | 15 | 16 | 17 | 18 | 19 | 20 | 21 | 22 | 23 | 24 | 25 | 26 | 27 | 28 |
|---|---|---|---|---|---|---|---|---|---|---|---|---|---|---|---|---|---|
| Group B | 49 | 0 | 0 | 0 | 0 | 0 | 0 | 0 | 0 | 0 | 0 | 0 | 0 | 0 | 0 | 0 | 0 |
| Backpassage 6 | 100 | 0 | 0 | 0 | 0 | 0 | 0 | 0 | 0 | 0 | 0 | 0 | 0 | 0 | 0 | 0 | 0 |
| | 135 | 0 | 0 | 0 | 0 | 0 | 0 | 0 | 0 | 0 | 0 | 0 | 0 | 0 | 0 | 0 | 0 |
| | 149 | 0 | 0 | 0 | 0 | 0 | 0 | 0 | 1 | 1 | 0 | 0 | 0 | 0 | 0 | 0 | 0 |
| | 209 | 0 | 0 | 0 | 0 | 0 | 0 | 0 | 0 | 0 | 0 | 0 | 0 | 0 | 0 | 0 | 0 |
| | 212 | 0 | 0 | 0 | 0 | 0 | 0 | 0 | 0 | 0 | 0 | 0 | 0 | 0 | 0 | 0 | 0 |
| | 226 | 0 | 0 | 0 | 0 | 0 | 0 | 0 | 0 | 0 | 0 | 0 | 0 | 0 | 0 | 0 | 0 |
| | Avg. | 0 | 0 | 0 | 0 | 0 | 0 | 0 | 0.1 | 0.1 | 0 | 0 | 0 | 0 | 0 | 0 | 0 |

TABLE 2-continued

Sow Clinical Scores

| | | 29 | 30 | 31 | 32 | 33 | 34 | 35 | 36 | 37 | 38 | 39 | 40 | 41 | 42 | 43 | 44 |
|---|---|---|---|---|---|---|---|---|---|---|---|---|---|---|---|---|---|
| Group B Backpassage 6 | 49 | 0 | 0 | 0 | 0 | 0 | 0 | 0 | 0 | 0 | 0 | 0 | 0 | 0 | 0 | 0 | 0 |
| | 100 | 0 | 0 | 0 | 0 | 0 | 0 | 0 | 0 | 0 | 0 | 0 | 0 | 0 | 0 | 0 | 0 |
| | 135 | 0 | 0 | 0 | 0 | 0 | 0 | 0 | 0 | 0 | 0 | 0 | 0 | 0 | 0 | 0 | 0 |
| | 149 | 0 | 0 | 0 | 0 | 0 | 0 | 0 | 0 | 0 | 0 | 2 | 2 | 2 | 2 | 2 | 2 |
| | 209 | 0 | 0 | 0 | 0 | 0 | 0 | 0 | 0 | 0 | 0 | 0 | 0 | 0 | 0 | 0 | 0 |
| | 212 | 0 | 0 | 0 | 0 | 0 | 0 | 0 | 0 | 0 | 0 | 0 | 0 | 0 | 0 | 0 | 0 |
| | 226 | 0 | 0 | 0 | 0 | 0 | 0 | 0 | 0 | 0 | 0 | 0 | 0 | 0 | 0 | 0 | 0 |
| | Avg. | 0 | 0 | 0 | 0 | 0 | 0 | 0 | 0 | 0 | 0 | 0.3 | 0.3 | 0.3 | 0.3 | 0.3 | 0.3 |

| Treatment | Sow # | −3 | −2 | −1 | 0 | 1 | 2 | 3 | 4 | 5 | 6 | 7 | 8 | 9 | 10 | 11 | 12 |
|---|---|---|---|---|---|---|---|---|---|---|---|---|---|---|---|---|---|
| Group C Sterile Diluent | 58 | 0 | 0 | 0 | 0 | 0 | 0 | 0 | 0 | 0 | 0 | 0 | 0 | 0 | 0 | 0 | 0 |
| | 113 | 0 | 0 | 0 | 0 | 0 | 0 | 0 | 0 | 0 | 0 | 1 | 3 | 3 | 5 | 3 | 3 |
| | 117 | 0 | 0 | 0 | 0 | 0 | 0 | 0 | 0 | 0 | 0 | 0 | 0 | 0 | 0 | 1 | |
| | 144 | 0 | 0 | 0 | 0 | 0 | 0 | 0 | 0 | 0 | 0 | 0 | 0 | 0 | 0 | 0 | 0 |
| | 156 | 0 | 0 | 0 | 0 | 0 | 0 | 0 | 0 | 0 | 0 | 0 | 0 | 0 | 0 | 0 | 0 |
| | 166 | 0 | 0 | 0 | 0 | 0 | 0 | 0 | 0 | 0 | 0 | 0 | 0 | 0 | 0 | 0 | 0 |
| | Avg. | 0 | 0 | 0 | 0 | 0 | 0 | 0 | 0 | 0 | 0 | 0.2 | 0.5 | 0.5 | 0.8 | 0.7 | 0.7 |

| | | 13 | 14 | 15 | 16 | 17 | 18 | 19 | 20 | 21 | 22 | 23 | 24 | 25 | 26 | 27 | 28 |
|---|---|---|---|---|---|---|---|---|---|---|---|---|---|---|---|---|---|
| Group C Sterile Diluent | 58 | 0 | 0 | 0 | 0 | 0 | 0 | 0 | 0 | 0 | 0 | 0 | 0 | 0 | 0 | 0 | 0 |
| | 113 | 3 | 3 | 3 | 3 | 3 | 3 | 4 | 4 | 4 | 4 | 6 | 6 | 2 | 4 | 2 | 2 |
| | 117 | 0 | 0 | 0 | 0 | 0 | 0 | i | 5 | 5 | 5 | 5 | 5 | 2 | 4 | 1 | |
| | 144 | 0 | 0 | 0 | 0 | 0 | 0 | 0 | 0 | 0 | 0 | 0 | 0 | 0 | 0 | 0 | 0 |
| | 156 | 2 | 0 | 0 | 0 | 0 | 0 | 0 | 0 | 0 | 0 | 0 | 0 | 0 | 0 | 0 | 0 |
| | 166 | 0 | 0 | 0 | 0 | 0 | 0 | 0 | 0 | 0 | 0 | 0 | 0 | 0 | 0 | 0 | 0 |
| | Avg. | 0.8 | 0.5 | 0.5 | 0.5 | 0.5 | 0.5 | 0.8 | 1.5 | 1.5 | 1.5 | 1.8 | 1.8 | 0.7 | 1.3 | 0.5 | 0.5 |

| | | 29 | 30 | 31 | 32 | 33 | 34 | 35 | 36 | 37 | 38 | 39 | 40 | 41 | 42 | 43 | 44 |
|---|---|---|---|---|---|---|---|---|---|---|---|---|---|---|---|---|---|
| Group C Sterile Diluent | 58 | 0 | 0 | 0 | 0 | 0 | 0 | 0 | 0 | 0 | 0 | 0 | 0 | 0 | 0 | 0 | 0 |
| | 113 | 2 | 2 | 30 | | | | | | | | | | | | | |
| | 117 | 2 | 2 | 0 | 0 | 0 | 0 | 0 | 0 | 0 | 0 | 0 | 0 | 0 | 0 | 0 | 0 |
| | 144 | 0 | 0 | 0 | 0 | 0 | 0 | 0 | 0 | 0 | 0 | 1 | 1 | 1 | 1 | 1 | 1 |
| | 156 | 0 | 0 | 0 | 0 | 0 | 0 | 0 | 0 | 0 | 0 | 0 | 0 | 0 | 0 | 0 | 0 |
| | 166 | 0 | 0 | 0 | 0 | 0 | 0 | 0 | 0 | 0 | 0 | 0 | 0 | 0 | 0 | 0 | 0 |
| | Avg. | 0.7 | 0.7 | 6 | 0 | 0 | 0 | 0 | 0 | 0 | 0 | 0.2 | 0.2 | 0.2 | 0.2 | 0.2 | 0.2 |

| Treatment | Sow # | −3 | −2 | −1 | 0 | 1 | 2 | 3 | 4 | 5 | 6 | 7 | 8 | 9 | 10 | 11 | 12 |
|---|---|---|---|---|---|---|---|---|---|---|---|---|---|---|---|---|---|
| Group D JA-142 Pass 4 | 2 | 0 | 0 | 0 | 0 | 0 | 0 | 0 | 0 | 0 | 1 | 1 | 1 | 1 | 1 | 1 | 1 |
| | 106 | 0 | 0 | 0 | 0 | 0 | 0 | 0 | 0 | 0 | 0 | 1 | 1 | 1 | 1 | 1 | 1 |
| | 159 | 0 | 0 | 0 | 0 | 0 | 0 | 0 | 0 | 0 | 3 | 1 | 1 | 1 | 1 | 1 | 1 |
| | 190 | 0 | 0 | 0 | 0 | 0 | 0 | 0 | 0 | 0 | 0 | 0 | 0 | 1 | 1 | 1 | 1 |
| | 206 | 0 | 0 | 0 | 0 | 0 | 0 | 0 | 0 | 0 | 0 | 1 | 1 | 0 | 0 | 0 | 0 |
| | 232 | 0 | 0 | 0 | 0 | 0 | 0 | 0 | 0 | 0 | 0 | 0 | 0 | 0 | 0 | 0 | 0 |
| | 234 | 0 | 0 | 0 | 0 | 0 | 0 | 0 | 0 | 0 | 0 | 0 | 0 | 0 | 1 | 1 | 1 |
| | Avg. | 0 | 0 | 0 | 0 | 0 | 0 | 0 | 0 | 0 | 0.6 | 0.6 | 0.6 | 0.6 | 0.7 | 0.7 | 0.7 |

| | | 13 | 14 | 15 | 16 | 17 | 18 | 19 | 20 | 21 | 22 | 23 | 24 | 25 | 26 | 27 | 28 |
|---|---|---|---|---|---|---|---|---|---|---|---|---|---|---|---|---|---|
| Group D JA-142 Pass 4 | 2 | 1 | 1 | 3 | 3 | 1 | 0 | 0 | 0 | 0 | 0 | 0 | 0 | 0 | 0 | 0 | 0 |
| | 106 | 0 | 0 | 0 | 0 | 0 | 0 | 0 | 0 | 0 | 0 | 0 | 0 | 0 | 0 | 0 | 0 |
| | 159 | 1 | 1 | 1 | 1 | 3 | 4 | 2 | 3 | 3 | 3 | 2 | 0 | 0 | 2 | 0 | 0 |
| | 190 | 1 | 2 | 0 | 0 | 0 | 0 | 0 | 0 | 0 | 0 | 0 | 0 | 0 | 0 | 0 | 0 |
| | 206 | 0 | 0 | 0 | 0 | 0 | 0 | 0 | 0 | 0 | 0 | 0 | 0 | 0 | 0 | 0 | 0 |
| | 232 | 0 | 0 | 0 | 0 | 0 | 0 | 0 | 0 | 0 | 0 | 0 | 0 | 0 | 0 | 0 | 0 |
| | 234 | 0 | 2 | 0 | 0 | 0 | 0 | 0 | 0 | 0 | 0 | 0 | 0 | 0 | 0 | 0 | 0 |
| | Avg. | 0.4 | 0.3 | 0.6 | 0.6 | 0.6 | 0.6 | 0.3 | 0.4 | 0.4 | 0.4 | 0.3 | 0 | 0 | 0.3 | 0 | 0 |

| | | 29 | 30 | 31 | 32 | 33 | 34 | 35 | 36 | 37 | 38 |
|---|---|---|---|---|---|---|---|---|---|---|---|
| Group D JA-142 Pass 4 | 2 | 0 | 0 | 0 | 1 | 1 | 1 | 3 | 3 | 1 | 1 |
| | 106 | 0 | 0 | 0 | 0 | 0 | 0 | 0 | 0 | 0 | 0 |
| | 159 | 0 | 0 | 0 | 0 | 0 | 0 | 0 | 0 | 0 | 0 |
| | 190 | 0 | 0 | 0 | 0 | 0 | 0 | 0 | 0 | 0 | 0 |
| | 206 | 0 | 0 | 0 | 0 | 0 | 0 | 0 | 0 | 0 | 0 |
| | 232 | 0 | 0 | 0 | 0 | 0 | 0 | 0 | 0 | 0 | 0 |
| | 234 | 0 | 0 | 0 | 0 | 0 | 0 | 0 | 0 | 0 | 0 |
| | Avg. | 0 | 0 | 0 | 0.1 | 0.1 | 0.1 | 0.4 | 0.4 | 0.1 | 0.1 |

Clinical observations of the piglets fell into two major categories, death and reduced appetite. There were no significant differences between groups A, B and C in the area of average deaths per litter (DPL). Group A had an average of 1.3 DPL, group B had an average of 2.4 DPL, group C had an average of 2.0 DPL, and no pigs from group D survived beyond three days post farrowing. Clinical scores for the piglets are given in Table 3.

TABLE 3

| Treatment | Sow # | Pig # | 1 | 2 | 3 | 4 | 5 | 6 | 7 | 8 | 9 | 10 | 11 | 12 | 13 | 14 |
|---|---|---|---|---|---|---|---|---|---|---|---|---|---|---|---|---|
| Group A JA-142 Pass 200 | 98 | 813 | 0 | 0 | 1 | 30 | | | | | | | | | | |
| | | 814 | 0 | 0 | 0 | 0 | 0 | 0 | 0 | 0 | 0 | 0 | 0 | 0 | 0 | 0 |
| | | 815 | 0 | 0 | 0 | 0 | 0 | 0 | 0 | 0 | 0 | 0 | 0 | 0 | 0 | 0 |
| | | 816 | 0 | 0 | 0 | 0 | 0 | 0 | 0 | 0 | 0 | 0 | 0 | 0 | 0 | 0 |
| | | 817 | 1 | 0 | 1 | 0 | 0 | 0 | 0 | 0 | 0 | 0 | 0 | 0 | 0 | 0 |
| | | 818 | 0 | 0 | 0 | 0 | 0 | 0 | 0 | 0 | 0 | 0 | 0 | 0 | 0 | 0 |
| | | 819 | 0 | 0 | 0 | 0 | 0 | 0 | 0 | 0 | 0 | 0 | 0 | 0 | 0 | 0 |
| | | 820 | 0 | 0 | 0 | 0 | 0 | 0 | 0 | 0 | 0 | 0 | 0 | 0 | 0 | 0 |
| | | 821 | 1 | 0 | 0 | 0 | 0 | 0 | 0 | 0 | 0 | 0 | 0 | 0 | 0 | 0 |
| | | 822 | 1 | 30 | | | | | | | | | | | | |
| | | Avg. | 0.3 | 3 | 0.2 | 3.3 | 0 | 0 | 0 | 0 | 0 | 0 | 0 | 0 | 0 | 0 |
| | 133 | 720 | 30 | | | | | | | | | | | | | |
| | | 721 | 0 | 1 | 0 | 0 | 0 | 0 | 0 | 0 | 0 | 0 | 0 | 0 | 0 | 0 |
| | | 722 | 0 | 0 | 0 | 1 | 0 | 0 | 0 | 0 | 0 | 0 | 0 | 0 | 0 | 0 |
| | | 723 | 0 | 0 | 0 | 0 | 0 | 0 | 0 | 0 | 0 | 0 | 0 | 0 | 0 | 0 |
| | | 724 | 0 | 1 | 0 | 0 | 0 | 1 | 0 | 0 | 0 | 0 | 0 | 0 | 0 | 0 |
| | | 725 | 0 | 0 | 0 | 0 | 0 | 0 | 0 | 0 | 0 | 0 | 0 | 0 | 0 | 0 |
| | | 798 | 0 | 0 | 0 | 0 | 0 | 0 | 0 | 0 | 0 | 0 | 0 | 0 | 0 | 0 |
| | | 799 | 30 | | | | | | | | | | | | | |
| | | 800 | 0 | 0 | 0 | 0 | 0 | 0 | 0 | 0 | 0 | 0 | 0 | 0 | 0 | 0 |
| | | 807 | 0 | 0 | 0 | 0 | 0 | 0 | 0 | 0 | 0 | 0 | 0 | 1 | 0 | 0 |
| | | 809 | 0 | 0 | 0 | 0 | 0 | 0 | 0 | 0 | 0 | 0 | 0 | 0 | 0 | 0 |
| | | 810 | 0 | 0 | 0 | 0 | 0 | 0 | 0 | 0 | 0 | 0 | 0 | 0 | 0 | 0 |
| | | 812 | 0 | 0 | 0 | 0 | 0 | 0 | 0 | 0 | 0 | 0 | 0 | 0 | 0 | 0 |
| | | Avg. | 4.6 | 0.2 | 0 | 0.1 | 0 | 0.1 | 0 | 0 | 0 | 0 | 0 | 0.1 | 0 | 0 |
| | 147 | 823 | 0 | 0 | 0 | 0 | 0 | 0 | 0 | 0 | 0 | 0 | 0 | 0 | 0 | 0 |
| | | 824 | 0 | 0 | 0 | 0 | 0 | 0 | 0 | 3 | 1 | 1 | 1 | 1 | 1 | 1 |
| | | 825 | 0 | 0 | 0 | 0 | 0 | 0 | 0 | 0 | 0 | 0 | 0 | 0 | 0 | 0 |
| | | 845 | 0 | 0 | 0 | 0 | 0 | 0 | 0 | 0 | 0 | 0 | 0 | 0 | 0 | 0 |
| | | 846 | 0 | 0 | 0 | 0 | 0 | 0 | 0 | 0 | 0 | 0 | 0 | 0 | 0 | 0 |
| | | 847 | 0 | 0 | 0 | 0 | 0 | 0 | 0 | 0 | 0 | 0 | 0 | 0 | 0 | 0 |
| | | 848 | 0 | 0 | 0 | 0 | 0 | 0 | 1 | 0 | 0 | 0 | 0 | 0 | 0 | 0 |
| | | 849 | 0 | 0 | 0 | 0 | 0 | 0 | 0 | 0 | 0 | 0 | 0 | 0 | 0 | 2 |
| | | 850 | 30 | | | | | | | | | | | | | |
| | | 976 | 0 | 0 | 0 | 0 | 0 | 0 | 0 | 0 | 0 | 0 | 0 | 0 | 0 | 0 |
| | | 977 | 0 | 0 | 0 | 0 | 1 | 1 | 3 | 30 | | | | | | |
| | | 978 | 30 | | | | | | | | | | | | | |
| | | Avg. | 5 | 0 | 0 | 0 | 0.1 | 0.1 | 0.4 | 3.3 | 0.1 | 0.1 | 0.1 | 0.1 | 0.1 | 0.3 |
| | 178 | 486 | 30 | | | | | | | | | | | | | |
| | | 487 | 0 | 0 | 0 | 0 | 0 | 0 | 0 | 0 | 0 | 0 | 0 | 1 | 0 | 0 |
| | | 488 | 0 | 0 | 0 | 0 | 0 | 0 | 0 | 0 | 0 | 0 | 0 | 0 | 0 | 0 |
| | | 489 | 0 | 0 | 0 | 0 | 0 | 0 | 0 | 0 | 0 | 0 | 0 | 0 | 0 | 0 |
| | | 490 | 0 | 0 | 0 | 0 | 0 | 0 | 0 | 0 | 0 | 0 | 0 | 0 | 0 | 0 |
| | | 491 | 0 | 0 | 0 | 0 | 0 | 0 | 0 | 0 | 0 | 0 | 0 | 0 | 0 | 0 |
| | | 492 | 0 | 0 | 0 | 0 | 0 | 0 | 0 | 0 | 0 | 0 | 0 | 0 | 0 | 0 |
| | | 493 | 0 | 0 | 0 | 0 | 0 | 0 | 0 | 0 | 0 | 0 | 0 | 0 | 0 | 0 |
| | | 494 | 0 | 1 | 0 | 0 | 0 | 0 | 0 | 0 | 0 | 0 | 0 | 0 | 0 | 0 |
| | | Avg. | 3.3 | 0.1 | 0 | 0 | 0 | 0 | 0 | 0 | 0 | 0 | 0 | 0.1 | 0 | 0 |
| Group A JA-142 Pass 200 | 215 | 495 | 0 | 0 | 0 | 0 | 0 | 0 | 0 | 0 | 0 | 0 | 0 | 0 | 0 | 0 |
| | | 496 | 0 | 0 | 0 | 0 | 0 | 0 | 0 | 0 | 0 | 0 | 0 | 0 | 0 | 0 |
| | | 497 | 0 | 0 | 0 | 0 | 0 | 0 | 0 | 0 | 0 | 0 | 0 | 0 | 0 | 0 |
| | | 498 | 0 | 0 | 0 | 0 | 0 | 0 | 0 | 0 | 0 | 0 | 0 | 0 | 0 | 0 |
| | | 499 | 0 | 0 | 0 | 0 | 0 | 0 | 0 | 0 | 0 | 0 | 0 | 0 | 0 | 0 |
| | | 500 | 0 | 0 | 0 | 0 | 0 | 0 | 0 | 0 | 0 | 0 | 0 | 0 | 0 | 0 |
| | | 808 | 0 | 0 | 0 | 0 | 0 | 0 | 0 | 0 | 0 | 0 | 0 | 0 | 0 | 0 |
| | | Avg. | 0 | 0 | 0 | 0 | 0 | 0 | 0 | 0 | 0 | 0 | 0 | 0 | 0 | 0 |
| | 233 | 476 | 0 | 0 | 0 | 0 | 0 | 0 | 0 | 0 | 0 | 0 | 0 | 0 | 0 | 0 |
| | | 477 | 0 | 0 | 0 | 0 | 0 | 0 | 0 | 0 | 0 | 0 | 0 | 0 | 0 | 0 |
| | | 478 | 0 | 0 | 0 | 0 | 0 | 0 | 0 | 0 | 0 | 0 | 0 | 0 | 0 | 0 |
| | | 478 | 0 | 0 | 0 | 0 | 0 | 0 | 0 | 0 | 0 | 0 | 0 | 0 | 0 | 0 |
| | | 480 | 0 | 0 | 0 | 0 | 0 | 0 | 0 | 0 | 0 | 0 | 0 | 0 | 0 | 0 |
| | | 481 | 0 | 0 | 0 | 0 | 0 | 0 | 0 | 0 | 0 | 0 | 0 | 0 | 0 | 0 |
| | | 482 | 0 | 0 | 0 | 0 | 0 | 0 | 0 | 0 | 0 | 0 | 0 | 0 | 0 | 0 |
| | | 483 | 0 | 0 | 0 | 0 | 0 | 0 | 0 | 0 | 0 | 0 | 0 | 0 | 0 | 0 |
| | | 484 | 0 | 0 | 0 | 0 | 0 | 0 | 0 | 0 | 0 | 0 | 0 | 0 | 0 | 0 |
| | | 485 | 0 | 0 | 0 | 0 | 0 | 0 | 0 | 0 | 0 | 0 | 0 | 0 | 0 | 0 |
| | | Avg. | 0 | 0 | 0 | 0 | 0 | 0 | 0 | 0 | 0 | 0 | 0 | 0 | 0 | 0 |
| | 243 | 707 | 0 | 0 | 0 | 0 | 0 | 0 | 0 | 0 | 0 | 0 | 0 | 0 | 0 | 0 |
| | | 708 | 0 | 0 | 0 | 0 | 0 | 0 | 0 | 0 | 0 | 0 | 0 | 0 | 0 | 0 |
| | | 709 | 0 | 0 | 0 | 0 | 0 | 0 | 0 | 0 | 0 | 0 | 0 | 0 | 0 | 0 |
| | | 710 | 0 | 0 | 0 | 0 | 0 | 0 | 0 | 0 | 0 | 0 | 0 | 0 | 0 | 0 |

TABLE 3-continued

| Treatment | Sow # | Pig # | 1 | 2 | 3 | 4 | 5 | 6 | 7 | 8 | 9 | 10 | 11 | 12 | 13 | 14 |
|---|---|---|---|---|---|---|---|---|---|---|---|---|---|---|---|---|
| | | 711 | 0 | 0 | 0 | 0 | 0 | 0 | 0 | 0 | 0 | 0 | 0 | 0 | 0 | 0 |
| | | 712 | 0 | 0 | 0 | 0 | 0 | 0 | 0 | 0 | 0 | 0 | 0 | 0 | 0 | 0 |
| | | 713 | 0 | 0 | 0 | 0 | 0 | 0 | 0 | 0 | 0 | 1 | 30 | | | |
| | | 714 | 0 | 0 | 0 | 0 | 0 | 0 | 0 | 0 | 0 | 0 | 0 | 0 | 0 | 0 |
| | | 715 | 0 | 0 | 0 | 0 | 0 | 0 | 0 | 0 | 0 | 0 | 0 | 0 | 0 | 0 |
| | | 716 | 0 | 0 | 0 | 0 | 0 | 0 | 0 | 0 | 0 | 0 | 0 | 0 | 0 | 0 |
| | | 717 | 0 | 0 | 0 | 0 | 0 | 0 | 0 | 0 | 0 | 0 | 0 | 1 | 0 | 0 |
| | | 718 | 0 | 0 | 0 | 0 | 0 | 0 | 0 | 0 | 0 | 0 | 0 | 1 | 0 | 0 |
| | | 719 | 0 | 0 | 0 | 0 | 0 | 0 | 0 | 0 | 0 | 0 | 0 | 0 | 0 | 0 |
| | | Avg. | 0 | 0 | 0 | 0 | 0 | 0 | 0 | 0 | 0 | 0.1 | 2.3 | 0.2 | 0 | 0 |
| Group B Backpassage 6 | 49 | 430 | 0 | 0 | 0 | 0 | 0 | 0 | 0 | 0 | 0 | 0 | 0 | 0 | 0 | 0 |
| | | 431 | 0 | 0 | 0 | 0 | 0 | 0 | 0 | 0 | 0 | 0 | 0 | 0 | 0 | 0 |
| | | 432 | 0 | 0 | 0 | 0 | 0 | 0 | 0 | 0 | 0 | 0 | 0 | 0 | 0 | 0 |
| | | 433 | 0 | 0 | 0 | 0 | 0 | 0 | 0 | 0 | 0 | 0 | 0 | 0 | 0 | 0 |
| | | 434 | 0 | 0 | 0 | 0 | 0 | 0 | 0 | 0 | 0 | 0 | 0 | 0 | 0 | 0 |
| | | 435 | 0 | 0 | 0 | 0 | 0 | 0 | 0 | 0 | 0 | 0 | 0 | 0 | 0 | 0 |
| | | 436 | 0 | 0 | 0 | 0 | 0 | 0 | 0 | 0 | 0 | 0 | 0 | 0 | 0 | 0 |
| | | 437 | 0 | 0 | 0 | 0 | 0 | 0 | 0 | 0 | 0 | 0 | 0 | 0 | 0 | 0 |
| | | 438 | 30 | 0 | 0 | 0 | 0 | 0 | 0 | 0 | 0 | 0 | 0 | 0 | 0 | 0 |
| | | Avg. | 3.3 | 0 | 0 | 0 | 0 | 0 | 0 | 0 | 0 | 0 | 0 | 0 | 0 | 0 |
| | 100 | 459 | 0 | 0 | 0 | 0 | 0 | 0 | 0 | 0 | 0 | 0 | 0 | 0 | 0 | 0 |
| | | 460 | 0 | 0 | 0 | 0 | 0 | 0 | 0 | 0 | 0 | 0 | 0 | 0 | 0 | 0 |
| | | 461 | 0 | 0 | 0 | 0 | 0 | 0 | 1 | 1 | 1 | 0 | 0 | 0 | 0 | 0 |
| | | 462 | 0 | 0 | 0 | 0 | 1 | 1 | 1 | 1 | 1 | 1 | 1 | 1 | 1 | 1 |
| | | 463 | 0 | 0 | 0 | 0 | 0 | 0 | 0 | 0 | 0 | 0 | 0 | 0 | 0 | 0 |
| | | 464 | 0 | 0 | 1 | 1 | 1 | 1 | 30 | | | | | | | |
| | | 465 | 0 | 30 | | | | | | | | | | | | |
| | | Avg. | 0 | 4.3 | 0.2 | 0.2 | 0.3 | 0.3 | 5.3 | 0.4 | 0.4 | 0.2 | 0.2 | 0.2 | 0.2 | 0.2 |
| | 135 | 439 | 0 | 0 | 0 | 0 | 0 | 0 | 0 | 30 | | | | | | |
| | | 440 | 0 | 0 | 0 | 0 | 0 | 0 | 0 | 0 | 0 | 0 | 0 | 0 | 0 | 0 |
| | | 441 | 0 | 0 | 0 | 0 | 0 | 0 | 0 | 0 | 0 | 0 | 0 | 0 | 0 | 0 |
| | | 442 | 0 | 0 | 0 | 1 | 1 | 1 | 1 | 1 | 1 | 1 | 3 | 3 | 3 | 30 |
| | | 443 | 0 | 0 | 0 | 0 | 0 | 0 | 0 | 0 | 0 | 0 | 0 | 0 | 0 | 0 |
| | | 444 | 0 | 0 | 0 | 0 | 0 | 0 | 1 | 1 | 0 | 0 | 0 | 0 | 0 | 0 |
| | | 445 | 0 | 0 | 0 | 0 | 0 | 0 | 0 | 0 | 0 | 0 | 0 | 0 | 0 | 0 |
| | | 446 | 0 | 0 | 0 | 0 | 0 | 0 | 0 | 0 | 0 | 0 | 0 | 0 | 0 | 0 |
| | | 447 | 0 | 0 | 0 | 0 | 0 | 0 | 0 | 0 | 0 | 0 | 0 | 0 | 0 | 0 |
| | | Avg. | 0 | 0 | 0 | 0.1 | 0.1 | 0.1 | 0.2 | 3.6 | 0.1 | 0.1 | 0.4 | 0.4 | 0.4 | 3.8 |
| | 149 | 231 | 0 | 0 | 0 | 0 | 0 | 0 | 0 | 0 | 0 | 0 | 0 | 0 | 0 | 0 |
| | | 232 | 0 | 0 | 0 | 0 | 0 | 0 | 0 | 0 | 0 | 0 | 0 | 0 | 0 | 0 |
| | | 233 | 0 | 0 | 0 | 0 | 0 | 0 | 30 | | | | | | | |
| | | 234 | 0 | 0 | 0 | 0 | 0 | 0 | 3 | 1 | 1 | 3 | 1 | 1 | 1 | 1 |
| | | 235 | 0 | 0 | 0 | 0 | 0 | 0 | 3 | 2 | 3 | 3 | 0 | 0 | 0 | 0 |
| | | 236 | 0 | 0 | 0 | 0 | 0 | 0 | 0 | 0 | 0 | 0 | 0 | 0 | 0 | 0 |
| | | 237 | 0 | 0 | 0 | 0 | 0 | 0 | 1 | 1 | 1 | 1 | 1 | 1 | 1 | 1 |
| | | 238 | 0 | 0 | 0 | 0 | 0 | 2 | 0 | 0 | 0 | 0 | 0 | 0 | 0 | 0 |
| | | 239 | 0 | 0 | 30 | | | | | | | | | | | |
| | | 240 | 30 | | | | | | | | | | | | | |
| | | 241 | 3 | 30 | | | | | | | | | | | | |
| | | 242 | 0 | 0 | 0 | 0 | 0 | 2 | 3 | 3 | 30 | | | | | |
| | | Avg. | 2.8 | 2.7 | 3 | 0 | 0 | 0.4 | 4.4 | 0.9 | 4.4 | 1 | 0.3 | 0.3 | 0.3 | 0.3 |
| Group B Backpassage 6 | 209 | 448 | 0 | 0 | 0 | 0 | 0 | 0 | 0 | 0 | 0 | 0 | 0 | 0 | 0 | 0 |
| | | 449 | 0 | 0 | 0 | 0 | 0 | 0 | 0 | 0 | 0 | 0 | 0 | 0 | 0 | 0 |
| | | 450 | 0 | 0 | 0 | 0 | 0 | 0 | 0 | 0 | 0 | 0 | 0 | 0 | 0 | 0 |
| | | 451 | 0 | 0 | 0 | 0 | 0 | 0 | 0 | 0 | 1 | 1 | 1 | 1 | 1 | 1 |
| | | 452 | 0 | 0 | 0 | 0 | 0 | 0 | 0 | 0 | 0 | 0 | 0 | 0 | 0 | 0 |
| | | 453 | 0 | 0 | 0 | 0 | 0 | 0 | 0 | 0 | 0 | 0 | 0 | 0 | 0 | 0 |
| | | 454 | 0 | 0 | 0 | 0 | 0 | 0 | 0 | 0 | 1 | 1 | 1 | 1 | 1 | 1 |
| | | 455 | 0 | 0 | 0 | 0 | 0 | 0 | 0 | 0 | 0 | 1 | 1 | 1 | 1 | 1 |
| | | 456 | 30 | | | | | | | | | | | | | |
| | | 457 | 0 | 0 | 0 | 0 | 0 | 0 | 0 | 0 | 2 | 1 | 1 | 1 | 1 | 1 |
| | | 458 | 30 | | | | | | | | | | | | | |
| | | Avg. | 5.5 | 0 | 0 | 0 | 0 | 0 | 0 | 0 | 0.4 | 0.4 | 0.4 | 0.4 | 0.4 | 0.4 |
| | 212 | 243 | 0 | 0 | 0 | 0 | 0 | 0 | 0 | 0 | 0 | 0 | 0 | 0 | 0 | 0 |
| | | 244 | 0 | 0 | 0 | 0 | 0 | 0 | 0 | 0 | 0 | 0 | 0 | 0 | 0 | 0 |
| | | 245 | 0 | 0 | 0 | 0 | 3 | 1 | 30 | | | | | | | |
| | | 246 | 0 | 0 | 0 | 0 | 0 | 0 | 0 | 0 | 0 | 0 | 0 | 0 | 0 | 0 |
| | | 247 | 0 | 0 | 0 | 0 | 0 | 2 | 2 | 0 | 0 | 0 | 0 | 0 | 0 | 0 |
| | | 248 | 0 | 0 | 0 | 0 | 2 | 0 | 0 | 0 | 0 | 0 | 0 | 0 | 0 | 0 |
| | | 249 | 0 | 0 | 0 | 0 | 0 | 0 | 2 | 2 | 0 | 0 | 2 | 0 | 0 | 0 |
| | | 250 | 0 | 0 | 0 | 3 | 30 | | | | | | | | | |
| | | 426 | 0 | 0 | 0 | 0 | 0 | 0 | 0 | 0 | 0 | 0 | 0 | 0 | 0 | 0 |
| | | 427 | 0 | 0 | 0 | 1 | 3 | 1 | 1 | 30 | | | | | | |
| | | 428 | 0 | 0 | 0 | 1 | 3 | 3 | 30 | | | | | | | |
| | | 429 | 0 | 0 | 0 | 0 | 2 | 3 | 3 | 3 | 3 | 3 | 3 | 1 | 30 | |
| | | Avg. | 0 | 0 | 0 | 0.4 | 3.6 | 0.9 | 6.2 | 3.9 | 0.4 | 0.4 | 0.6 | 0.1 | 3.8 | 0 |

TABLE 3-continued

| Treatment | Sow # | Pig # | 1 | 2 | 3 | 4 | 5 | 6 | 7 | 8 | 9 | 10 | 11 | 12 | 13 | 14 |
|---|---|---|---|---|---|---|---|---|---|---|---|---|---|---|---|---|
| | | 226 | Not Preg. | | | | | | | | | | | | | |
| Group C Sterile Diluent | 58 | 24 | 0 | 0 | 0 | 0 | 0 | 0 | 0 | 0 | 0 | 0 | 0 | 0 | 0 | 0 |
| | | 25 | 0 | 0 | 0 | 0 | 0 | 0 | 0 | 0 | 0 | 0 | 0 | 0 | 0 | 0 |
| | | 46 | 0 | 0 | 0 | 0 | 0 | 0 | 0 | 0 | 0 | 0 | 0 | 0 | 0 | 0 |
| | | 47 | 0 | 0 | 0 | 0 | 0 | 0 | 0 | 0 | 0 | 0 | 0 | 0 | 0 | 0 |
| | | 48 | 0 | 0 | 0 | 0 | 0 | 0 | 0 | 0 | 0 | 0 | 0 | 0 | 0 | 0 |
| | | 49 | 0 | 0 | 0 | 0 | 0 | 0 | 0 | 0 | 0 | 0 | 0 | 0 | 0 | 0 |
| | | 50 | 0 | 0 | 0 | 0 | 0 | 0 | 0 | 0 | 0 | 0 | 0 | 0 | 0 | 0 |
| | | 51 | 0 | 0 | 0 | 2 | 2 | 1 | 1 | 1 | 30 | | | | | |
| | | Avg. | 0 | 0 | 0 | 0.3 | 0.3 | 0.1 | 0.1 | 0.1 | 3.8 | 0 | 0 | 0 | 0 | 0 |
| | 113 | 17 | 30 | | | | | | | | | | | | | |
| | | 18 | 30 | | | | | | | | | | | | | |
| | | 19 | 30 | | | | | | | | | | | | | |
| | | 20 | 30 | | | | | | | | | | | | | |
| | | 21 | 0 | 30 | | | | | | | | | | | | |
| | | 22 | 30 | | | | | | | | | | | | | |
| | | 23 | 30 | | | | | | | | | | | | | |
| | | Avg. | 25.7 | 30 | | | | | | | | | | | | |
| | 117 | 52 | 1 | 0 | 0 | 0 | 0 | 0 | 0 | 0 | 0 | 0 | 0 | 0 | 0 | 0 |
| | | 53 | 0 | 0 | 0 | 0 | 0 | 0 | 0 | 0 | 0 | 0 | 0 | 0 | 0 | 0 |
| | | 54 | 0 | 0 | 0 | 0 | 0 | 0 | 0 | 0 | 0 | 0 | 0 | 0 | 0 | 0 |
| | | 55 | 0 | 0 | 0 | 0 | 0 | 0 | 0 | 0 | 0 | 0 | 0 | 0 | 0 | 0 |
| | | 56 | 1 | 0 | 0 | 0 | 30 | | | | | | | | | |
| | | 57 | 1 | 0 | 0 | 0 | 0 | 0 | 0 | 0 | 0 | 0 | 0 | 0 | 0 | 0 |
| | | 58 | 0 | 0 | 0 | 0 | 0 | 0 | 0 | 0 | 0 | 0 | 0 | 0 | 0 | 0 |
| | | 59 | 0 | 0 | 0 | 0 | 0 | 0 | 0 | 0 | 0 | 0 | 0 | 0 | 0 | 0 |
| | | 60 | 0 | 0 | 0 | 0 | 0 | 0 | 0 | 0 | 0 | 0 | 0 | 1 | 0 | 0 |
| | | 61 | 1 | 0 | 0 | 0 | 0 | 0 | 0 | 0 | 1 | 1 | 1 | 0 | 0 | 0 |
| | | 62 | 1 | 0 | 0 | 0 | 0 | 0 | 0 | 0 | 0 | 0 | 0 | 0 | 0 | 0 |
| | | Avg. | 0.5 | 0 | 0 | 0 | 2.7 | 0 | 0 | 0 | 0.1 | 0.1 | 0.1 | 0.1 | 0 | 0 |
| | 144 | 146 | 0 | 0 | 0 | 0 | 0 | 0 | 0 | 0 | 0 | 0 | 0 | 0 | 0 | 0 |
| | | 147 | 0 | 0 | 0 | 0 | 0 | 0 | 0 | 0 | 0 | 0 | 0 | 0 | 0 | 0 |
| | | 148 | 0 | 0 | 0 | 0 | 0 | 0 | 0 | 0 | 0 | 0 | 0 | 0 | 0 | 0 |
| | | 149 | 0 | 0 | 0 | 0 | 0 | 0 | 0 | 0 | 0 | 0 | 0 | 0 | 0 | 0 |
| | | 150 | 0 | 0 | 0 | 0 | 0 | 0 | 0 | 0 | 1 | 0 | 1 | 1 | 1 | 0 |
| | | 221 | 0 | 0 | 0 | 0 | 0 | 2 | 2 | 0 | 0 | 0 | 0 | 0 | 0 | 0 |
| | | 222 | 0 | 0 | 0 | 0 | 0 | 2 | 2 | 1 | 1 | 1 | 1 | 1 | 0 | 1 |
| | | 223 | 0 | 0 | 0 | 0 | 0 | 0 | 0 | 0 | 0 | 0 | 0 | 0 | 0 | 0 |
| | | 224 | 0 | 0 | 0 | 0 | 0 | 0 | 0 | 0 | 0 | 0 | 0 | 0 | 0 | 0 |
| | | 225 | 0 | 0 | 0 | 0 | 0 | 0 | 0 | 0 | 0 | 0 | 0 | 0 | 0 | 0 |
| | | 970 | 0 | 0 | 0 | 0 | 0 | 0 | 0 | 0 | 0 | 0 | 0 | 0 | 0 | 0 |
| | | 971 | 0 | 0 | 0 | 0 | 0 | 0 | 0 | 0 | 0 | 0 | 0 | 0 | 0 | 0 |
| | | Avg. | 0 | 0 | 0 | 0 | 0 | 0.3 | 0.3 | 0.1 | 0.2 | 0.1 | 0.2 | 0.2 | 0.1 | 0.1 |
| Group C Sterile Diluent | 156 | 63 | 0 | 0 | 0 | 0 | 0 | 0 | 0 | 0 | 0 | 0 | 0 | 0 | 0 | 0 |
| | | 64 | 0 | 0 | 1 | 0 | 30 | | | | | | | | | |
| | | 65 | 0 | 0 | 0 | 0 | 0 | 0 | 0 | 1 | 1 | 1 | 1 | 1 | 0 | 0 |
| | | 66 | 0 | 0 | 0 | 0 | 1 | 0 | 0 | 0 | 0 | 0 | 0 | 0 | 0 | 0 |
| | | 67 | 0 | 0 | 0 | 0 | 1 | 0 | 1 | 1 | 30 | | | | | |
| | | 68 | 0 | 0 | 0 | 0 | 0 | 0 | 0 | 0 | 0 | 0 | 0 | 0 | 0 | 0 |
| | | 69 | 0 | 0 | 0 | 0 | 0 | 0 | 0 | 1 | 0 | 0 | 0 | 0 | 0 | 0 |
| | | 70 | 0 | 0 | 0 | 0 | 0 | 0 | 0 | 0 | 0 | 0 | 0 | 0 | 0 | 0 |
| | | 71 | 0 | 0 | 0 | 0 | 0 | 2 | 2 | 0 | 0 | 0 | 0 | 0 | 1 | 0 |
| | | 72 | 0 | 0 | 0 | 0 | 0 | 0 | 0 | 0 | 0 | 0 | 0 | 0 | 0 | 0 |
| | | 73 | 0 | 0 | 0 | 0 | 0 | 0 | 0 | 0 | 0 | 0 | 0 | 0 | 0 | 0 |
| | | 74 | 0 | 0 | 0 | 0 | 1 | 0 | 0 | 0 | 0 | 0 | 0 | 0 | 0 | 0 |
| | | 75 | 0 | 0 | 0 | 0 | 0 | 0 | 0 | 0 | 0 | 0 | 0 | 0 | 0 | 0 |
| | | Avg. | 0 | 0 | 0.1 | 0 | 2.5 | 0.2 | 0.3 | 0.3 | 2.6 | 0.1 | 0.1 | 0.1 | 0.1 | 0 |
| | 166 | 76 | 0 | 0 | 0 | 0 | 0 | 0 | 0 | 0 | 0 | 0 | 0 | 0 | 0 | 0 |
| | | 77 | 0 | 0 | 0 | 0 | 0 | 0 | 0 | 0 | 0 | 0 | 0 | 0 | 0 | 0 |
| | | 78 | 0 | 0 | 0 | 0 | 0 | 0 | 0 | 0 | 0 | 0 | 0 | 0 | 0 | 0 |
| | | 79 | 0 | 0 | 0 | 0 | 0 | 0 | 0 | 0 | 0 | 0 | 0 | 0 | 0 | 0 |
| | | 80 | 0 | 0 | 0 | 0 | 0 | 0 | 0 | 0 | 0 | 0 | 0 | 0 | 0 | 0 |
| | | 81 | 1 | 0 | 0 | 0 | 0 | 0 | 0 | 0 | 0 | 0 | 0 | 0 | 0 | 0 |
| | | 141 | 0 | 0 | 0 | 0 | 0 | 0 | 0 | 0 | 0 | 0 | 0 | 0 | 0 | 0 |
| | | 142 | 0 | 0 | 0 | 0 | 0 | 0 | 0 | 0 | 0 | 0 | 0 | 0 | 0 | 0 |
| | | 143 | 0 | 0 | 0 | 0 | 0 | 0 | 0 | 0 | 0 | 0 | 0 | 0 | 0 | 0 |
| | | 144 | 0 | 0 | 0 | 0 | 0 | 0 | 0 | 0 | 0 | 0 | 0 | 0 | 0 | 0 |
| | | 145 | 1 | 30 | | | | | | | | | | | | |
| | | Avg. | 0.2 | 2.7 | 0 | 0 | 0 | 0 | 0 | 0 | 0 | 0 | 0 | 0 | 0 | 0 |
| Group D JA-142 Passage 4 | 2 | 891 | 1 | 3 | 30 | | | | | | | | | | | |
| | | 892 | 1 | 30 | | | | | | | | | | | | |
| | | Avg. | 1 | 16.5 | 30 | | | | | | | | | | | |
| | 106 | Aborted | NA | | | | | | | | | | | | | |
| | 159 | 883 | 30 | | | | | | | | | | | | | |

TABLE 3-continued

| Treatment | Sow # | Pig # | 1 | 2 | 3 | 4 | 5 | 6 | 7 | 8 | 9 | 10 | 11 | 12 | 13 | 14 |
|---|---|---|---|---|---|---|---|---|---|---|---|---|---|---|---|---|
| | | 884 | 30 | | | | | | | | | | | | | |
| | | Avg. | 30 | | | | | | | | | | | | | |
| | 190 | Aborted | NA | | | | | | | | | | | | | |
| | 206 | 890 | 30 | | | | | | | | | | | | | |
| | | Avg. | 30 | | | | | | | | | | | | | |
| | 232 | 888 | 30 | | | | | | | | | | | | | |
| | | 889 | 30 | | | | | | | | | | | | | |
| | | Avg. | 30 | | | | | | | | | | | | | |
| | 234 | Aborted | NA | | | | | | | | | | | | | |

The farrowing performance results provided the most dramatic differences and similarities between the various treatment groups. Since the treatments would not have an effect on the size of the litters, the most appropriate way to compare the farrowing results would be by using percentage values. Group A had an average percentage of live/born of 85% (SD+/−9.6). Group B had an average percentage of live/born of 89% (SD+/−11.6). The control group (group C) had an average percentage of live/born of 83.4% (SD+/−7.9). The average percentages for stillborns for groups A, B and C were 8.8 (SD+/−9.66), 6.6 (SD+/−9.7), and 14 (SD+/−11.39), respectively. The average percentages of mummies born to sows of groups A, B, and C were 6.1 (SD+/−6.01), 3.9 (SD+/−4.45), and 2.6 (SD+/−4.01), respectively. The average percentages of livelborn, stillborn and mummies born to the sows of group D were 8.7 (SD+/−8.92), 10.7 (SD+/−11.39), and 81.9 (SD+/−17.18), respectively.

The results of this example demonstrated the stability of the MSV, JA-142, passage 200 after being passed in the host animal six times. There were no significant differences between the group of sows treated with the MSV (group A) and those sows that were exposed to the Backpassage 6 virus (group B) in the categories of farrowing performance, leukopenia, rectal temperatures, and the clinical observations of either the sows or the piglets. In addition, the results in these same categories for the groups A and B were comparable to those achieved by group C that had been treated with sterile diluent. Finally, the performance of the sows that had been exposed to the virulent parent virus of MSV, JA-142, passage 4, clearly illustrated the level of attenuation of the MSV and the lack of reversion to virulence by the Backpassage 6, JA-142 virus.

EXAMPLE 4
Materials and Methods

This example evaluated the safety and level of attenuation of administering a 10× concentration of MSV, JA-142, passage 201. The study was performed on the pregnant sow model and monitored the effect of this dosage on reproductive performance. The study consisted of three groups, A, C, and D. Group A was inoculated intra-nasally with PRRS MSV, JA-142, passage 200. Group C was inoculated intra-nasally with sterile diluent, to act as a normal control group. Group D was inoculated intra-nasally with 10× JA-142, passage 201. All inoculations were given at about 93 days gestation. Body temperatures of the sows were monitored for the first seven days following inoculation (vaccination). Blood samples were collected from the sows once a week and at time of farrowing. Prior to and following inoculation, total white blood cell counts were determined as in Example 2. The health status of each animal was monitored daily for the duration of the study up to and following farrowing for 14 days. Clinical observations of the sows were made from −1 DPV through farrowing. The farrowing performance was evaluated by observing the health status of the piglets born. PRRSV ELISA assays were preformed following the exposures of the sows with the test article. Attempts to isolate PRRSV from serum samples were performed on MA-104 cells following exposure to the test article. Clinical observations of the piglets were made from farrowing until 14 days of age. Blood samples were collected from the piglets at birth, 7 and 14 days of age. PRRSV ELISA assays were performed on the piglet sera weekly following farrowing. Piglets were also weighed at birth, day 7 post farrowing, and at necropsy. At necropsy, the lungs of each piglet were scored for percent lung involvement.

Results and Discussion

There were no significant differences between groups given a 10× dose of MSV, JA-142, passage 201, groups given a regular dose of MSV, JA-142, passage 200, and groups given sterile diluent. Therefore, based on the safety and attenuation of MSV, JA-142, passage 200 and the lack of any significant difference in the results comparing these groups, a 10× dose of MSV, JA-142, passage 201 was shown to be safe, attenuated and effective in inducing antibodies against PRRSV.

EXAMPLE 5
Materials and Methods

This example demonstrated that a minimal vaccine dose of PRRSV, JA-142, passage 205, representing MSV+5, is efficacious in an experimental respiratory challenge model in feeder pigs. Pigs were divided into three groups. Group 1 was inoculated intramuscularly with PRRS MSV, JA-142, passage 205 at a titer of 2.0 logs/dose. Group 2 was inoculated intramuscularly with sterile diluent. Group 3 acted as normal controls. Pigs from groups 1 and 2 were challenged with a PRRSV isolate with an RFLP pattern of 144 on day 28 post vaccination. Body temperatures of the pigs were monitored for the first seven days following vaccination and daily following challenge. Each animal was weighed at vaccination, challenge, weekly throughout the study, and necropsy. Blood samples were collected weekly following vaccination and every two days following challenge. The health status of each animal was monitored daily for the duration of the study. At necropsy, each animal was sacrificed and the lungs were scored for percent lung involvement as in Example 2. PRRSV ELISA assays were performed following the exposures of the pigs with the test articles and challenge. Following exposure to the test articles, attempts to isolate PRRSV from serum samples were performed on MA-104 cells. Virus isolation and ELISA results were analyzed using a Chi-square analysis which tests whether the percentage of positive animals is the same in each group. White blood cell counts were performed as in Example 2.

Results and Discussion

Pigs from group 1 (vaccinated pigs) fared better in all aspects of this example than did the pigs from group 2 (pigs given sterile diluent). Clinical scores, rectal temperatures, and percent lung involvement were all higher for the pigs given sterile diluent. Weight gain and white blood cell counts were lower for the pigs receiving the sterile diluent. There was also a significant reduction in viremia beginning on day 4 post-challenge in the group given vaccine. On days 10 and 11 post-challenge, the number of animals positive for viremia decreased further in the vaccinated group, but remained the same in the group receiving sterile diluent.

An ELISA was used to monitor anti-PRRSV serological status prior to and following vaccination and challenge. All pigs were negative (S/P ratio<0.4) at the time of vaccination. All pigs including the vaccinates were negative at 7 DPV (Days Post Vaccination). Seven days later, 21 of 22 vaccinated pigs were tested as positive for antibody to PRRSV. Two pigs of group 1 remained negative during the pre-challenge period and serological converted at 8 days post challenge (8 DPC). All of the pigs in group 2 were negative at trial day 0 and remained negative throughout the pre-challenge period. On trial day 39 (8 DPC) 17 of the 22 non-vaccinated challenged pigs (Group 2) tested as sero positive. All of the pigs in group 3 (normal controls) remained sero-negative throughout the study.

Virus isolations from sera were performed before and after vaccination. Of the 22 vaccinated pigs, 17 were positive by 2 DPV, 18 were positive by 4 DPV and 19 were positive by 7 DPV. Following vaccination, vaccine virus was not recovered at all from one pig and not until 0 DPC for another. These results correspond to the sero-negative status of these pigs during the post vaccination observation period. At the time of challenge, 55% of the vaccinated pigs were viremic positive. Following challenge, this percentage rose to 82% (at 2 DPC) and gradually decreased to 9% on 11 DPC. All pigs in group 2 were negative at 0 DPC and increased to 82% positive at 2 DPC and 91% at 4 DPC. On 6 and 10 DPC, group 2 was approximately 82% virus positive and 73% of this group was positive on 11 DPC. The normal controls, group 3, remained negative for the duration of the study.

Rectal temperature monitoring showed an overall group increase experienced by group 2. One-half of the pigs in this group experienced a rise of 1° F. over the pre-challenge average for 2 or more days during the 11 day observation period. In comparison, only four of the 22 pigs in the vaccinated group experienced temperatures of 1° F. over their pre-challenge average. The average duration of those animals experiencing elevated temperatures for two or more days was 2.2 days for group 1 and 4 days for group 2. None of the pigs in group 3 experienced increases of 1° F. over their pre-challenge average for two days or longer.

Weight gain was monitored over the 11 day observation period. Pigs in group 3 gained an average of 1.06 pounds/day, pigs in group 2 gained an average of 0.94 pounds/day and pigs in group 1 gained an average of 0.53 pounds/day. Therefore, non-vaccinated challenged pigs gained only about 57% as much weight as did vaccinated challenged pigs and only 50% as much weight as the control group.

Leukopenia (white blood cell counts) were monitored during the post challenge observation period. Group 3 experienced a 5% reduction in the group average on trial day 33 (2 DPC) when compared to the pre-challenge average. For group 2, white blood cell counts dropped an average of 41% and did not return to pre-challenge levels until 11 DPC. The vaccinated group experienced a group average drop of 12% on trial day 34 (3 DPC). The counts returned to pre-challenge level on the next day and remained equal to the pre-challenge level for the duration of the observation period.

Daily clinical observations were made from trial day 28 (−4 DPC) through trial day 42 (11 DPC). All pigs were free of any observable clinical signs during the pre-challenge period. Group 3 remained free of any clinical signs for the duration of the post challenge period. Five of the pigs in group 2 were observed to have post challenge clinical signs. These signs became evident at 6 DPC and were not considered to be severe. The vaccinated pigs had only 1 clinical sign observed during the 11 day post challenge observation period.

At the termination of the study, lungs were evaluated for observable lung lesions. Group 3 had normal lungs and a group average score of 0.02. The individual pig scores for group 2 ranged from a low of 33 to a high of 98 for a group average of 78.33. The scores of the vaccinated group ranged from 30 to a high of 90 with a group average of 53.20.

The data in this example demonstrated the efficacy of a modified live Atypical PRRS viral vaccine. The vaccine was administered at a minimal dose of 2.0 logs per dose containing the fifth passage beyond the MSV (JA-142, passage 205). Efficacy of the vaccine was demonstrated by significantly reducing the extent of lung lesions, the severity of post challenge leukopenia, and post challenge fever. Additionally, a normal growth rate was maintained in vaccinated/challenged pigs compared to that achieved by the normal control pigs and significantly better than that achieved by non-vaccinated/challenged pigs.

EXAMPLE 6

Materials and Methods

This example compared four groups, groups 1,2, and 3 having twenty pigs each, and group 4 having 10 pigs. Goup 1 was inoculated intramuscularly (IM) with PRRS MSV, JA-142, passage 205, at a titer of about 2,5 logs/dose. Group 2 was inoculated intra-nasally with PRRS MSV, JA-142, passage 205, at a titer of about 5.0 logs/dose. Group 3 was inoculated IM with sterile diluent. Group 4 acted as strict controls. Pigs were challenged with a PRRSV isolate from South Dakota State University (SDSU) with an RFLP pattern of 144 on day 28 post-vaccination. Body temperatures of the pigs were monitored daily following challenge. Each animal was weighed at vaccination, challenge, weekly for the duration of the study, and necropsy. Blood samples were collected weekly following vaccination and every two days following challenge. The health status of each animal was monitored daily for the duration of the study. At the termination of the study, animals were sacrificed and their lungs scored for percent lung involvement.

PPRSV ELISA assays were performed following the exposures of the pigs with the test articles and challenge. Attempts to isolate PRRSV from serum samples were also performed on MA-104 cells following exposure to the test articles. WBC counts and clinical observations were determined post inoculation as in Example 2.

Results and Discussion

At zero days post vaccination (DPV), all pigs in this example were serologically negative to PRRSV as indicated by having a S/P ratio<0.4. At 14 DPV, 70% of the pigs in group 1 and 95% of the pigs in group 2 tested positive for the presence of anti-PRRSV antibody. Only one vaccinated pig of group 1, remained sero-negative throughout the pre-challenge period. This pig became sero-positive at seven days post challenge (DPC). All of the pigs in groups 3 and 4 remained negative throughout the pre-challenge period. At nine DPC, all of the pigs in group 3, the sterile diluent treated group, tested positive by ELISA for PRRSV antibody. The normal controls, group 4, remained negative for the duration of the study.

The virus isolation results correlated well with serological results. Only one pig remained negative for virus isolation from serum and this corresponded to the sero- negative status during the post vaccination period. These results indicate a relationship between post vaccination viremia and serological conversion with vaccine dosage. Group 2 was 100% sero-positive at 14 DPV as compared to 70% for group 1. The high dose group (group 2) was 85% and 90% viremia positive at 14 and 21 DPV, respectively. In comparison, the low dose group (group 1) was 55% and 85% positive for the same test days.

Following challenge, 89% of the animals in group 3 experienced temperatures that were one degree F or greater than the pre-challenge values for two or more days. In group 1, 75% of the animals experienced temperatures of one degree or greater for two or more days. While only 45% of the animals of group 2 experienced elevated temperatures. In comparison, 30% of the animals in the normal control group (group 4) experienced elevated temperatures for two or more days during the 11 day observation period.

Treatment with either the high vaccine dose or the low vaccine dose appeared to have no detrimental effect on the growth performance during the post-vaccination period (−3 DPV to 28 DPV). The average daily weight gain for groups 1 and 2 was 0.77 lbs./day and 0.76 lbs./day, respectively. For comparison, groups 3 and 4 had average daily weight gains of 0.77 lbs. and 0.78 lbs., respectively. Following challenge, the vaccinated groups out performed the sterile diluent group by 0.05 lbs./day (group 1) and 0.15 lbs./day (group 2). The normal controls outgained the vaccinates during the same time period by an average of 0.4 to 0.5 lbs./day.

Eighty-four percent (16 of 19) of group 3, the sterile diluent treatment group, experienced a 25% or greater drop in their WBC count for one or more days after challenge. The normal controls had 3 of 10 (30%) that had experienced similar decreases. Following challenge, the vaccinated groups, the low dose (group 1)and the high dose (group2) had 11 of 20 (55%) and 3 of 20 (15%) experiencing leukopenia of 25% for one or more days.

The clinical observations made prior to the challenge indicated that the pigs were of good health status. Following challenge, the level of health status did not significantly change for those pigs that were challenged (groups 1, 2, & 3). Lethargy, respiratory signs, and lost appetite were the clinical signs observed and these were described as mild in severity. The clinical signs reported for one pig in group 2 could be attributed to the bacterial pneumonia (see discussion below on lung lesions) that it was experiencing. The normal control group (group 4) was free of any observable clinical signs during the 11 day observation period.

At the termination of the study, pigs were sacrificed and the lungs were observed for PRRS-like lesions to score the extent of lung involvement. The percent of involvement was scored for each lobe then multiplied by the percent the lung represented for the total lung capacity. For example, 50% lung involvement for a diaphragmatic lobe was then multiplied by 25% to equal 12.5% of the total lung capacity. The maximum score that could be obtained was 100. The group average lung score for the normal controls (group 4) was zero. The group average score for the sterile diluent treatment group (group 3) was 70.08. The vaccinated treatment groups average scores were 48.83 for the low dose (group 1) and 17.76 for the high dose (group 2). One pig was observed to have a lung score of 62.5, the highest score within group 2. The lesions noted on this pig's lungs were described to be associated with bacterial pneumonia.

From the results of this study, both dosage levels of the atypical PRRS MSV vaccine reduced the severity of the clinical signs associated with the respiratory disease caused by the PRRSV. A full field dose outperformed the minimal dose as indicated by the significant reduction in lung lesion scores.

EXAMPLE 7

Materials and Methods

This example determined the sequence of the attenuated MSV, JA-142 from the 201st passage as well as the sequence of passage 3 of the field isolate virus, JA-142. The attenuated virus isolate was obtained from the master seed stock representing the 201 st passage in MA-104 simian cells of a PRRSV isolated from swine affected with PRRS.

The virus was grown on 2621 cells, a monkey kidney cell line, also referred to as MA-104 and as USU-104 (Gravell et al., 181 Proc. Soc. Exp. Biol. Med. 112–119 (1986), Collins et al., Isolation of Swine Infertility and Respiratory Syndrome Virus (Isolate ATCC VR-2332) in North America and Experimental Reproduction of the Disease in Gnotobiotic Pigs, 4 J. Vet. Diagn. Invest. 117–126 (1992)) (the teachings of which are hereby incorporated by reference). Cells were cultured in 50 ml Dulbecco modified Eagle's MEM medium (Life Technologies, Inc., Gaithersburg, Md.), supplemented with 10% fetal calf serum and 50 μg/ml gentamicin (Sigma Chemical Co., St. Louis, Mo.) in a 5% humidified $CO_2$ atmosphere at 37° C. in 75 $cm^2$ plastic tissue culture flasks. Cells were maintained by passage at 5–7 day intervals. Cells were dislodged from the surface with trypsin-versene and split 1:4. To infect cells, media was decanted and 1 ml of cell supernatant containing virus at a titer of approximately $10^5$–$10^6$ tissue culture infective doses ($TCID_{50}$) was added for 30 min. Thirty ml fresh media containing 4% fetal calf serum was added. Cells were incubated as described above for 5 days, at which time cytopathic effect was evident in the culture. Culture medium containing virus was centrifuged at 2000 rpm in a Beckman TJ6 centrifuge to pellet cellular debris.

Viral genomic RNA was purified by adding 1120 μl of prepared Buffer AVL (QIAamp Viral RNA Isolation Kit, Qiagen)(QIAGEN, Inc. Valencia, Calif.)/carrier RNA to a 280 μl sample of virus-containing culture medium. The mixture was vortexed and incubated at room temperature for 10 min. 1120 μl ethanol was added and the mixture was inverted several times. RNA was absorbed to the matrix of a QIAamp spin column by repeated centrifugation of 630 μl aliquots at 6,000×g for 1 min. The column was washed with 500 μl buffer AW and centrifuged to remove all traces of wash solution. RNA was eluted from the column with 60 μl of diethylpyrocarbonate-treated water at room temperature. Purified RNA was stored at −70° C. or used immediately for synthesis of CDNA.

For cDNA synthesis, viral RNA was heated at 67° C. for 7 min, primed with random hexamers or PRRSV-specific primers, and reverse transcribed with Superscript II RNase $H^-$reverse transcriptase (RT) (Life Technologies, Inc.). Reactions contained 5 mM $MgCl_2$, 1×standard buffer II (Perkin Elmer Corp. Wellesley, Mass.), 1 mM each of dATP, dCTP, dGTP and dTTP, 1 unit/μl of RNase inhibitor, 2 units of RT, and 1 μl of RNA in a 40 μl reaction. Reaction mixtures were incubated for 15 min at 42° C., for 5 min at 99° C. and for 5 min at 5° C.

Polymerase chain reaction (PCR) was performed to obtained DNA fragments for sequencing as follows: 10 μl portions of cDNA reaction mixture were combined with the following reagents, resulting in a 25μl reaction containing 2 MM $MgCl_2$, 1×standard buffer II (Perkin Elmer), 0.2 mM each of dATP, dCTP, dGTP and dTTP, 0.3 μM of 5'- and 3'-PRRSV-specific primer, and 0.375 units AmpliTaq Taq polymerase (Perkin Elmer). Reactions were prepared by heating for 4 min at 93° C. in a thermal cycler, then 35 cycles consisting of 50–59° C. for 30 sec, 72° C. for 30–60 sec, and 94° C. for 30 sec. Specific times and temperatures varied depending on the annealing temperatures of the primers in each reaction and the predicted length of the amplification product. A final incubation was performed for 10 min at 72° C. and reactions were placed at 4° C. PCR products were purified with a Microcon 100 kit (Amicon, Bedford, Mass.).

Rapid amplification of cDNA ends (RACE) PCR was performed to obtain the extreme 5'-end sequence of the genomic RNA, based on the method of Frohman, Mass., On Beyond Classic RACE (Rapid Amplification of cDNA Ends), 4 PCR Methods and Applications S40–S58 (1994) (the teachings of which are hereby incorporated by reference). Viral RNA was isolated and converted to cDNA as described above, with random hexamers as primers. Reaction products were purified on a Microcon 100 column (Amicon). A poly(dA) tail was added to the 3'-end by incubating 10 $\mu$l of cDNA in a 20 $\mu$l volume containing 1×buffer 4 (New England Biolabs, Beverly, Mass.), 2.5 mM $CoCl_2$, 0.5 mM dATP and 2 units terminal transferase (New England Biolabs), for 15 min at 37° C. The reaction was stopped by heating for 5 min at 65° C. and then was diluted to 200 $\mu$l with water.

PCR was performed using the Expand$^a$ Long Template PCR System (Boehringer Mannheim, Mannheim, Germany) in a 50 $\mu$l reaction volume containing 10 $\mu$l of diluted, poly(dA)-tailed cDNA, 1×buffer 3,0.35 mM each of dATP, dCTP, dGTP and dTTP, 0.625 mM $MgCl_2$, 0.04 $\mu$M $Q_t$ primer (Frohman, 1994), 0.3 $\mu$M $Q_o$primer (Frohman, 1994), 0.3 $\mu$M 5'-CGCCCTAATTGAATAGGTGAC-3' and 0.75 $\mu$l of enzyme mix. Reactions were heated at 93° C. for 2 min in a thermal cycler and cycled 25 times with each cycle consisting of 93° C. for 10 sec, 63° C. for 30 sec, and 68° C. for 12 min. After 25 cycles, the reaction was incubated at 68° C. for 7 min and held at 4° C. An aliquot of the reaction was diluted 100-fold and 5 1 of diluted product was added to a second PCR reaction containing, in 50 $\mu$l, 1×buffer 1, 0.35 mM each of dATP, dCTP, dGTP and dTTP, 0.3 $\mu$M primer Qi (Frohman, 1994), 0.3 $\mu$M 5'-CCTTCGGCAGGCGGGGAGTAGTGTTTGAGG TGCTCAGC-3', and 0.75 $\mu$l enzyme mix. Reactions were heated at 93° C. for 2 min in a thermal cycler and cycled 25 times with each cycle consisting of 93° C. for 10 sec, 63° C. for 30 sec, and 68° C. for 4 min. After 25 cycles, the reaction was incubated at 68° C. for 7 min and held at 4° C. Reaction products were electrophoresed on a 1% agarose gel and the band of approximately 1500 bp was purified using the QIAgen QXII gel purification kit. Eluted DNA was cloned into the pGEM-T vector (Promega, Madison, Wis.) using standard procedures. Individual clones were isolated and grown for isolation of plasmid DNA using QIAgen plasmid isolation kits.

PCR products and plasmid DNA were combined with appropriate primers based on related PRRSV sequences in Genbank or derived from known sequences, and subjected to automated sequencing reactions with Taq DyeDeoxy terminator cycle sequencing kits (Applied Biosystems, Foster City, Calif.) and a PR 2400 Thermocycler (Perkin Elmer) at the University of Minnesota Advanced Genetic Analysis Center. Reactions were electrophoresed on an Applied Biosystems 3700 DNA sequencer. Sequence base calling and proofreading were performed primarily with the Phred program (University of Washington Genome Center) and fragment assembly was performed primarily with the Phrap program (University of Washington Genome Center). Additional computer software including the Lasergene Package (DNASTAR Inc., Madison, Wis.), Wisconsin package version 9.1 (Genetics Computer Group, Madison, Wis.), and EuGene (Molecular Biology Information Resource, Houston, Tex.) was used to analyze the sequence. The final viral genomic sequence was assembled from approximately 100 PCR reactions and 428 DNA sequencing reactions.

Results

The results of Example 7 are given as SEQ ID Nos. 1 and 2 wherein SEQ ID No. 1 represents the DNA sequence of the 201 st passage of the Master Seed Virus, JA 142 and SEQ ID No. 2 represents the DNA sequence of the field-isolated virulent virus, JA 142 after three passages. Additionally, RNA sequences of the 201 st passage JA-142 and the field isolated virulent virus, JA-142 are provided as SEQ ID Nos. 3 and 4, respectively. These RNA sequences vary slightly from the DNA sequences at the 5' end of the genome.

EXAMPLE 8

Materials and Methods

This example demonstrated the presence or absence of a NspI restriction endonuclease site for differentiation between field strains of PRRSV and an attenuated strain of PRRSV. Thus, this example provides a diagnostic testing method using restriction fragment length polyrnorphism (RFLP) analysis. RFLP is useful as a diagnostic tool because the NspI site is present in most field strains of PRRSV. Samples, preferably of serum, should be gathered from a suspected infected individual for RT-PCR/RFLP based diagnostic testing. In this case, known virulent field strains were used for testing to provide known result standards for later diagnostic testing. While Qiagen products and specific method steps are disclosed, it is understood that other methods and products known in the art can be utilized.

For performance of the diagnostic test (and to obtain the standards disclosed below) viral genomic RNA was isolated using a QIAamp Viral RNA Isolation Kit (Qiagen, Inc. Valencia, Calif.) and following the mini spin protocol. The following steps were used:

1. Carrier RNA was added to Buffer AVL and placed at 80° C. for five minutes or until dissolution of the precipitate to form solution 1. Do not heat Buffer AVL over 5 minutes or more than 6 times. Frequent warming/extended incubation will cause degradation of carrier-RNA, leading to reduced recovery of Viral RNA and eventually false negative RT-PCR results.

2. 1120 $\mu$l of solution 1 was pipetted into a microfuge tube.

3. 280 $\mu$l of serum sample was added to the microfuge tube holding solution 1 and the resulting mixture was vortexed thoroughly to ensure that solution 1 and the sample were well mixed together. This is done to lyse the sample under highly denaturing conditions, inactivate RNases, and ensure isolation of intact viral RNA. Carrier-RNA improves binding of viral RNA to the QIAamp membrane, and limits possible degradation of the viral RNA due to any residual RNase activity.

4. This mixture was incubated at room temperature for 10 minutes. Viral particle lysis is substantially complete after lysis for 10 minutes at room temperature, although longer times may be used with little or no effect on the yield or quality of the purified RNA.

5. 1120 $\mu$l of ethanol (EtOH) (96–100%) was added to the incubated mixture and mixed thoroughly by inverting the tube several times.

6. A QIAamp spin column was placed in a 2 ml collection tube and 630 $\mu$l of the mixture obtained in step five was added. This mixture was then centrifuged at 6000×g for one minute.

7. The filtrate in the collection tube was discarded.

8. The QIAamp spin column was placed into a clean 2 ml collection tube and another 630 µl of the mixture obtained in step five was added to the spin column and centrifuged at 6000×g.

9. The filtrate in the collection tube was discarded.

10. The QIAamp spin column was placed into a clean 2 ml collection tube and another 630 µl of the mixture obtained in step five was added to the spin column and centrifuged at 6000×g.

11. 500 µl of Buffer AW1 was added to the spin column and centrifuged at 6000×g for one minute.

12. The tube containing the filtrate was discarded.

13. The spin column was placed into a clean 2 ml collection tube and 500 µl of Buffer AW2 was added and centrifuged at 18,500×g for three minutes. The filtrate was discarded.

14. The spin column was placed into a new 2 ml collection tube and centrifuged at 6000×g for one minute to remove the last traces of AW2. The filtrate was discarded.

15. The spin column was placed into a clean 1.5 ml microcentrifuge tube and 60 µl of Buffer AVE at room temperature. This mixture was incubated for one minute at room temperature before being centrifuged at 6000×g for one minute to elute the RNA.

16. The eluted RNA was pipetted into a 1.5 ml microfuge tube and stored at −70° C. if the RT-PCR is not able to be done immediately.

RT-PCR was performed on the eluted RNA obtained in the above method. A 20 µl "master mix" containing the following: 5 µl of 1×RT-PCR buffer, 1 µl of 0.4 mM DNTP mixture (containing equal amounts each of dATP, dCTP, dGTP and dUTP), 0.1 µl of 0.08 units/Rx RNAse inhibitor, 0.5 µl 500 nM BVDV forward primer, 0.5 µl 500 nM BVDV reverse primer, 11.9 µl RNAse/DNAse free water, and 1 µl Qiagen "secret" enzyme mix was added to a tube. 5 µl of the eluted RNA was then added to the tube.

Reactions were initially heated at 50° C. for 30 minutes followed by heating at 95° C. for 15 minutes in a thermal cycler and then cycled 35 times with each cycle consisting of 57° C. for 30 seconds, 72° C. for 45 seconds, and 94° C. for 45 seconds. After 35 cycles, the reaction was incubated at 57° C. for 30 seconds followed by 72° C. for 7 minutes and finally held at 4° C. To check the PCR on an agarose gel, 1 g of agarose was added to 100 ml of 1×TAE buffer before microwaving on high for two minutes. Next, 4 µl of 10 mg/ml EtBr was added to the heated gel before casting the gel and allowing it to solidify for 15–30 minutes. 4 µl of the PCR product was mixed with 1 µl loading dye. 3.5 µl of a 1 Kb ladder was added to 13.2 µl of water and 3.3 µl of loading dye for use as a marker. 4 µl of the marker mixture was electrophoresed on the gel, indicating a 1 Kb product. A band from the PCR product should be approximately 1 Kb in size. The gel was then run at 140 volts for 1 hour or 75 volts for two hours.

The band of approximately 1 Kb was purified using the QIAgen Qiaquick PCR Purification Kit (Qiagen, Inc. Valencia, Calif.). A column was placed in a collection tube and 20 µl PCR reaction sample and 100 µl PB buffer were added. This mixture was mixed thoroughly before spinning for 1 minute at full speed in an Eppendorfmicrofuge. The flow-through products were discarded and the column was replaced in the tube. The tube was spun for another full minute and allowed to stand for at least one minute at room temperature. The column was then spun a third time at full speed. The eluent remaining contains purified PCR product and water.

The PCR/water product from above was then digested with Nsp I, a restriction enzyme and then electrophoresed on a 1.5% agarose gel to determine fragment numbers and lengths.

Results

The results of Example 8 are used for diagnostic results. It was found that most of the field strains for the PRRS virus contain one Nsp I restriction site, therefore yielding digestion products of 549 and 476 bp from the 1 Kb RT-PCR product. The parent strain of the JA-142 passage 200 possesses this phenotype. Only one PRRS strain, BI-Vetmedica 142 passage 200 (+5), contains two Nsp Isites, yielding digestion products of 476, 380, and 173 bp from the 1 Kb RT-PCR product. Some field strains possess no Nsp I site within this RT-PCR product, and therefore exhibit no digestion and electrophoresis of one fragment of 1021 bp. Thus, the presence of the attenuated virus can be determined.

EXAMPLE 9

Materials and Methods:

This Example tested the degree of protective immunity against maternal reproductive failure of swine vaccinated by one or two attenuated strains of PRRSV.

Fifty gilts were separated into five experimental groups designated A–E and having ten gilts in each group. Gilts of group A were neither vaccinated nor challenged and were therefore used as strict controls. Gilts of group B were used as the challenge controls and therefore received no vaccinations but were challenged at or about day 90 of gestation. Gilts of groups C, D, and E were each vaccinated twice before conception with one month between vaccinations. These gilts were then challenged at or about day 90 of gestation. Two strains of vaccine virus (strains RespPRRS/Repro and JA-142) were used to challenge the gilts. [Is RespPRRS/Repro commercially available?] The challenge consisted of oronasal exposure to virulent PRRSV. Gilts of group C were vaccinated twice with strain RespPRRS/Repro. Gilts of group D were vaccinated first with RespPRRS/Repro and then with JA-142. Gilts of group E were vaccinated twice with strain JA-142. Gilts and their progeny were observed at least twice daily for clinical signs and tested for both PRRSV and homologous antibody at selected intervals. The gilts of groups C, D, and E were bled just before their first vaccination and at selected times thereafter until they were necropsied, usually at or about 14 days after farrowing or sooner if they aborted. Gilts of group A and B were bled just before challenge and at identical selected times thereafter. Beginning one month after the second vaccination of groups C, D, and E, all gilts were bred as they came into estrus. All of the boars used for breeding purposes were free of antibody against PRRSV. Near the time of challenge, each gilt was moved to an isolation room and was kept in isolation until the experiment was ended for that gilt and her litter at two weeks after farrowing or sooner in the case of abortion or premature death of all progeny. All surviving pigs were weighed when they were two weeks old. Gilts that failed to conceive at their first, second, or third estrocycle were excluded from the experiment. This reduced the numbers of pregnant gilts for groups B, C, D, and E to 9, 8, 9, and 9, respectively. The same limitation did not apply to group A because for this group, there were more than ten nonvaccinated gilts available from which to make a random selection for inclusion in group A.

Results and Discussion:

All vaccinated gilts (groups C, D, and E) responded to vaccination with the production of antibodies against PRRSV. These results are provided in FIG. 1 which is a graph representing the ratio of the total number of samples to samples positive for PRRSV antibodies. Blood samples were collected from the gilts just before their first vaccination and at selected times thereafter during an interval of 196 days. Depending on when gilts conceived (breeding was started on day 60), they were progressively removed from this group. Beginning at or about 90 days of gestation, blood samples were collected just before they were challenged, seven days after challenge, fourteen days after challenge, at the time of delivery (which was at or about 24 days after challenge if the gilt farrowed normally, or sooner if the gilt aborted), and at the time of necropsy (which was at or about 38 days, i.e. 2 weeks after farrowing, or sooner if the gilt lost all of her live born pigs before 2 weeks after farrowing). These results are provided in FIG. 2.

Figure 2:
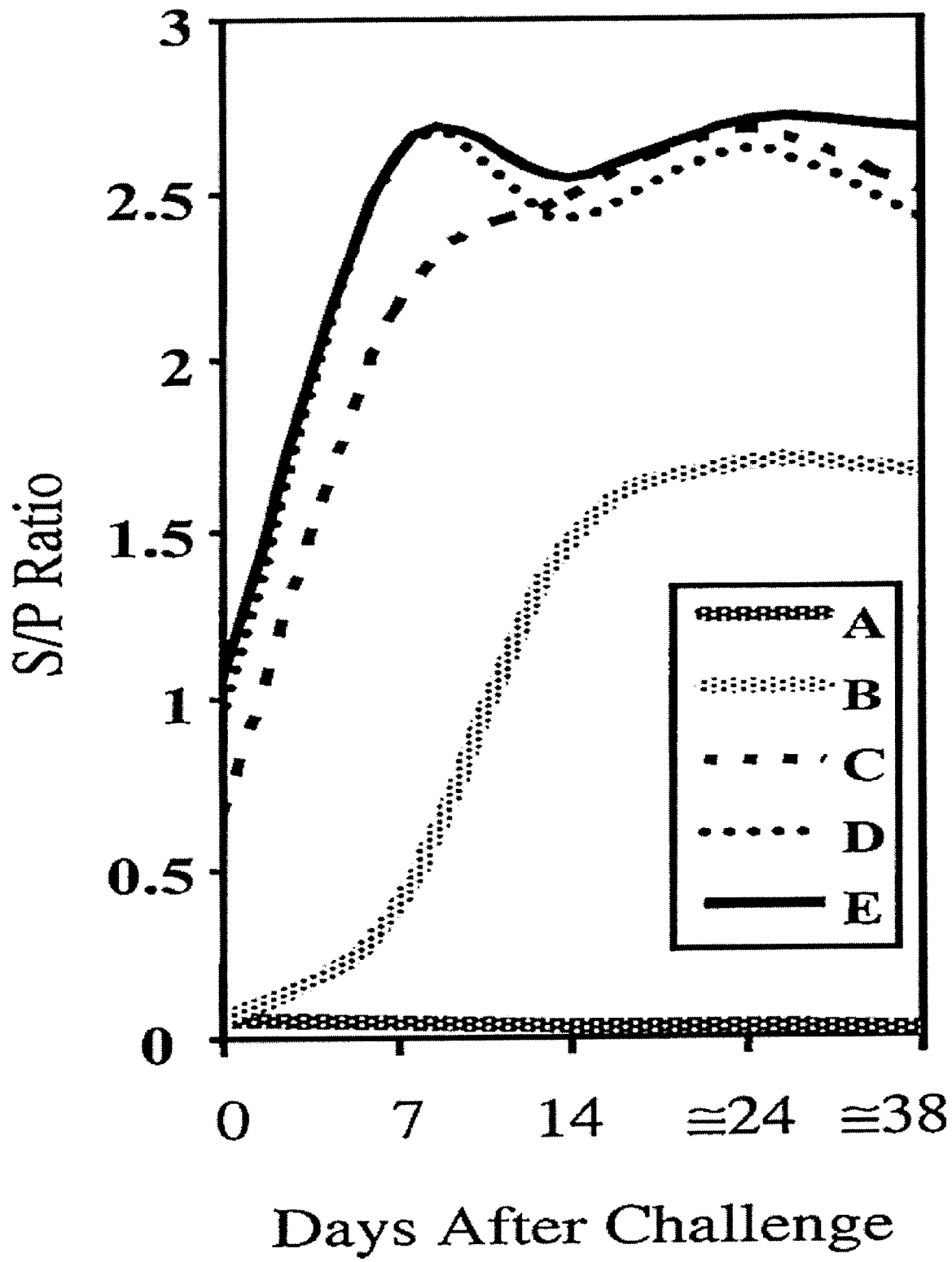
FIG. 2 is a graph illustrating the ratio of samples which tested positive for antibodies against PRRSV to the total number of samples over a 38 day testing period after challenge.

As shown in FIGS. 1 and 2, antibody levels increased after challenge for groups B, C, D, and E. For group B, the nonvaccinated group, these antibodies appeared only after challenge while they were present prior to challenge for groups C, D, and E. Gilts of group A and all boars used for breeding both vaccinated and nonvaccinated gilts remained free of antibody against PRRSV throughout the experiment.

None of the vaccinated gilts had any obvious vaccine-related clinical signs after vaccination. Conversely, all of the gilts (both vaccinated and nonvaccinated) had moderate to severe clinical signs following challenge. A summary of the number of live born and still born pigs, the number of aborted, late term dead, and mummified fetuses, and the number and weight of pigs still alive 14 days after farrowing is presented in Table 4. All of the pigs of groups C, D, and E that survived through day 14 were robust and were judged to be in excellent health. None of these pigs yielded infectious virus from either serum or lung lavage samples. In contrast, all pigs of group B that survived through day 14 were unthrifty and were shown by virus isolation to be infected. A measure of the difference in general health is provided by the relative body weights of pigs of group B versus those of pigs of groups A, C, D, and E. The appearance of pigs of group B suggested that few, if any, would have recovered or would have recovered sufficiently to warrant any expectation of their continued survival under conditions of commercial swine production.

TABLE 4

Effect of Vaccination Against Porcine Reproductive and Respiratory Syndrome Virus (PRRSV) on the Health and Survival of Fetuses and Pigs of Gilts Subsequently Exposed to Highly Virulent PRRSV

| | | Day 0[1] | | | | | Day 14[2] | | |
|---|---|---|---|---|---|---|---|---|---|
| Group | Gilts[3] | Liveborn pigs | Stillborn pigs | Late-term dead fetuses | Mummified fetuses | Aborted fetuses | Live pigs | Mean pig weight (lbs) | Mean litter weight (lbs) |
| A | 10 | 102 | 17 | 1 | 2 | 0 | 95 | 9.8 | 93.1 |
| B | 9 | 24 | 3 | 62 | 5 | 0 | 16 | 5.6 | 10.0 |
| C | 8 | 37 | 8 | 31 | 4 | 13 | 27 | 11.1 | 37.5 |
| D | 9 | 47 | 10 | 14 | 0 | 39 | 38 | 8.7 | 36.7 |
| E | 9 | 50 | 13 | 38 | 3 | 0 | 33 | 10.4 | 38.1 |

[1]At the time of farrowing.
[2]On the day the experiment was ended.
[3]Pregnant gilts that aborted or farrowed.

Vaccination with either strain (RespPRRS/Repro and JA-142) of attenuated PRRSV provided a level of protective immunity that was demonstrated by challenge exposure. Although protection was incomplete regardless of the vaccine strain or method of vaccination, it was sufficient to recommend vaccination as an economically beneficial procedure. Whereas the loss of pigs of group B was essentially complete either due to death or ill health, about 40% of the pigs of litters of groups C, D, and E (on a per litter basis and using 100% as the value for litters of group A) would have survived to market. The excellent health status of the surviving pigs of groups C, D, and E is emphasized by the fact that the mean body weight of pigs of these groups (when calculated collectively) is the same as that of pigs of group A. The economic impact of saving about 3.6 pigs/litter through vaccination is difficult to project with certainty, however, if a reasonable assumption is made that each pig is worth about $20.00 in profit and reduced overhead through sharing of fixed costs, then two vaccinations at an estimated cost of about $1.00 each would return $72.00 for each $2.00 invested. On the basis of these assumptions, anything more than a prevalence of PRRSV-induced reproductive failure of one case for every 36 pregnancies (or a severe clinical epidemic once every 18 months assuming 2 pregnancies/year) would make vaccination cost effective. Moreover, it seems likely that the results of this study present the worst case scenario. Namely, the strain used for challenge was selected to represent the most virulent field strains of PRRSV currently present in North America and may not accurately reflect the majority of field strains against which vaccines are likely to be more protective.

We claim:

1. A virus having a restriction enzyme cleavage pattern of 1-4-2 by the enzymes MLU 1, Hinc II, and Sac II, respectively, in open reading frame five, said virus being ATCC Accession Number VR-2638.

2. The virus of claim 1 not being cleavable by MLU 1 in open reading frame five.

3. A vaccine comprising the virus of claim 1, and a pharmaceutically acceptable carrier.

4. The vaccine of claim 3, said vaccine capable of eliciting antibody response in a host animal.

5. The vaccine of claim 4, said host animal including swine.

6. A method of immunizing swine against porcine reproductive and respiratory syndrome virus strains, said method comprising the step of administering to swine the vaccine of claim 3.

* * * * *

SEQUENCE LISTING

<160> NUMBER OF SEQ ID NOS: 4

<210> SEQ ID NO 1
<211> LENGTH: 15424
<212> TYPE: DNA
<213> ORGANISM: Porcine reproductive and respiratory syndrome virus

<400> SEQUENCE: 1

| | | | | | |
|---|---|---|---|---|---|
| tcgcccgggc | aggtgttggc | tctatgcctt | ggcatttgta | ttgtcaggag | ctgcgaccat | 60 |
| tggcacagcc | caaaactagc | tgcacagaaa | acgcccttct | gtgacagccc | tcttcagggg | 120 |
| agcttagggg | tctgtcccta | gcaccttgct | tccggagttg | cactgcttta | cggtctctcc | 180 |
| aacccttaa | ccatgtctgg | atacttgat | cggtgcacgt | gcaccccaa | tgccagggtg | 240 |
| tttatggcgg | agggccaagt | ctactgcaca | cgatgtctca | gtgcacggtc | tctccttcct | 300 |
| ctgaatctcc | aagttcctga | gcttggagtg | ctgggcctat | tttacaggcc | cgaagagcca | 360 |
| ctccggtgga | cgttgccacg | tgcattcccc | actgttgagt | gctccccgc | cggggcctgc | 420 |
| tggctttctg | cgatctttcc | aattgcacga | atgaccagtg | aaacctgaa | ctttcaacaa | 480 |
| agaatggtgc | gggtcgcagc | tgagatttac | agagccggcc | agctcacccc | tgcagtcttg | 540 |
| aaggctctac | aagtttatga | cgggttgc | cgctggtacc | ctatagtcgg | acctgtccct | 600 |
| ggagtggccg | attttgccaa | ctccctacat | gtgagtgata | acctttccc | gggagcaact | 660 |
| catgtgctaa | ccaacctgcc | actcccagag | aggcctaagc | tgaagactt | ttgcccttct | 720 |
| gagtgtgcta | tggctgacgt | ctatgatatt | ggccatggcg | ccgtcatgta | tgtggccaaa | 780 |
| gggaaagtct | cctgggcccc | tcgtggcggg | atgaggcga | aatttgaacc | tgtccctagg | 840 |
| gagttgaagt | tgatcgcgaa | ccaactccac | atctccttcc | cgccccacca | cgcagtggac | 900 |
| atgtctaagt | ttgtgttcat | agcccctggg | agtggtgtct | ctatgcgggt | cgagtgccca | 960 |
| cacggctgtc | tccccgctaa | tactgtccct | gaaggtaact | gctggtggcg | cttgtttgac | 1020 |
| tcgctcccac | tggacgttca | gaacaaagaa | attcgccgtg | ccaaccaatt | cggctatcaa | 1080 |
| accaagcatg | gtgtcgctgg | caagtaccta | caacggaggc | tgcaagctaa | tggtctccga | 1140 |
| gcagtgactg | atacagatgg | acccattgtc | gtacagtatt | tctctgttag | ggagagctgg | 1200 |
| atccgccact | tcagactggc | ggaagagcct | agcctccctg | ggtttgaaga | cctcctcaga | 1260 |
| ataagggtag | agcccaatac | gtcgccattg | agtgacaagg | gtggaaaaat | cttccgggtt | 1320 |
| ggcagtcaca | aatggtacgg | tgctggaaag | agagcaagga | aagcacgctc | tggtatgacc | 1380 |
| accacagtcg | ctcaccgcgc | cttgcccgct | cgtgaaatcc | agcaagccaa | aaagcacgag | 1440 |
| gatgccggcg | ctgataaggc | tgtgcatctc | aggcactatt | ctccgcctgc | cgacgggaac | 1500 |
| tgtgttggc | actgcatttc | cgccatcgcc | aaccgaatgg | tgaattccaa | atttgaaact | 1560 |
| actcttcccg | agagggtgag | accttcagat | gactgggcta | ctgacgagga | ccttgtgaac | 1620 |
| accatccaaa | ttctcaagct | ccctgcggcc | ttggacagga | acggtgcttg | tgttggcgcc | 1680 |
| aaatacgtgc | ttaagctgga | aggcgagcat | ggactgtct | ctgtgaccct | ggggatgtcc | 1740 |
| ccttctttgc | tccccttga | atgtgttcag | ggctgttgtg | agcataagag | cggacttggt | 1800 |
| cccccagatg | cggtcgaagt | tttcggattt | gaccctgcct | gccttgaccg | actggctgag | 1860 |
| gtaatgcact | tgcctagcag | tgtcatccca | gctgctctgg | ccgaaatgtc | cggcgacccc | 1920 |
| aaccgtccgg | cttccccggt | cactactgtg | tggactgttt | cacaattctt | tgcccgccac | 1980 |
| agaggaggag | agcaccctga | tcaggtgcgc | ttaggaaaaa | tcatcagcct | ttgtcaagtt | 2040 |

```
gttgaggaat gctgttgcca tcagaataaa accaaccggg ccaccccgga agaggttgcg    2100
gcaaggattg atcagtacct ccatggtgca acaagtcttg aagaatgctt gattaggctt    2160
gagagggttt gcccgccgag cgctgcggac accttctttg attggaatgt tgtgctccct    2220
ggggttgggg cttcaactca gacaaccaaa cagctccatg tcaaccagtg ccgcgctctg    2280
gttcctgtcg tgactcaaga gccttttggac aaagacccag tccctctgac cgccttctcg    2340
ctgtccaatt gctactatcc tgcacaaggt gacgaggttc gtcaccgtga gagctaaac     2400 tccgtactct ctaagctgga gggggttgtt cgtgaggaat atgggctcac gccaactgga    2460
cctggcccgc gacccgcact accgaacggg ctcgtcgaac ttaaagacca gatggaggag    2520
gatctgctaa aactagtcaa cgcccaggca acttcagaaa tgatggcctg ggcagccgag    2580
caggttgatc tgaaagcttg ggtcaaaaac tacccacggt ggacaccgtc accccctcca    2640
ccaagagttc agcctcgaaa aacaaagcct gtcaagagct gccagggaa caaacctgtc    2700 cccgctccac gcaggaaggt cagatctgat tgtggcagcc cgatttcgat gggcgacaat    2760
gttcctgacg gtcgggaaga tttgactgtt ggtggccccc ttgatctttc gacaccatcc    2820
gagccgatga cacctctgag tgagcctgca cctatgcccg cgttgcaata tatttctagg    2880
ccagtgacac ctttgagtgt gctggcccca gtacctgcac cgcgtagaac tgtgtcccga    2940 ccggtgcgc ccttgagtga gccaattttt gtgtctgcac cgcgacacaa atttcagcag    3000
gtggaagaag cgaatctggc ggcaacaatg ctgacgcacc aggacgaacc tctagatttg    3060
tctgcatcct cacagactga atatgaggct tctcccctaa caccactgca gaacatgggt    3120
attctggagg tgggggggca agaagctgag gaagttctga gtgaaaactc ggatacactg    3180
aatgacatca accctgcacc tgtgtcatca agcagctccc tgtcaagtgt taagatcaca    3240
cgcccaaaac actctgctca agccatcatt gactcgggcg ggccctgcag tgggcatctc    3300
cgaaagggaa aagaagcatg cctcagcatc atgcgtgagg cttgtgatgc ggctaagctt    3360
agtgaccctg ccacgcagga atggctttct cgcatgtggg atagggttga tatgctgact    3420
tggcgcaaca cgtctgctta ccaggcgttc cgcatcttag atggtaggtt tgagtttctc    3480
ccaaagatga tactcgagac accgccgccc tacccgtgtg ggtttgtgat gctgcctcgc    3540
acgcctgcac cttccgtggg tgcagagagt gaccttacca ttggttcagt cgccactgaa    3600
gatgttccac gcatcctcgg gaaaatagaa aacgccggca agatgcccaa ccagggggctc    3660 ttgacatcct tcggggaaga accggtgtgc gaccaacctg tcaaggactc ctggatgtcg    3720 tcgcggggt ttgacgagag cacaacggct ccgtccgctg gtacaggtgg tgctgactta    3780
cccaccgatt tgccaccttc agatggtttg gatgcggacg agtgggggcc gttacggacg    3840
gtaagaaaga aagctgaaag gctcttcgac caattgagcc gtcaggtttt taacctcgtc    3900
tcccatctcc ctgttttctt ctcacacctc ttcaaatctg acagtggtta ttctccgggt    3960
gattggggtt ttgcagcttt tactttattt tgcctcttt tgtgttacag ctacccattc    4020
tttggttttg ttccctctt gggtgttttt tctgggtctt ctcggcgtgt gcgcatgggg    4080 gttttttggct gttggttggc ttttgctgtt ggcctgttca agcctgtgtc cgacccagtc    4140
ggcactgctt gtgagtttga ctcgccagag tgtaggaacg tccttcattc ttttgagctt    4200
ctcaaacctt gggaccctgt tcgcagcctt gttgtgggcc ccgtcggtct cggccttgcc    4260
attcttggca ggttactggg cggggcacgc tacatctggc attttttgct taggcttggc    4320
attgttgcag attgtatctt ggctggagct tatgtgcttt ctcaaggtag gtgtaaaaag    4380
tgctggggat cttgtgtaag aactgctcct aatgaaatcg ccttcaacgt gttccctttt    4440
```

```
acgcgtgcga ccaggtcgtc actcatcgac ctgtgcgatc ggttttgtgc gccaaaaggc    4500
atggacccca ttttcctcgc tactgggtgg cgcgggtgct ggaacggccg aagtcccatt    4560
gagcaaccct ctgaaaaacc catcgcgttc gcccagttgg atgaaaagag gatcacggct    4620
agaactgtgg tcgctcagcc ttatgatcct aaccaagccg taaagtgctt gcgggtgtta    4680
caggcgggtg gggcgatagt ggccgaggca gtcccaaaag tggtcaaggt ttccgctatt    4740
ccattccgag ctcccttttt tcccaccgga gtgaaggttg atcctgagtg caggatcgtg    4800
gtcgaccccg cacttttac tacagctctc cggtctggtt actccaccac aaacctcgtc    4860
cttggtgtag gggactttgc ccaactgaat ggattaaaaa tcaggcaaat ttccaagccc    4920 tcggaggag gcccgcacct cattgctgcc ctgcatgttg cttgctcgat ggcgttgcac    4980
atgcttgctg gagtttatgt aactgcagtg gggtcttgcg gtaccggcac caacgatccg    5040
tggtgcacta acccattcgc cgtccctggc tacggacctg gctccctctg cacgtccaga    5100
ttgtgcatct cccaacatgg ccttaccctg cccttgacag cacttgtggc aggattcggt    5160
cttcaggaaa ttgccctagt cgttttgatt ttcgtttcca tcggaggcat ggctcatagg    5220
ttgagttgta aggctgatat gctgtgcgtc ttacttgcaa tcgccagcta tgtttgggta    5280 cccccttacct ggttgctctg tgtgtttcct tgctggttgc gctggttctc tttgcacct    5340 ctcaccattc tatggttggt gttttcttg atgtctgtaa atatgccttc gggaatctta    5400
accgtggtgt tattggttgc tctttggctt ctaggccgtt atactaatgt tgttggtctt    5460
gttaccccct atgatattca ccattacacc aatggccccc gcggtgttgc cgccttggct    5520
accgcaccag atgggactta cttggccgct gtccgccgcg ctgcgttgac tggccgcacc    5580
gtgctgttta cccgtctca gcttgggtcc cttcttgagg gcgctttcag aactcgaaag    5640
ccctcactga acaccgtcaa tgtggtcggg tcctccatgg gctctggcgg agtgttcact    5700
atcgatggga aaattaagtg cgtgactgcc gcacatgtcc ttacgggtaa ttcagccagg    5760 gttttccgggg tcggctttaa tcaaatgctt gactttgatg taaaggggga cttcgccata    5820
gctgactgcc cgaattggca agggctgct cctaagaccc aattctgcga ggatggatgg    5880
actggccgcg cctattggct gacatcctct ggcgtcgaac ccggtgtcat tgggaatgga    5940
ttcgccttct gcttcaccgc gtgcggcgat tccgggtccc cagtgatcac cgaagccggt    6000
gagcttgtcg gcgttcacac aggatcaaac aaacaaggag gaggcattgt tacgcgcccc    6060
tctggccagt tttgcaatgt ggcacccatc aagctgagcg aattaagtga gttctttgct    6120
ggacctaagg tcccgctcgg tgatgtgaag gttggcagcc acataattaa agacatatgc    6180
gaggtacctt cagatctttg cgccttgctt gctgccaaac ccgaactgga aggaggcctc    6240
tccaccgtcc aacttctgtg tgtgttttc ctcctgtgga gaatgatggg acatgcctgg    6300
acgcccttgg ttgctgttgg gtttttatc ttgaatgagg ttctcccagc tgtactggtc    6360
cggagtgttt tctcctttgg aatgtttgtg ctatcttggc tcacaccatg gtctgcgcaa    6420
gttctgatga tcaggcttct aacagcagct cttaacagga acagattgtc actcgccttt    6480
tacagccttg gtgcagcgac cggttttgtc gcagatctgg cggcaactca agggcacccg    6540
ttgcaggcag taatgaattt aagtacctat gccttcctgc ctcggataat ggtcgtgacc    6600
tcaccagtcc cagtgattgc gtgtggtgtt gtgcacctcc ttgccataat tttgtacttg    6660
tttaagtacc gctgcctgca caatgtcctt gttggcgatg gtgcgttctc tgcggctttc    6720
ttcttgcgat actttgccga ggggaaattg agggaagggg tgtcgcaatc ctgcgggatg    6780
aatcatgagt cgctgactgg tgccctcgct atgagactta atgacgagga cttggatttt    6840
```

```
cttacgaaat ggactgattt taagtgtttt gtttctgcat ccaacatgag gaatgcggcg   6900
ggccagttca tcgaggctgc ctatgctaaa gcacttagaa ttgaacttgc ccagttggtg   6960
caggttgata aggttcgagg tactttggcc aaacttgaag cttttgctga taccgtggca   7020
ccccaactct cgcccggtga cattgttgtt gctcttggcc atacgcctgt tggcggtatc   7080
ttcgacctaa aggttggtag caccaagcat accctccaag ccattgagac cagagttctt   7140
gccgggtcca aaatgaccgt ggcgcgtgtc gttgatccaa cccccacacc cccacccgca   7200
cccgtgccta tccccctttcc accgaaagtt ctggagaatg gtcccaacgc ctgggggggat   7260 gaggatcgtt tgaataagaa gaagaggcgc aagatggaag ccgtcggcat ctttgttatg   7320
ggtggaaaga aatatcagaa attttgggac aagaactccg gtgatgtgtt ttatgaggag   7380
gtccatgata acacagacgc gtgggagtgc ctcagagttg acaaccctgc cgactttgac   7440
cctgagaagg gaactctgtg cgggcatact accattgaag ataagactta cagtgtctac   7500
gcctccccat ctggcaagaa attcctggtc cccgcctacc cagagagcaa aaaaaaccaa   7560
tgggaagctg cgaagctttc cgtggaacag gcccttggca tgatgaatgt cgacggtgaa   7620
ctgacagcca aagaagtgga gaaactgaaa agaataattg acaaactcca gggcctgact   7680
aaggagcagt gtttaaactg ctagccgcca gcggcttgac ccgctgtggt cgcggcggct   7740
tggttattac tgacacagcg gtaaaaatag tcaaatttca caaccggacc ttcaccctag   7800
gacctgtgaa tttaaaagtg gccagtgagg ttgagctaaa agacgcggtc gagcataacc   7860
aacacccggt tgcaagaccg gttgatggtg gtgttgtgct cctgcgctcc gcagttcctt   7920
cgcttataga cgtcttaatc tccggcgctg atgcatctcc caagttactc gcccgccacg   7980
ggccgggaaa cactgggatc gatggcacgc tttgggattt tgaggccgag gccactaaag   8040
aggaaattgc actcagtgcg caaataatac aggcttgtga cattaggcgc ggcgacgcac   8100
ctgaaattgg tcttccttat aagctgtacc ctgtcagggg caaccctgag cgggtaaaag   8160 gagtttttaca gaatacaagg tttggagata taccttataa aaccccccagt gacactggaa   8220 gcccagtgca cgcggctgcc tgcctcacgc ccaatgccac tccggtgact gatgggcgct   8280
ccgtcttggc cacgactatg ccctccggtt ttgagttgta tgtaccgacc attccagcgt   8340
ctgtccttga ttatcttgat tctaggcctg actgccccaa acagttgaca gagcacggct   8400
gtgaggacgc cgcattaaga gacctctcca agtatgactt gtccacccaa ggctttgttt   8460
tacctggagt tcttcgcctt gtgcgtaagt acctgtttgc tcatgtgggt aagtgcccgc   8520
ccgttcatcg gccttccact accctgccaa gaattctat ggctggaata aatgggaaca   8580
ggtttccaac caaggacatc cagagcgtcc ctgaaatcga cgttctgtgc gcacaggccg   8640
ttcgggaaaa ctggcaaact gttacccctt gtaccctcaa gaaacagtat tgtgggaaga   8700
agaagactag gacaatactc ggcaccaata acttcattgc gctggctcac cgggcagcgt   8760
tgagtggtgt cacccagggc ttcatgaaaa aggcgtttaa ctcgcccatt gccctcggta   8820
aaaacaaatt taaagagctt cagactccgg tcttaggcag gtgccttgaa gctgatcttg   8880
catcctgcga tcgctccaca cctgcaattg tccgctggtt tgccgccaat cttctttatg   8940
aacttgcctg tgctgaagag caccagccgt cgtacgtgtt gaactgctgc cacgacctac   9000
tggtcacgca gtccggcgca gtaactaaga gaggtggcct gtcgtctggc gacccgatca   9060
cttctgtgtc caacaccatt tacagcttgg tgatatatgc acaacacatg gtgctcagtt   9120
actttaaaag tggtcaccct catggccttc tgttctacta agaccagctg aagtttgagg   9180
acatgctcaa ggttcaaccc ctgatcgtct attcggacga cctcgtactg tatgccgagt   9240
```

-continued

```
ctcccaccat gccaaactac cactggtggg ttgaacatct gaacctgatg ctgggttttc    9300
agacggaccc aaagaagaca gccataacag actcgccatc atttctaggc tgtaggataa    9360
taaatggacg ccagctcgtc cctaaccgtg acaggattct cgcggccctc gcctaccata    9420
tgaaggcaag caatgtctct gaatactacg cctcggcggc tgcgatactc atggacagct    9480
gtgcttgttt agagtatgat cccgaatggt ttgaagagct tgtagttggg atagcgcagt    9540
gtgcccgcaa ggacggctac agttttcccg gcccgccgtt cttcttgtcc atgtgggaaa    9600
aactcagatc caatcatgag gggaagaagt ccagaatgtg cgggtactgc ggggcccgg     9660
ctccgtacgc cactgcctgt ggcctcgacg tctgtattta ccacacccac ttccaccagc    9720
attgtccagt catcatctgg tgtggccacc cggctggttc tggttcttgt agtgagtgca    9780
aaccccccct agggaaaggc acaagccctc tagatgaggt gttagaacaa gtcccgtata    9840
agcctccacg gactgtaatc atgcatgtgg agcagggtct caccectctt gacccaggca    9900
gataccagac tcgccgcgga ttagtctccg ttaggcgtgg cattagagga aatgaggttg    9960
atctaccaga cggtgattat gctagcaccg ccctactccc tacttgtaaa gagattaaca   10020
tggtcgctgt cgcctctaat gtgttgcgca gcaggttcat catcggcccg cctggtgctg   10080
ggaaaacata ctggctcctt caacaggtcc aggatggtga tgccatttac acgccaactc   10140
accagaccat gctcgatatg attagggctt tggggacgtg ccggttcaac gtcccagcag   10200
gtacgacgct gcaattccct gcccctccc gtaccggccc ttgggttcgc atcctagccg    10260
gcggttggtg tcctggcaag aattccttcc tggatgaagc agcgtattgt aatcaccttg   10320
atgtcttgag gcttcttagc aaaactaccc tcacctgtct gggagattc aaacaactcc    10380
acccagtggg ttttgattct cattgctatg tttttgacat catgcctcag actcaactga   10440
agaccatctg gagatttgga cagaatatct gtgaggccat tcagccagat tacagggaca   10500
aacttgtatc catggtcaac acaaccgtg taacctacgg ggaaaaacct gtcaagtatg    10560
ggcaagtcct cacccttac cacagggacc gagaggacgg cgccatcaca attgactcca    10620
gtcaaggcgc cacatttgat gtggttacac tgcatttgcc cactaaagat tcactcaaca   10680
ggcaaagagc ccttgttgct attaccaggg caagacatgc tgtctttgtg tatgacccac   10740
acaggcaact gcagagcatg tttgatcttc ctgcgaaagg cacacccgtc aacctcgctg   10800
tgcaccgtga cgagcagctg atcgtgctag atagaaataa caaagaatgc acggttgctc   10860
aggctctagg caatggggat aaattcaggg ccacagacaa gcgcgttgta gattctctcc   10920
gcgccatttg tgcagatctg gaagggtcga gctccccgct cccaaggtc gcacacaact    10980
tgggattta tttctcgcct gatttgacac agtttgctaa actcccgta gaacttgcac     11040
cccactggcc cgtggtgaca acccagaaca atgaaaagtg gccagaccgg ttggttgcta   11100
gccttcgccc cgtccataag tatagccgcg cgtgcatcgg tgccggctac atggtgggcc   11160
cctcagtgtt tctgggcacc cctggggttg tgtcatacta tctcacaaaa tttgtcaggg   11220
gcgaggctca aatgcttccg gagacagtct tcagcaccgg ccgaattgag gtagattgcc   11280
gtgagtatct cgatgaccgg gagcgagaaa ttgctgagtc cctcccccat gctttcattg   11340
gcgacgtcaa aggcactacc gttggaggat gtcaccatgt cacctccaaa taccttccgc   11400
gcttccttcc caaggaatca gtcgcggtag tcggggtttc aagcccggg aaagccgcaa    11460
aagcagtttg cacattaaca gatgtgtatc tcccagatct cgaagcttac ctccacccag   11520
agacccagtc caagtgctgg aaaatgatgt tggacttcaa ggaagttcga ctgatggtct   11580
ggaaggacaa gacggcctat tttcaacttg aaggccgcca tttcacctgg taccagcttg   11640
```

```
caagctatgc ctcgtacatc cgagttcctg ttaactctac ggtgtatttg gacccctgca   11700
tgggccctgc cctttgcaac agaagagttg tcgggtccac tcattgggga gctgacctcg   11760
cagtcacccc ttatgattac ggtgccaaaa tcatcctgtc tagtgcatac catggtgaaa   11820 tgcccctgg gtacaaaatc ctggcgtgcg cggagttctc gcttgacgat ccagtgaggt   11880
acaaacacac ctgggggttt gaatcggata cagcgtatct gtacgagttc accggaaacg   11940
gtgaggactg ggaggattac aatgatgcgt tcgtgcgcg ccagaaaggg aaaatttata   12000
aggccactgc caccagcatg aggtttcatt ttccccgggg ccctgtcatt gaaccaactt   12060
taggcctgaa ttgaaatgaa atgggtcca tgcaaagcct ctttgacaaa attggccaac   12120
ttttcgtgga tgctttcacg gaattttttgg tgtccattgt tgatatcatc atatttttgg   12180
ccattttgtt tggctttacc atcgctggct ggctggtggt cttctgcatc cgattggttt   12240 gctccgcgt actccgtgcg cgccctacca ttcaccctga gcaattacag aagatcctat   12300
gaggcctttc tttctcagtg ccaggtggat attcccacct ggggaactag acatcccctg   12360
gggatgcttt ggcaccataa ggtgtcaacc ctgattgatg aaatggtgtc gcgtcggatg   12420
taccgcacca tggaaaaagc aggacaggct gcctggaaac aggtggtgag cgaggccacg   12480
ctgtctcgca ttagtggttt ggatgtggtg gctcattttc agcatcttgc cgccattgaa   12540
gccgagacct gtaaatattt ggcctctcgg ctgcccatgc tacacaatct gcgcatgaca   12600
gggtcaaatg taaccatagt gtataatagt actttgaatc aggtgtttgc tatttttcca   12660 accctggat cccggccaaa gcttcatgat tttcagcaat ggctaatagc tgtgcactcc   12720
tccatatttt cctccgttgc ggcttcttgt actctttttg ttgtgctgtg gttgcggatt   12780
ccaatgctac gtactgtttt tggttttccgc tggttagggg caattttttcc ttcgaactca   12840 cggtgaatta cacggtgtgt ccgccttgcc tcacccggca agcagccgct gaggtctacg   12900
aaccaggcag gtctctttgg tgcaggatag ggcatgaccg atgtagtgag gaagaccatg   12960
acgatctagg gttcatggtt ccgtctggcc tctccagcga aggccacttg accagtgttt   13020
acgcctggtt ggcgttcctg tccttcagct acacggccca gttccatccc gagatatttg   13080
ggatagggaa tgtgagtcaa gtttatgttg acatcaagca ccaattcatc tgcgccgttc   13140
acgacgggga gaacgccacc ttgcctcgtc atgacaatat ttcagccgta tatcagacct   13200
actaccaaca tcaagtcgac ggcggcaatt ggtttcacct agaatggctg cgccccttct   13260
tttcctcttg gttggtttta aatgtttctt ggtttctcag gcgttcgcct gcaagccatg   13320
tttcagttca agtctttcgg acatcaaaac caacacaacc gcagcatcag gctttgttgt   13380
cctccaggac atcagctgcc ttaggcatgg cgactcgtcc tctcagacga ttcgcaaaag   13440
ctctcagtgc cgcgcggcga tagggacgcc cgtgtacatc actgtcacag ccaatgtcac   13500
agatgagaat tatttacatt cttctgatct ccttatgctt tcttcttgcc ttttctatgc   13560
ttctgagatg agtgaaaagg gattcaaggt gatgtttggc aatgtgtcag gcatcgtggc   13620
tgtgtgtgtc aactttacca gctacgtcca acatgtcaag gagttaccc aacgctcctt   13680 ggtggtcgat catgtgcggc tgctccattt catgacacct gagaccatga ggtgggcaac   13740
cgttttagcc tgtttccttg ccatcttact ggcaatttga atgttcaagt atgttgggga   13800
gatgcttgac cgcgggctgt tgctcgcgat tgctttcttt gtggtgtatc gtgccatttt   13860
gttttgctgc gctcgtcaac gccaacagca acagcagctc tcatcttcag ttaatttaca   13920
acttgacgct atgtgagctg aatggcacag attggctgaa agacaaattt gattgggcat   13980
tggagacttt tgtcatcttt cccgtgttga ctcacattgt ctcatatagt gcactcacca   14040
```

-continued

```
ctagccattt ccttgacaca gtcggtctgg ttactgtgtc tactgccggg ttctaccacg    14100
ggcggtatgt tctgagtagc atctacgcgg tctgcgctct ggccgcattg acttgcttcg    14160
tcattaggct tgcgaagaac tgcatgtcct ggcgctactc ttgtaccaga tatactaact    14220
tccttctgga cactaagggc agactctatc gctggcggtc gcccgttatc atagagaaag    14280
ggggtaaggt tgaggtcgaa ggtcacctga tcgacctcaa aagagttgtg cttgatggtt    14340
ccgtggcaac ccctttatac agagtttcag cggaacaatg gggtcgtctt tagacgactt    14400
ttgctatgat agcacggctc cacaaaaggt gcttttggcg ttttccatta cctacacgcc    14460
agtgatgata tatgctctaa aggtaagtcg cggccgactt ttagggcttc tgcaccttt     14520
gatctttctg aattgtactt ttaccttcgg gtacatgaca tgcgtgcact ttaatagcac    14580
aaataaggtc gcgctcacta tgggagcagt agttgcactt ctttgggggg tgtactcagc    14640
catagaaacc tggaagttca tcacctccag atgtcgtttg tgcttgctag gccgcaagta    14700
cattctggcc cccgcccacc acgtcgaaag tgccgcgggc tttcatccga tcgcggcaaa    14760
tgataaccac gcatttgtcg tccggcgtcc cggctccact acggttaacg gcacattggt    14820
gcccgggttg aaaagcctcg tgttgggtgg cagaaaagct gttaaacagg gagtggtaaa    14880
ccttgtcaaa tatgccaaat aacaacggca agcagcaaaa gaaaagagg gggaatggcc    14940
agccagtcaa tcagctgtgc cagatgctgg gtaagatcat cgcccagcaa aaccagtcca    15000
gaggcaaggg accggggaag aaaattaaga ataaaaaccc ggagaagccc catttttcctc   15060
tagcgactga agatgacgtc aggcatcact tcacccctag tgagcggcaa ttgtgtctgt    15120
cgtcgatcca gactgccttt aaccagggcg ctggaacctg taccctatca gattcaggta    15180
ggataagtta cactgtggag tttagtttgc gacgcatca tactgtgcgc ctgatccgcg     15240
tcacagcgcc atcatcagcg taatgggctg gcattcctta agcacctcag tgttagaatt    15300
ggaagaatgt gtggtgaatg gcactgattg gcactgtgcc tctaagtcac ctattcaatt    15360
agggcgaccg tgtgggggtt aagtttaatt ggcgagaacc atgcggccga aattaaaaaa    15420
aaaa                                                                 15424
```

<210> SEQ ID NO 2
<211> LENGTH: 15424
<212> TYPE: DNA
<213> ORGANISM: Porcine reproductive and respiratory syndrome virus

<400> SEQUENCE: 2

```
tcgcccgggc aggtgttggc tctatgcctt ggcatttgta ttgtcaggag ctgcgaccat      60
tggtacagcc caaaactagc tgcacagaaa acgcccttct gtgacagccc tcttcagggg    120
agcttagggg tctgtcccta gcaccttgct tccggagttg cactgcttta cggtctctcc    180
aaccctttaa ccatgtctgg gatacttgat cggtgcacgt gcaccccaa tgccagggtg     240
tttatggcgg agggccaagt ctactgcaca cgatgtctca gtgcacggtc tctccttcct    300
ctgaatctcc aagttcctga gcttggagtg ctgggcctat tttacaggcc cgaagagcca    360
ctccgtggacgttgccacgt gcattcccc actgttgagt gctcccccgc cggggcctgc      420
tggctttctg cgatctttcc aattgcacga atgaccagtg gaaacctgaa ctttcaacaa    480
agaatggtgc gggtcgcagc tgagatttac agagccggcc agctcacccc tgcagtcttg    540
aaggctctac aagtttatga acggggttgc cgctggtacc ctatagtcgg acctgtccct    600
ggagtggccg ttttttgccaa ctccctacat gtgagtgata aacctttccc gggagcaact    660
catgtgctaa ccaacctgcc actcccgcag aggcctaagc ctgaagactt tgcccttttt    720
```

```
gagtgtgcta tggctgacgt ctatgatatt ggtcatggcg ccgtcatgta tgtggccaaa    780
gggaaagtct cctgggcccc tcgtggcggg gatgaggcga aatttgaaac tgtccctagg    840
gagttgaagt tgatcgcgaa ccaactccac atctccttcc cgccccacca cgcagtggac    900
atgtctaagt ttgtgttcat agccctgggg agtggtgtct ctatgcgggt cgagtgccca    960
cacggctgtc tccccgctaa tactgtccct gaaggtaact gctggtggcg cttgttttgac   1020 tcgctcccac tggacgttca gaacaaagaa attcgccgtg ccaaccaatt cggctatcaa   1080
accaagcatg gtgtcgctgg caagtaccta caacggaggc tgcaagctaa tggtctccga   1140
gcagtgactg atacagatgg acccattgtc gtacagtatt tctctgttag ggagagctgg   1200
atccgccact tcagactggc ggaagagcct agcctccctg ggtttgaaga cctcctcaga   1260
ataagggtag agcccaatac gtcgccattg agtgacaagg gtggaaaaat cttccggttt    1320
ggcagtcaca aatggtacgg tgctggaaag agagcaagga aagcacgctc tggtatgacc   1380
accacagtcg ctcaccgcgc cttgcccgct cgtgaaatcc agcaagccaa aaagcacgag   1440
gatgccggcg ctgataaggc tgtgcatctc aggcactatt ctccgcctgc cgacgggaac   1500
tgtggttggc actgcatttc cgccatcgcc aaccgaatgg tgaattccaa atttgaaact    1560
actcttcccg agagggtgag accttcagat gactgggcta ctgacgagga ccttgtgaac   1620
accatccaaa ttctcaagct ccctgcgcc ttggacagga cggtgcttg tgttggcgcc   1680 aaatacgtgc ttaagctgga aggcgagcat tggactgtct ctgtgaccct gggatgtcc   1740 ccttctttgc tccccttga atgtgttcag ggctgttgtg agcataagag cggacttggt   1800
cccccagatg cggtcgaagt tttcggattt gaccctgcct gccttgaccg actggctgag   1860
gtaatgcact gcctagcag tgtcatccca gctgctctgg ccgaaaatgc cggcgacccc   1920
aactgtccgg cttccccggt cactactgtg tggactgttt cacaattctt tgcccgccac   1980
agaggaggag agcaccctga tcaggtgcgc ttaggaaaaa tcatcagcct ttgtcaagtt   2040
gttgaggaat gctgttgcca tcagaataaa accaaccggg ccaccccgga gaggttgcg    2100 gcaaggattg atcagtacct ccatggtgca acaagtcttg aagaatgctt gattaggctt   2160
gagagggttt gcccgccgag cgctgcggac accttctttg attggaatgt tgtgctccct   2220
ggggttgggg cttcaactca gacaaccaaa cagctccatg tcaaccagtg ccgcgctctg   2280
gttcctgtcg tgactcaaga gcctttggac aaagactcag tccctctgac cgccttctcg   2340
ctgtccaatt gctactatcc tgcacaaggt gacgaggttc gtcaccgtga gaggctaaac   2400
tccgtactct ctaagctgga gggggttgtt cgtgaggaat atgggctcac gccaactgaa   2460
cctggcccgc gacccgcact accgaacggg ctcgtcgaac ttaaagacca gatggaggag   2520
gatctgctga aactagtcaa cgcccaggca acttcagaaa tgatggcctg gcagccgag    2580 caggttgatc tgaaagcttg ggtcaaaaac tacccacggt ggacaccgcc accccctcca   2640
ccaagagttc agcctcgaaa aacaaagtct gtcaagagct tgccagggaa caaacctgtc   2700
cccgctccac gcaggaaggt cagatctgat tgtggcagcc cgattttgat gggcgacaat   2760
gttcctgacg gtcgggaaga tttgactgtt ggtggccccc ttgatctttc gacaccatcc   2820
gagccgatga cacctctgag tgagcctgca cttatgcccg cgttgcaata tatttctagg   2880
ccagtgacat ctttgagtgt gctggcccca gttcctgcac cgcgtagaac tgtgtcccga   2940
ccggtgacgc ccttgagtga gccaattttt gtgtctgcac cgcgacacaa atttcagcag   3000
gtggaagaag cgaatctggc ggcaacaacg ctgacgcacc aggacgaacc tctagatttg   3060
tctgcatcct cacagactga atatgaggct tctcccctaa caccactgca gaacatgggt   3120
```

```
attctggagg tggggggggca agaagctgag gaagttctga gtgaaatctc ggatacactg    3180
aatgacatca accctgcacc tgtgtcatca agcagctccc tgtcaagtgt taagatcaca    3240
cgcccaaaac actctgctca agccatcatt gactcgggcg ggccctgcag tgggcatctc    3300
cgaagggaaa aagaagcatg cctcagcatc atgcgtgagg cttgtgatgc ggctaagctt    3360
agtgaccctg ccacgcagga atggctttct cgcatgtggg atagggttga catgctgact    3420
tggcgcaaca cgtctgctta ccaggcgttc cgcatcttag atggtaggtt tgagtttctc    3480
ccaaagatga tactcgagac accgccgccc taccgtgtg ggtttgtgat gctgcctcac    3540
acgcctgcac cttccgtggg tgcagagagt gaccttacca ttggttcagt cgccactgaa    3600
gatgttccac gcatcctcgg gaaaatagaa aacgccggcg agatgcccaa ccaggggctc    3660
ttgacatcct tcggggaaga accggtgtgc gaccaacctg tcaaggactc ctggatgtcg    3720
tcgcgggggt ttgacgagag cacaacggct ccgtccgctg gtacaggtgg tgctgactta    3780
cccaccgatt tgccaccttc agatggtttg gatgcggacg agtgggggcc gttacggacg    3840
gtaagaaaga aagctgaaag gctcttcgac caattgagcc gtcaggtttt taacctcgtc    3900
tcccatctcc ctgttttctt ctcacacctc ttcaaatctg acagtggtta ttctccgggt    3960 gattgggtt ttgcagcttt tactttattt tgcctctttt tgtgttacag ctacccattc    4020
tttggttttg ttccctctt gggtgttttt tctgggtctt ctcggcgtgt gcgcatgggg    4080
gtttttggct gttggttggc ttttgctgtt ggcctgttca agcctgtgtc cgacccagtc    4140
ggcactgctt gtgagtttga ctcgccagag tgtaggaacg tccttcattc ttttgagctt    4200
ctcaaacctt gggaccctgt tcgcagcctt gttgtgggcc ccgtcggtct cggccttgcc    4260
attcttggca ggtactggg cggggcacgc tacatctggc attttttgct taggcttggc    4320
attgttgcag attgtatctt ggctggagct tatgtgcttt ctcaaggtag gtgtaaaaag    4380
tgctggggat cttgtgtaag aactgctcct aatgaaatcg ccttcaacgt gttcccttt    4440 acgcgtgcga ccaggtcgtc actcatcgac ctgtgcgatc ggttttgtgc gccaaaaggc    4500 atggaccccca tttttcctcgc tactgggtgg cgcgggtgct ggaccggccg aagtcccatt    4560
gagcaaccct ctgaaaaacc catcgcgttc gcccagttgg atgaaaagag gattacggct    4620
agaactgtgg gcgctcagcc ttatgatcct aaccaagccg taaagtgctt gcgggtgtta    4680
caggcgggtg gggcgatagt ggccgaggca gtcccaaaag tggtcaaggt ttccgctatt    4740
ccattccgag ctccctttt tcccaccgga gtgaaggttg atcctgagtg caggatcgtg    4800
gtcgaccccg acactttac tacagctctc cggtctggtt actccaccac aaacctcgtc    4860
cttggtgtgg gggactttgc ccaactgaat ggattaaaaa tcaggcaaat ttccaagccc    4920
tcgggaggag gcccgcacct cattgctgcc ctgcatgttg cttgctcgat ggcgttgcac    4980
atgcttgctg gagtttatgt aactgcagtg gggtcttgcg gtaccggcac caacgatccg    5040
tggtgcacta acccattcgc cgtccctggc tacggacctg gctccctctg cacgtccaga    5100
ttgtgcatct cccaacatgg ccttaccctg cccttgacag cacttgtggc aggattcggt    5160
cttcaggaaa ttgccctagt cgttttgatt ttcgtttcca tcgaggcat ggctcatagg    5220 ttgagttgta aggctgatat gctgtgcgtc ttacttgcaa tcgccagcta tgtttgggta    5280 cccccttacct ggttgctctg tgtgtttcct tgctggttgc gctggttctc tttgcacccct    5340 ctcaccattc tatggttggt gttttttcttg atgtctgtaa atatgccttc gggaatctta    5400
accgtggtgt tattggttgc tctttggctt ctaggccgtt atactaatgt tgttggtctt    5460
gttaccccct atgatattca tcattacacc aatggccccc gcggtgttgc cgccttggct    5520
```

```
accgcaccag atgggactta cttggccgct gtccgccgcg ctgcgttgac tggccgcacc    5580
gtgctgttta ccccgtctca gcttgggtcc cttcttgagg gcgctttcag aactcgaaag    5640
ccctcactga acaccgtcaa tgtggtcggg tcctccatgg gctctggcgg agtgttcact    5700
atcgatggga aaattaagtg cgtgactgcc gcacatgtcc ttacgggtaa ttcagccagg    5760
gtttccgggg tcggcttcaa tcaaatgctt gactttgatg taaaggggga cttcgccata    5820
gctgattgcc cgaattggca aggggctgct cctaagaccc aattctgcga ggatggatgg    5880
actggccgcg cctattggct gacatcctct ggcgtcgaac ccggtgtcat gggaatggga    5940
ttcgccttct gcttcaccgc gtgcggcgat tccgggtccc cagtgatcac cgaagccggt    6000
gagcttgtcg gcgttcacac aggatcaaac aaacaaggag gaggcattgt tacgcgcccc    6060
tctggccagt tttgcaatgt ggcacccatc aagctgagcg aattaagtga gttctttgct    6120
ggacctaagg tcccgctcgg tgatgtgaag gttggcagcc acataattaa agacatatgc    6180
gaggtacctt cagatctttg cgccttgctt gctgccaaac ccgaactgga aggaggcctc    6240
tccaccgtcc aacttctgtg tgtgtttttc ctcctgtgga gaatgatggg acatgcctgg    6300
acgcccttgg ttgctgttgg gttttttatc ttgaatgagg ttctcccagc tgtactggtc    6360
cggagtgttt tctcctttgg aatgtttgtg ctatcttggc tcacaccatg gtctgcgcaa    6420
gttctgatga tcaggcttct aacagcagct cttaacagga acagattgtc actgcctttt    6480
tacagccttg gtgcagcgac cggttttgtc gcagatctgg cggcaactca agggcacccg    6540
ttgcaggcag taatgaattt aagtaccstat gccttcctgc ctcggataat ggtcgtgacc    6600
tcaccagtcc cagtgattgc gtgtggtgtt gtgcacctcc ttgccataat tttgtacttg    6660
tttaagtacc gctgcctgca caatgtcctt gttggcgatg gtgcgttctc tgcggctttc    6720
ttcttgcgat actttgccga ggggaaattg agggaagggg tgtcgcaatc ctgcgggatg    6780
aatcatgagt cgctgactgg tgccctcgct atgagactta atgacgagga cttggatttt    6840
cttacgaaat ggactgattt taagtgtttt gtttctgcat ccaacatgag gaatgcggcg    6900
ggccagttca tcgaggctgc ctatgctaaa gcacttagaa ttgaacttgc ccagttggtg    6960
caggttgata aggttcgagg tactttggcc aaacttgaag cttttgctga taccgtggca    7020
ccccaactct cgcccggtga cattgttgtt gctcttggcc atacgcctgt ggcggtatc     7080
ttcgacctaa aggttggtag caccaagcat accctccaag ccattgagac cagagttctt    7140
gccgggtcca aaatgaccgt ggcgcgtgtc gttgatccaa ccccccacac cccacccgca    7200
cccgtgccta tccccccttcc accgaaagtt ctggagaatg gtcccaacgc ctgggggat    7260
gaggatcgtt tgaataagaa gaagaggcgc aggatggaag ccgtcggcat cttttgttatg    7320
ggtggaaaga aatatcagaa attttgggac aagaactccg gtgatgtgtt ttatgaggag    7380
gtccatgata acacagacgc gtgggagtgc ctcagagttg acaaccctgc cgactttgac    7440
cctgagaagg gaactctgtg cggccatact accattgaag ataagactta cagtgtctac    7500
gcctccccat ctggcaagaa attcctggtc cccgtctacc cagagagcaa aaaaaaccaa    7560
tgggaagctg cgaagctttc cgtggaacag gcccttggca tgatgaatgt cgacggtgaa    7620
ctgacagcca aagaagtgga gaaactgaaa agaataattg acaaactcca gggcctgact    7680
aaggagcagt gtttaaactg ctagccgcca gcggcttgac ccgctgtggt cgcggcggct    7740
tggttgttac tgagacagcg gtaaaaatag tcaaatttca caaccggacc ttcaccctag    7800
gacctgtgaa tttaaaagtg gccagtgagg ttgagctaaa agacgcggtc gagcataacc    7860
aacacccggt tgcaagaccg gttgatggtg tgttgtgct cctgcgctcc gcagttcctt    7920
```

-continued

| | |
|---|---|
| cgcttataga cgtcttaatc tccggcgctg atgcatctcc caagttactc gcccgccacg | 7980 |
| ggccgggaaa cactgggatc gatggcacgc tttgggattt tgaggccgag gccactaaag | 8040 |
| aggaaattgc actcagtgcg caaataatac aggcttgtga cattaggcgc ggcgacgcac | 8100 |
| ctgaaattgg tcttccttat aagctgtacc ctgtcagggg caaccctgag cgggtaaaag | 8160 |
| gagtttttaca gaatacaagg tttgagaca taccttataa acccccagt gacactggaa | 8220 |
| gcccagtgca cgcggctgcc tgcctcacgc ccaatgccac tccggtgact gatgggcgct | 8280 |
| ccgtcttggc cacgactatg ccctccggtt ttgagttgta tgtaccgacc attccagcgt | 8340 |
| ctgtccttga ttatcttgat tctaggcctg actgccccaa acagttgaca gagcacggct | 8400 |
| gtgaggacgc cgcattaaga gacctctcca agtatgactt gtccacccaa ggctttgttt | 8460 |
| tacctggagt tcttcgcctt gtgcgtaagt acctgtttgc tcatgtgggt aagtgcccgc | 8520 |
| ccgttcatcg gccttccact taccctgcca agaattctat ggctggaata atgggaaca | 8580 |
| ggtttccaac caaggacatc cagagcgtcc ctgaaatcga cgttctgtgc gcacaggccg | 8640 |
| tgcgggaaaa ctggcaaact gttacccctt gtaccctcaa gaaacagtat tgtgggaaga | 8700 |
| agaagactag gacaatactc ggcaccaata acttcattgc gctggcccac cgggcagcgt | 8760 |
| tgagtggtgt cacccagggc ttcatgaaaa aggcgtttaa ctcgcccatt gccctcggta | 8820 |
| aaaacaaatt taaagagctt cagactccgg tcttaggcag gtgccttgaa gctgatcttg | 8880 |
| catcctgcga tcgctccaca cctgcaattg tccgctggtt tgccgccaat cttctttatg | 8940 |
| aacttgcctg tgctgaagag cacctgccgt cgtacgtgtt gaactgctgc cacgacctac | 9000 |
| tggtcacgca gtccggcgca gtaactaaga gaggtggcct gtcgtctggc gacccgatca | 9060 |
| cttctgtgtc caacaccatt tacagcttgg tgatatatgc acaacacatg gtgctcagtt | 9120 |
| actttaaaag tggtcaccct catggccttc tgtttctaca agaccagctg aagtttgagg | 9180 |
| acatgctcaa ggttcaaccc ctgatcgtct attcggacga cctcgtactg tatgccgagt | 9240 |
| ctcccaccat gccaaactac cactggtggg ttgaacatct gaacctgatg ctgggttttc | 9300 |
| agacggaccc aaagaagaca gccataacag actcgccatc atttctaggc tgtaggataa | 9360 |
| taaatggacg ccagctcgtc cctaaccgtg acaggattct cgcggccctc gcctaccata | 9420 |
| tgaaggcaag caatgtctct gaatactacg cctcggcggc tgcgatactc atggacagct | 9480 |
| gtgcttgttt agagtatgat cccgaatggt ttgaagagct tgtagttggg atagcgcagt | 9540 |
| gtgcccgcaa ggacggctac agttttcccg gcccgccgtt cttcttgtcc atgtgggaaa | 9600 |
| aactcagatc caatcatgag gggaagaagt ccagaatgtg cgggtactgc ggggcccgg | 9660 |
| ctccgtacgc cactgcctgt ggcctcgacg tctgtattta ccacccac ttccaccagc | 9720 |
| attgtccagt catcatctgg tgtggccacc cggctggttc tggttcttgt agtgagtgca | 9780 |
| aacccccct agggaaaggc acaagccctc tagatgaggt gttagaacaa gtcccgtata | 9840 |
| agcctccacg gactgtaatc atgcatgtgg agcagggtct caccctctt gacccaggca | 9900 |
| gataccagac tcgccgcgga ttagtctccg ttaggcgtgg cattagagga atgaggttg | 9960 |
| atctaccaga cggtgattat gctagcaccg ccctactccc tacttgtaaa gagattaaca | 10020 |
| tggtcgctgt cgcctctaat gtgttgcgca gcaggttcat catcggcccg cctggtgctg | 10080 |
| ggaaaacata ctggctcctt caacaggtcc aggatggtga tgtcatttac acgccaactc | 10140 |
| accagaccat gctcgatatg attagggctt tggggacgtg ccggttcaac gtcccagcag | 10200 |
| gtacgacgct gcaattccct gcccctccc gtaccggccc ttgggttcgc atcctagccg | 10260 |
| gcggttggtg tcctggcaag aattccttcc tggatgaagc agcgtattgt aatcaccttg | 10320 |

```
atgtcttgag gcttcttagc aaaactaccc tcacctgtct gggagatttc aaacaactcc    10380
acccagtggg ttttgattct cattgctatg tttttgacat catgcctcag actcaactga    10440
agaccatctg gagatttgga cagaatatct gtgatgccat tcagccagat tacagggaca    10500
aacttgtatc catggtcaac acaacccgtg taacctacgt ggaaaaacct gtcaagtatg    10560
ggcaagtcct cacccttac cacagggacc gagaggacgg cgccatcaca attgactcca    10620
gtcaaggcgc acatttgat gtggttacac tgcatttgcc cactaaagat tcactcaaca    10680
ggcaaagagc ccttgttgct attaccaggg caagacatgc tatctttgtg tatgacccac    10740
acaggcaact gcagagcatg tttgatcttc ctgcgaaagg cacacccgtc aacctcgctg    10800
tgcaccgtga cgagcagctg atcgtgctag atagaaataa caaagaatgc acggttgctc    10860
aggctctagg caatggggat aaattcaggg ccacagacaa gcgcgttgta gattctctcc    10920
gcgccatttg tgcagatctg gaagggtcga gctccccgct ccccaaggtc gcacacaact    10980
tgggatttta tttctcgcct gatttgacac agtttgctaa actcccggta gaacttgcac    11040
cccactggcc cgtggtgaca acccagaaca atgaaaagtg gccagaccgg ttggttgcta    11100
gccttcgccc cgtccataag tatagccgcg cgtgcatcgg tgccggctac atggtgggcc    11160
cctcagtgtt tctgggcacc cctggggttg tgtcatacta tctcacaaaa tttgtcaggg    11220
gcgaggctca aatgcttccg gagacagtct tcagcaccgg ccgaattgag gtagattgcc    11280
gtgagtatct tgatgaccgg gagcgagaaa ttgctgagtc cctcccccat gctttcattg    11340
gcgacgtcaa aggcactacc gttggaggat gtcaccatgt cacctccaaa taccttccgc    11400
gcttccttcc caaggaatca gtcgcggtag tcggggtttc aagccccggg aaagccgcaa    11460
aagcagtttg cacattaaca gatgtgtatc tcccagatct cgaagcttac ctccacccag    11520
agacccagtc caagtgctgg aaaatgatgt tggacttcaa ggaagttcga ctgatggtct    11580
ggaaggacaa gacggcctat tttcaacttg aaggccgcca tttcacctgg taccagcttg    11640
caagctatgc ctcgtacatc cgagttcctg ttaactctac ggtgtatttg gaccccctgca    11700
tgggccctgc cctttgcaac agaagagttg tcgggtccac tcattgggga gctgacctcg    11760
cagtcacccc ttatgattac ggtgccaaaa tcatcctgtc tagtgcatac catggtgaaa    11820
tgcccccctgg gtacaaaatc ctggcgtgcg cggagttctc gcttgacgat ccagtgaggt    11880
acaaacacac ctgggggttt gaatcggata cagcgtatct gtacgagttc accggaaacg    11940
gtgaggactg ggaggattac aatgatgcgt tcgtgcgcg ccagaaaggg aaaatttata    12000
aggccactgc caccagcatg aggtttcatt ttccccccggg ccctgtcatt gaaccaactt    12060
taggcctgaa ttgaaatgaa atggggtcca tgcaaagcct cttttgacaaa attggccaac    12120
tttttgtgga tgctttcacg gaatttttgg tgtccattgt tgatatcatc atatttttgg    12180
ccatttttgtt tggctttacc atcgctggct ggctggtggt cttctgcatc cgattggttt    12240
gctccgcggt actccgtgcg cgccctacca ttcaccctga gcaattacag aagatcctat    12300
gaggcctttc tttctcagtg ccaggtggat attcccacct ggggaactag acatcccctg    12360
gggatgtttt ggcaccataa ggtgtcaacc ctgattgatg aaatggtgtc gcgtcggatg    12420
taccgcacca tggaaaaagc aggacaggct gcctggaaac aggtggtgag cgaggccacg    12480
ctgtctcgca ttagtggttt ggatgtgtg gctcattttc agcatcttgc cgccattgaa    12540
gccgagacct gtaaatattt ggcctctcgg ctgcccatgc tacacaatct cgcgcatgaca    12600
gggtcaaatg taaccatagt gtataatagt actttgaatc aggtgtttgc tatttttcca    12660
accctggat cccggccaaa gcttcatgat tttcagcaat ggctaatagc tgtgcactcc    12720
```

```
tccatatttt cctccgttgc ggcttcttgt actcttttg ttgtgctgtg gttgcggatt    12780
ccaatactac gtactgtttt tggtttccgc tggttagggg caattttcc ttcgaactca    12840 cggtgaatta cacggtgtgt ccgccttgcc tcacccggca agcagccgct gaggtctacg    12900
aaccaggcag gtctctttgg tgcaggatag ggcatgaccg atgtagtgag gacgaccatg    12960
acgatctagg gttcatggtt ccgcctggcc tctccagcga aggccacttg accagtgttt    13020
acgcctggtt ggcgttcctg tccttcagct acacggccca gttccatccc gagatatttg    13080
ggatagggaa tgtgagtcaa gtttatgttg acatcaagca ccaattcatc tgcgccgttc    13140
acgacgggga gaacgccacc ttgcctcgtc atgacaatat ttcagccgta tttcagacct    13200
actaccaaca tcaagtcgac ggcggcaatt ggtttcacct agaatggctg cgccccttct    13260
tttcctcttg gttggttttta aatgtttctt ggtttctcag gcgttcgcct gcaagccatg    13320
tttcagttca agtctttcgg acatcaaaac caacactacc gcagcatcag gctttgttgt    13380
cctccaggac atcagctgcc ttaggcatgg cgactcgtcc tctcagacga ttcgcaaaag    13440
ctctcagtgc cgcgcggcga tagggacgcc cgtgtacatc actgtcacag ccaatgtcac    13500
agatgagaat tatttacatt cttctgatct ccttatgctt tcttcttgcc ttttctatgc    13560
ttctgagatg agtgaaaagg gattcaaggt gatatttggc aatgtgtcag gcatcgtggc    13620
tgtgtgtgtc aactttacca gctacgtcca acatgtcaag gagtttaccc aacgctcctt    13680
ggtggtcgat catgtgcggc tgctccattt catgacacct gagaccatga ggtgggcaac    13740
cgttttagcc tgttttttg ccatcttact ggcaatttga atgttcaagt atgttgggga    13800
gatgcttgac cgcgggctgt tgctcgcgat tgctttcttt gtggtgtatc gtgccatttt    13860
gttttgctgc gctcgtcaac gccaacagca acagcagctc tcatcttcag ttgatttaca    13920
acttgacgct atgtgagctg aatggcacag attggctgaa agacaaattt gattgggcag    13980 tggagactt tgtcatcttt cccgtgttga ctcacattgt ctcatatggt gcactcacca    14040
ctagccattt ccttgacaca gtcggtctgg ttactgtgtc taccgccggg ttctaccacg    14100
ggcggtatgt tctgagtagc atctacgcgg tctgcgctct ggccgcattg atttgcttcg    14160
tcattaggct tgcgaagaac tgcatgtcct ggcgctactc ttgtaccaga tatactaact    14220
tccttctgga cactaagggc agactctatc gctggcggtc gcccgttatc atagagaaag    14280
ggggtaaggt tgaggtcgaa ggtcacctga tcgacctcaa aagagttgtg cttgatggtt    14340
ccgtggcaac ccctttaacc agagtttcag cggaacaatg gggtcgtctt tagacgactt    14400
ttgctatgat agcacggctc cacaaaaggt gcttttggcg ttttccatta cctacacgcc    14460
agtgatgata tatgctctaa aggtaagtcg cggccgactt ttagggcttc tgcaccttt    14520 gatctttctg aattgtactt ttaccttcgg gtacatgaca ttcgtgcact taatagcac    14580 aaataaggtc gcgctcacta tgggagcagt agttgcactt ctttgggggg tgtactcagc    14640
catagaaacc tggaagttca tcacctccag atgccgtttg tgcttgctag gccgcaagta    14700
cattctggcc cccgcccacc acgtcgaaag tgccgcgggc tttcatccga tcgcggcaaa    14760
tgataaccac gcatttgtcg tccggcgtcc cggctccact acggttaacg gcacattggt    14820
gcccgggttg aaaagcctcg tgttgggtgg cagaaaagct gttaaacagg gagtggtaaa    14880
ccttgtcaaa tatgccaaat aacaacggca agcagcaaaa gaaaagagg gggaatggcc    14940 agccagtcaa tcagctgtgc cagatgctgg gtaagatcat cgcccagcaa aaccagtcca    15000
gaggcaaggg accggggaag aaaattaaga ataaaaaccc ggagaagccc catttttctc    15060
tagcgactga agatgacgtc aggcatcact tcacccctag tgagcggcaa ttgtgtctgt    15120
```

-continued

| | |
|---|---|
| cgtcgatcca gactgccttt aaccagggcg ctggaacctg taccctatca gattcaggta | 15180 |
| ggataagtta cactgtggag tttagtttgc cgacgcatca tactgtgcgc ctgatccgcg | 15240 |
| tcacagcgcc atcatcagcg taatgggctg cattccttta agcacctcag tgttagaatt | 15300 |
| ggaagaatgt gtggtgaatg gcactgattg gcactgtgcc tctaagtcac ctattcaatt | 15360 |
| agggcgaccg tgtgggggtt aagtttaatt ggcgagaacc atgcggccga aattaaaaaa | 15420 |
| aaaa | 15424 |

<210> SEQ ID NO 3
<211> LENGTH: 15413
<212> TYPE: RNA
<213> ORGANISM: Porcine reproductive and respiratory syndrome virus

<400> SEQUENCE: 3

| | |
|---|---|
| augacguaua ggusuuggcu cuaugccuug gcauuuguau ugucaggagc ugcgaccauu | 60 |
| ggcacagccc aaaacuagcu gcacagaaaa cgcccuucug ugcagcccu cuucagggga | 120 |
| gcuuagggu cugucccuag caccuugcuu ccggaguugc acugcuuuac ggucucucca | 180 |
| acccuuuaac caugucuggg uacuugauc ggugcacgug cacccccaau gccagggugu | 240 |
| uuauggcgga gggccaaguc uacugcacac gaugucucag ugcacggucu cuccuuccuc | 300 |
| ugaaucucca aguccugag cuggagugc ugggccuauu uuacaggccc gaagagccac | 360 |
| uccgguggac guugccacgu gcauucccca cuguugagug ucccccgcc ggggccugcu | 420 |
| ggcuuucugc gaucuuucca auugcacgaa ugaccaguggaaaccugaac uucaacaaa | 480 |
| gaaugguggcg ggucgcagcu gagauuuaca gagccggcca gcucaccccu gcagucuuga | 540 |
| aggcucuaca aguuuaugaa cgggguugcc gcugguaccc auagucgga ccugucccug | 600 |
| gaguggccga uuugccaac ucccuacaug ugagugauaa accuuucccg ggagcaacuc | 660 |
| augugcuaac caaccugcca cucccagaga ggccuaagcc ugaagacuuu ugcccuucug | 720 |
| agugugcuau ggcugacguc uaugauauug gccauggcgc cgucauguau guggccaaag | 780 |
| ggaaagucuc cugggccccu cguggcgggg augaggcgaa auuugaaccu gucccuaggg | 840 |
| aguugaaguu gaucgcgaac caacuccaca ucuccuuccc gccccaccac gcaguggaca | 900 |
| ugucuaaguu uguguucaua gccccuggga guguguccuc uaugcggguc gagugcccac | 960 |
| acggcugucu ccccgcuaau acugucccug aagguaacug cugguggcgc uuguuugacu | 1020 |
| cgcucccacu ggacguucag aacaaagaaa uucgccgugc caaccaauuc ggcuaucaaa | 1080 |
| ccaagcaugg ugucgcuggc aaguaccuac aacgaggcu gcaagcuaau ggucuccgag | 1140 |
| cagugacuga uacagaugga cccauugucg uacaguauuu cucuguuagg gagagcugga | 1200 |
| uccgccacuu cagacuggcg gaagagccua gccucccugg guuugaagac cucucagaa | 1260 |
| uaagggguaga gcccaauacg ucgccauuga ugacaagggu ggaaaaauc uuccgguuug | 1320 |
| gcagucacaa augguacggu gcuggaaaga gagcaaggaa agcacgcucu gguaugacca | 1380 |
| ccacagucgc ucaccgcgcc uugcccgcuc gugaaaucca gcaagccaaa agcacgagg | 1440 |
| augccggcgc ugauaaggcu gugcaucuca ggcacuauuc uccgcuugcc gacgggaacu | 1500 |
| gugguuggca cugcauuucc gccaucgcca accgaauggu gaauccaaa uugaaacua | 1560 |
| cucuucccga gagggugaga ccuucagaug acugggcuac ugacgaggac cuugugaaca | 1620 |
| ccauccaaau ucucaagcuc ccugcggccu uggacaggaa cggugcuugu uuggcgcca | 1680 |
| aauacgugcu uaagcuggaa ggcgagcauu ggacugucuc ugugacccuu gggaugcccc | 1740 |
| cuucuuugcu cccccuugaa uguguucagg cuguugauga cauaagagc ggacuugguc | 1800 |

-continued

```
ccccagaugc ggucgaaguu uucggauuug acccugccug ccuugaccga cuggcugagg     1860
uaaugcacuu gccuagcagu gucaucccag cugcucuggc cgaaaugucc ggcgacccca     1920
accguccggc uucccgguc acuacugugu ggacuguuuc acaauucuuu gcccgccaca      1980
gaggaggaga gcacccugau caggugcgcu aggaaaaau caucagccuu gucaaguug       2040 uugaggaaug cuguugccau cagaauaaaa ccaaccgggc caccccggaa gagguugcgg     2100
caaggauuga ucaguaccuc caugguguaa caagucuuga agaaugcuug auuaggcuug     2160
agagggnuuu cccgccgagc gcucgggaca ccuucuuuga uuggaauguu gugcucccug     2220 gguuggggc uucaacucag acaaccaaac agcuccaugu caaccagugc cgcgcucugg      2280
uuccugucgu gacucaagag ccuuggaca aagacccagu cccucugacc gccuucucgc      2340
uguccaauug cuacuauccu gcacaaggug acgagguucg ucaccgugag aggcuaaacu     2400
ccguacucuc uaagcuggag gggguuguuc gugaggaaua ugggcucacg ccaacuggac     2460
cuggcccgcg acccgcacua ccgaacgggc ucgucgaacu uaaagaccag auggaggagg     2520
aucugcuaaa acuagucaac gcccaggcaa cuucagaaau gauggccugg gcagccgagc     2580
agguugaucu gaaagcuugg gucaaaaacu acccacggug gacaccguca cccccuccac     2640
caagaguuca gccucgaaaa acaaagccug ucaagagcuu gccagggaac aaaccugucc     2700
ccgcuccacg caggaagguc agaucugauu guggcagccc gauuucgaug ggcgacaaug     2760
uuccugacgg ucgggaagau uugacuguug guggcccccu ugaucuuucg acaccauccg     2820
agccgaugac accucugagu gagccugcac cuaugcccgc guugcaauau auuucuaggc     2880
cagugacacc uuugagugug cuggcgccag uaccugcacc gcguagaacu gugucccgac     2940
cggugacgcc cuugagugag ccaauuuuug ugucugcacc gcgacacaaa uuucagcagg     3000
uggaagaagc gaaucuggcg gcaacaaugc ugacgcacca ggacgaaccu cuagauuugu     3060
cugcauccuc acagacugaa uaugaggcuu cucccuaac accacugcag aacaugggua     3120
uucuggaggu gggggggcaa gaagcugagg aaguucgag ugaaaacucg auacacuga      3180 augacaucaa cccugcaccu gucaucaa gcagcucccu gucaaguguu aagaucacac       3240
gcccaaaaca cucugcucaa gccaucauug acucgggcgg gcccugcagu gggcaucucc     3300
gaaagggaaa agaagcaugc cucagcauca ugcgugaggc uugugaugcg gcuaagcuua     3360
gugacccugc cacgcaggaa uggcuuucuc gcauguggga uagggnugau augcugacuu     3420
ggcgcaacac gucugcuuac caggcguucc gcaucuuaga ugguagguuu gaguuucucc     3480
caaagaugau acucgagaca ccgccgcccu acccgugugg guuugugaug cugccucgca     3540
cgccugcacc uucggggu gcagagagug accuaccau ugguucaguc gccacugaag       3600 auguccacg caucccgggg aaaauagaaa acgccggcaa gaugcccaac caggggcucu      3660
ugacauccuu cggggaagaa ccggugugcg accaaccugu caaggacucc uggaugucgu     3720 cgcgggguu ugacgagagc caacggcuc cguccgcugg uacaggauggu gcugacuuac      3780 ccaccgauuu gccaccuuca gauguuuugg augcggacga gugggggccg uucggacgg     3840 uaagaaagaa agcugaaagg cucuucgacc aauugagccg ucagguuuuu aaccucgucu     3900
cccaucuccc uguuucuuc ucacaccucu ucaaaucuga caguguau ucuccggug        3960 auugggguuu ugcagcuuuu acuuuauuuu gccucuuuuu guguuacagc uacccauucu     4020 uugguuugu uccccucuug ggguuuuuu cugggucuuc ucggcgugug cgcauggggg       4080 uuuuggcug uuggouuggcu uuugcuguug gccuguucaa gccugugucc gacccagucg     4140
gcacugcuug ugaguuugac ucgccagagu guaggaacgu ccuucauucu uuugagcuuc     4200
```

-continued

```
ucaaaccuug ggacccuguu cgcagccuug uugugggccc cgucggcucu ggccuugcca    4260
uucuuggcag guuacugggc ggggcacgcu acaucuggca uuuuugcuu aggcuuggca    4320 uuguugcaga uuguaucuug gcuggagcuu augugcuuuc ucaagguagg guaaaaagu    4380 gcuggggauc uuguguaaga acugcuccua augaaaucgc cuucaacgug ucccuuuua    4440 cgcgugcgac caggucguca cucaucgacc ugugcgaucg guuuugugcg ccaaaaggca    4500
uggaccccau uuuccucgcu acuggguggc gcgggugcug gaacggccga aguccccauug   4560 agcaaccccuc ugaaaaaccc aucgcguucg cccaguugga ugaaagagg aucacggcua    4620 gaacugguggu cgcucagccu uaugauccua accaagccgu aaagugcuug cgggguguuac   4680 aggcgggugg ggcgauagug gccgaggcag ucccaaaagu ggucaagguu ccgcuauuc    4740 cauuccgagc ucccuuuuuu cccaccggag ugaagguuga uccugagugc aggaucgugg    4800
ucgaccccga cacuuuuacu acagcucucc ggucugguua uccaccaca aaccucgucc    4860 uugguguagg ggacuuugcc caacugaaug gauuaaaaau caggcaaaauu uccaagcccu    4920 cgggaggagg cccgcaccuc auugcugccc ugcauguugc uugcucgaug gcguugcaca    4980
ugcuugcugg aguuuaugua acugcagugg ggucuugcgg uaccggcacc aacgauccgu    5040
ggugcacuaa cccauucgcc gucccuggcu acggaccugg ucccucugc acguccagau    5100 ugugcaucuc ccaacauggc cuuacccugc ccuugacagc acuguggca ggauucgguc     5160 uucaggaaau ugcccuaguc guuugauuu ucguuccau cggaggcaug gcucauaggu      5220
ugaguuguaa ggcugauaug cugucgcucu acuugcaau cgccagcuau guuugggguac   5280 cccuuaccug guugcucugu guguuuccuu gcugguugcg cugguucucu uugcacccuc    5340
ucaccauucu augguuggug uuuuucuuga ugucuguaaa uaugccuucg ggaaucuuaa    5400
ccgugguguu auugguugcu cuuuggcuuc uaggccguua acuaauguu guuggucuug     5460 uuaccccccua ugauauucac cauuacacca auggccccccg cggguguuugcc gccuuggcua   5520 ccgcaccaga uggggacuuac uuggccgcug uccgccgcgc ugcguugacu ggccgcaccg    5580
ugcuguuuac cccgcucucag cuuggguccc uucuugaggg cgcuuucaga acucgaaagc    5640
ccucacugaa caccgucaau gggucgggu ccuccauggg cucuggcgga guguucacua     5700
ucgaugggaa aauuaagugc gugacugccg cacauguccu uacggguaau ucagccaggg    5760
uuuccggggu cggcuuuaau caaaugcuug acuugaugu aaaaggggac uucgccauag     5820
cugacugccc gaauuggcaa ggggcugcuc cuaagaccca auucgcgag gauggaugga    5880 cuggccgcgc cuauuggcug acauccucug gcgucgaacc cggugucauu gggaauggau    5940
ucgccuucug cuucaccgcg ugcggcgauu ccgguccccc agugaucacc gaagccggug    6000
agcuugucgg cguucacaca ggaucaaaca aacaaggagg aggcauuguu acgcgccccu    6060
cuggccaguu uugcaaugug gcacccauca agcugagcga auuaagugag uucuuugcug    6120
gaccuaaggu cccgcucggu gaugugaagg uuggcagcca cauaauuaaa gacauaugcg    6180
agguaccuuc agaucuuugc gccuugcuug cugccaaaac cgaacuggaa ggaggccucu    6240
ccaccgucca acuucugugu guguuuuccc uccugugag aaugauggga caugccugga    6300
cgcccuuggu ugcuguuggg uuuuuuaucu ugaaugaggu ucucccagcu guacuggucc    6360
ggaguguuuu cuccuuugga auguuugugc uaucuuugcu cacaccaugg ucugcgcaag    6420
uucugaugau caggcuucua acagcagcuc uuaacaggaa cagauugucu cucgcccuuu    6480
acagccuugu ugcagcgacc gguuugugcg cagaucuggc ggcaacucaa gggcacccgu    6540
ugcaggcagu aaugaauuua aguaccuaug ccuuccugcc ucggauaaug gucgugaccu    6600
```

-continued

```
caccaguccc agugauugcg uguggguguug ugccauccu ugccauaauu uuguacuugu    6660
uuaaguaccg cugccugcac aaugccuug uuggcgaugg ugcguucucu gcggcuuucu    6720
ucuugcgaua cuuugccgag gggaaauuga gggaaggggu gucgcaaucc ugcgggauga    6780
aucaugaguc gcugacuggu gcccucgcua ugagacuuaa ugacgaggac uuggauuuuc    6840
uuacgaaaug gacugauuuu aaguguuuug uuucugcauc caacaugagg aaugcggcgg    6900
gccaguucau cgaggcugcc uaugcuaaag cacuuagaau ugaacuugcc caguggugc    6960 agguugauaa gguucgaggu acuuggcca aacuugaagc uuuugcugau accguggcac    7020
cccaacucuc gcccggugac auuguuguug cucuuggcca uacgccuguu ggcgguaucu    7080
ucgaccuaaa gguugguagc accaagcaua cccuccaagc cauugagacc agaguucuug    7140
ccggguccaa aaugaccgug gcgcguguc uugauccaac cccacaccc ccacccgcac     7200 ccgugccuau ccccuucca ccgaaaguuc uggagaaugg ucccaacgcc ugggggggaug   7260 aggaucguuu gaauaagaag aagaggcgca agauggaagc cgucggcauc uuuguuaugg    7320
guggaaagaa auaucagaaa uuugggaca agaacccgg ugaguguuuu uaugaggagg     7380
uccaugauaa cacagacgcg ugggagugcc ucagaguuga caacccugcc gacuuugacc    7440
cugagaaggg aacucugugc gggcauacua ccaugaaga uaagacuuac agugucuacg    7500 ccucccauc uggcaagaaa uuccuggucc cgccuaccc agagagcaaa aaaaaccaau     7560
gggaagcugc gaagcuuucc guggaacagg cccuuggcau gaugaaugc gacggugaac     7620 ugacagccaa agaaguggag aaacugaaaa gaauaauuga caaacuccag ggccugacua    7680
aggagcagug uuuaaacugc uagccgccag cggcuugacc cgcuguggu gcggcggcuu     7740 gguuauuacu gagacagcgg uaaaaauagu caaauuucac aaccggaccu ucacccuagg    7800
accugugaau uuaaaagugg ccagugaggu ugagcuaaaa gacgcggucg agcauaacca    7860
acacccgguu gcaagaccgg uugauggugg uguugcucuc cugcgcuccg caguccuuc     7920 gcuauagac gucuuaaucu ccggcgcuga ugcaucccc aaguuacucg cccgccacgg     7980
gccgggaaac acugggaucg auggcacgcu uugggauuu gaggcgagg ccacuaaaga     8040 ggaaauugca cucagugcgc aaauaauaca ggcuugugac auuaggcgcg gcgacgcacc    8100
ugaaauuggu cuuccuuaua agcuguaccc ugucaggggc aacccugagc ggguaaaagg    8160
aguuuuacag aauacaaggu uuggagauau accuauaaa accccccagug acacuggaag    8220 cccagugcac gcggcugccu gccucacgcc caaugccacu ccggugacug auggcgcuc     8280 cgucuuggcc acgacuaugc ccuccgguuu ugaguuguau guaccgacca uuccagcguc    8340 ugccuugau uaucuugauu cuaggccuga cugccccaaa caguugacag agcacggcug    8400
ugaggacgcc gcauuaagag accucuccaa guaugacuug uccacccaag gcuuuguuuu    8460
accuggaguu cuucgccuug ugcguaagua ccuguuugcu caugggguu agugcccgcc    8520 cguucaucgg ccuuccacuu acccugccaa gaauucuaug gcuggaauaa augggaacag    8580
guuuccaacc aaggcauucc agagcguccc ugaaaucgac guucugucg cacaggccgu    8640 ucgggaaaac uggcaaacug uuaccccuug uaccucaag aaacaguauu gugggaagaa    8700
gaagacuagg acaauacucg gcaccaauaa cuucauugcg cuggcucacc gggcagcguu    8760
gagugguguc acccagggcu ucaugaaaaa ggcguuuaac ucgccauug cccucgguaa    8820 aaacaaauuu aaagagcuuc agacuccggu cuuaggcagg ugccuugaag cugaucuugc    8880
auccugcgau cgcuccacac cugcaaugu ccgcugguu gccgcaauc uucuuugauga    8940 acuugccugu gcugaagagc accagccguc guacguguug aacugcugcc acgaccuacu    9000
```

-continued

```
ggucacgcag uccggcgcag uaacuaagag agguggccug ucgucuggcg acccgaucac    9060 uucuguqucc aacaccauuu acagcuuggu gauauaugca caacacaugg ugcucaguua    9120
cuuuaaaagu ggucacccuc auggccuucu guuucuacaa gaccagcuga aguuugagga    9180
caugcucaag guucaacccc ugaucgucua uucggacgac cucguacugu augccgaguc    9240
ucccaccaug ccaaacuacc acuggugggu ugaacaucug aaccugaugc uggguuuuca    9300
gacggaccca aagaagacag ccauaacaga cucgccauca uuucuaggcu guaggauaau    9360
aaauggacgc cagcucgucc cuaaccguga caggauucuc gcggcccucg ccuaccauau    9420
gaaggcaagc aaugucucug aauacuacgc cucggcggcu gcgauacuca uggacagcug    9480
ugcuuguuua gaguaugauc ccgaaugguu ugaagagcuu guaguuggga uagcgcagug    9540
ugcccgcaag gacggcuaca guuucccgg cccgccguuc uucuugucca guggaaaaa     9600 acucagaucc aaucaugagg ggaagaaguc cagaaugugc ggguacgcg gggccccggc     9660 uccguacgcc acugccugug gccucgacgu cuguauuuac cacacccacu uccaccagca    9720
uuguccaguc aucaucuggu guggccaccc ggcugguucu gguucuugua gugagugcaa    9780
acccccccua gggaaaggca aagcccucu agaugaggug uuagaacaag ucccguauaa     9840
gccuccacgg acuguaauca ugcaugugga gcagggcucu accccucuug acccaggcag    9900
auaccagacu cgccgcggau uagucuccgu uaggcguggc auuagaggaa augagguuga    9960
ucuaccagac ggugauuaug cuagcaccgc cuacucccu acuguaaag agauuaacau      10020 ggucgcuguc gccucuaaug uguugcgcag cagguucauc aucggcccgc cuggugcugg    10080
gaaaacauac uggcuccuuc aacaggucca ggaugugau gccauuuaca cgccaacuca     10140
ccagaccaug cucgauauga uuagggcuuu ggggacgugc cgguucaacg ucccagcagg    10200
uacgacgcug caauucccug cccccucccg uaccggcccu uggguucgca uccuagccgg    10260 cgguugggu ccuggcaaga auuccuuccu ggaugaagca gcguauugua ucaccuuga      10320 ugucuugagg cuucuuagca aaacuacccu caccugucug ggagauuuca acaacucca    10380 cccagugggu uuugauucuc auugcuaugu uuuugacauc augccucaga cucaacugaa    10440
gaccaucugg agauuuggac agaauaucug ugaggccauu cagccagauu acagggacaa    10500
acuuguaucc auggucaaca caacccgugu aaccacgugg gaaaaaccug ucaaguaugg    10560
gcaaguccuc accccuuacc acagggaccg agaggacggc gccaucacaa uugacuccag    10620
ucaaggcgcc acauuugaug ugguuacacu gcauuugccc acuaaagauu cacucaacag    10680
gcaaagagcc cuuguugcua uuaccagggc aagacaugcu gucuugugu augacccaca     10740 caggcaacug cagagcaugu uugaucuuuc ugcgaaaggc acaccgucac ccucgcugu     10800 gcaccgugac gagcagcuga ucgugcuaga uaagaauaac aaagaaugca cgguugcuca    10860
ggcucuaggc aauggggaua aauucagggc cacagacaag cgcguuguag auucucuccg    10920
cgccauuugu gcagaucugg aagggucgag cuccccgcuc cccaaggucg cacacaacuu    10980
gggauuuuau uucucgccug auuugacaca guuugcuaaa cucccggaug aacuugcacc    11040
ccacuggccc gugugacaa cccagaacaa ugaaaagugg ccagaccggu gguugcuag      11100 ccuucgcccc guccauaagu auagccgcgc gugcaucggu gccggcuaca ugugggccc    11160 cucaguguuu cugggcaccc cugggguugu gucauacuau cucacaaaau uguccagggg   11220
cgaggcucaa augcuuccgg agacagucuu cagcaccggc gaauugagg uagauugccg    11280 ugaguaucuc gaugaccggg agcgagaaau ugcugagucc cuccccaug cuuucauugg    11340 cgacgucaaa ggcacuaccg uuggaggaug ucaccauguc accuccaaau accuuccgcg    11400
```

-continued

```
cuuccuuccc aaggaaucag ucgcgguagu cggggguuuca agccccggga aagccgcaaa    11460
agcaguuugc acauuaacag auguguaucu cccagaucuc gaagcuuacc uccacccaga    11520
gacccagucc aagugcugga aaaugauguu ggacuucaag gaaguucgac ugauggucug    11580
gaaggacaag acggccuauu ucaacuuga aggccgccau uucaccuggu accagcuugc    11640
aagcuaugcc ucguacaucc gaguccugu uaacucuacg guguauuugg accccugcau    11700
gggcccugcc cuuugcaaca gaagaguugu cggguccacu cauuggggag cugaccucgc    11760 agucacccu uaugauuacg gugccaaaau cauccugucu agugcauacc augugaaau    11820 gcccccuggg uacaaaaucc uggcgugcgc ggaguucucg cuugacgauc cagugaggua    11880
caaacacacc uggggguuug aaucggauac agcguaucug uacgaguuca ccggaaacgg    11940
ugaggacugg gaggauuaca augaugcguu ucgugcgcgc cagaaaggga aaauuuauaa    12000
ggccacugcc accagcauga gguuucauuu uccccggc ccugucauug aaccaacuuu    12060
aggccugaau ugaaaugaaa uggggguccau gcaaagccuc uuugacaaaa uuggccaacu    12120 uuucgugga u gcuuucacgg aauuuuuggu guccauuguu gauaucauca uauuuuuggc    12180
cauuuuguuu ggcuuuacca ucgcuggcug gcugguggu c uucugcaucc gauugguuu    12240 cccgcgguua cucgcugcgc gcccuaccau ucacccugag caauuacaga agauccuaug    12300
aggccuuucu uucucaguge caggggaua uccccaccug ggaacuaga cauccccugg    12360 ggaugcuuug gcaccauaag ggucaaccc ugauugauga aaugugucg cgucggaugu    12420 accgcaccau ggaaaaaagca ggacaggcug ccuggaaaca ggguggagc gaggccacgc    12480 ugucucgcau uaguggguuug gauggugugg cucauuuuca gcaucuugcc gccauugaag    12540
ccgagaccug uaaauauuug gccucucggc ugcccaugcu acacaaucug cgcaugacag    12600
ggucaaaugu aaccauagug uauaauagua cuuugaauca gguguuugcu auuuuuccaa    12660
ccccuggauc ccggccaaag cuucaugauu ucagcaaug gcuaauagcu gugcacuccu    12720
ccauauuuuc ucccguugcg gcuucuugua cucuuuugu ugugcugug g uugcggauuc    12780 caaugcuacg uacuguuuuu gguuuccgcu gguuaggggc aauuuuuccu ucgaacucac    12840
ggugaauuac acgugugguc cgccuugccu cacccggcaa gcagccgcug aggucuacga    12900
accaggcagg ucucuuuggu gcaggauagg gcaugaccga uguagugagg aagaccauga    12960
cgaucuaggg uucaugguuc cgucuggccu cuccagcgaa ggccacuuga ccaguguuua    13020
cgccugguug gcguuccugu ccuucagcua acggcccag uuccauccg agauauuug g    13080 gauagggaau gugagucaag uuuauguuga caucaagcac caauucaucu gcgccguuca    13140
cgacggggag aacgccaccu ugccucguca ugacaauauu ucagccguau aucagaccua    13200
cuaccaacau caagucgacg gcggcaauug guuucaccua gaauggcugc gccccuucuu    13260
uuccucuugg uugguuuaa auguuucuug guuucagg cguucgccug caagccaugu    13320
uucaguucaa gucuuucgga caucaaaacc aacacaaccg cagcaucagg cuuguugguc    13380
cuccaggaca ucagcugccu uaggcauggc gacucguccu ucagacgau ucgcaaaagc    13440 ucucagugcc gcgcggcgau agggacgccc guguacauca cugucacagc caaugucaca    13500
gaugagaauu auuacauuc uucugaucuc cuuaugcuuu cuucuugccu uucuaugcu    13560 ucugagauga gugaaaaggg auucaaggug auguuuggca augu caggg caucuggcu    13620 guguguguca acuuuaccag cuacguccaa caugucaagg aguuuaccca acgcuccuug    13680
guggucgauc augugcggcu gcuccauuuc augacaccug agaccaugag gugggcaacc    13740
guuuuagccu guuuucuugc caucuuacug gcaauuugaa uguucaagua uguuggggag    13800
```

-continued

| | |
|---|---|
| augcuugacc gcgggcuguu gcucgcgauu gcuuucuuug ugguguaucg ugccauuuug | 13860 |
| uuuugcugcg cucgucaacg ccaacagcaa cagcagcucu caucuucagu uaauuuacaa | 13920 |
| cuugacgcua ugugagcuga auggcacaga uuggcugaaa gacaaauuug auugggcauu | 13980 |
| ggagacuuuu gucaucuuuc ccguguugac ucacauuguc ucauauagug cacucaccac | 14040 |
| uagccauuuc cuugacacag ucggucuggu uacugugucu acugccgggu ucuaccacgg | 14100 |
| gcgguauguu cugaguagca ucuacgcggu cugcgcucug gccgcauuga cuugcuucgu | 14160 |
| cauuaggcuu gcgaagaacu gcaugccug gcgcuacucu uguaccagau auacuaacuu | 14220 |
| ccuucuggac acuaagggca gacucuaucg cuggcggucg cccguuauca uagagaaagg | 14280 |
| ggguaagguu gaggucgaag gucaccugau cgaccucaaa agaguugugc uugauggeuc | 14340 |
| cguggcaacc ccuuuaacca gaguuucagc ggaacaaugg ggucgucuuu agacgacuuu | 14400 |
| ugcuaugaua gcacggcucc acaaaaggug cuuuuggcgu uuccauuac cuacacgcca | 14460 |
| gugaugauau augcucuaaa gguaagucgc ggccgacuuu uagggcuucu gcaccuuuug | 14520 |
| aucuuucuga auuguacuuu uaccuucggg uacaugacau gcgugcacuu aauagcaca | 14580 |
| aauaaggucg cgcucacuau gggagcagua guugcacuuc uuuggggggu guacucagcc | 14640 |
| auagaaaccu ggaaguucau caccuccaga ugucguuugu gcuugcuagg ccgcaaguac | 14700 |
| auucuggccc ccgcccacca cgucgaaagu gccgcgggcu uucauccgau cgcggcaaau | 14760 |
| gauaaccacg cauuugucgu ccggcgcucc ggcuccacua cgguuaacgg cacauuggug | 14820 |
| cccggguuga aagccucgu guugggguggc agaaaagcuu uuaaacaggg aguggguaaac | 14880 |
| cuugucaaau augccaaaua caacggcaa gcagcaaaag aaaagagggg gaauggcca | 14940 |
| gccagucaau cagcugugcc agaugcuggg uaagaucauc gcccagcaaa accagucag | 15000 |
| aggcaaggga ccggggaaga aaauuaagaa uaaaacccg gagaagcccc auuuccucu | 15060 |
| agcgacugaa gaugacguca ggcaucacuu caccccuagu gagcggcaau uguguvcuguc | 15120 |
| gucgauccag acugccuuua accagggcgc uggaaccugu acccuaucag auucagguag | 15180 |
| gauaaguuac acguggagu uuaguuugcc gacgcaucau acgugcgcc ugauccgcgu | 15240 |
| cacagcgcca ucaucagcgu aaugggcugg cauuccuuaa gcaccucagu guuagaauug | 15300 |
| gaagaaugug uggugaaugg cacugauugg cacugugccu cuaagucacc uauucaauua | 15360 |
| gggcgaccgu gugggguua aguuuaauug gcgagaacca ugcggccgaa auu | 15413 |

<210> SEQ ID NO 4
<211> LENGTH: 15413
<212> TYPE: RNA
<213> ORGANISM: Porcine reproductive and respiratory syndrome virus

<400> SEQUENCE: 4

| | |
|---|---|
| augacguaua gguguuggcu cuaugccuug gcauuuguau ugucaggagc ugcgaccauu | 60 |
| gguacagccc aaaacuagcu gcacagaaaa cgcccuucug ugacagcccu cuucagggga | 120 |
| gcuuagggu cugucccuag caccuugcuu ccggaguugc acugcuuuac ggucucucca | 180 |
| acccuuuaac caugucuggg auacuugauc ggugcacgug caccccaau gccagggugu | 240 |
| uuauggcgga gggccaaguc uacugcacac gaugucucag ugcacggucu cuccuuccuc | 300 |
| ugaaucucca aguccugag cuggagugc ugggccuauu uucaggccc gaagagccac | 360 |
| uccgguggac guugccacgu gcauccccca cuguugagug ucccccgcc ggggccugcu | 420 |
| ggcuuucugc gaucuuucca auugcacgaa ugaccagugg aaaccugaac uuucaacaaa | 480 |
| gaauggugcg ggucgcagcu gagauuuaca gagccggcca gcucaccccu gcagucuuga | 540 |

-continued aggcucuaca aguuuaugaa cggggguugcc gcugguaccc uauagucgga ccugucccug 600
gaguggccgu uuuugccaac ucccuacaug ugagugauaa accuuucccg ggagcaacuc 660
augugcuaac caaccugcca cucccgcaga ggccuaagcc ugaagacuuu ugcccuuuug 720
agugugcuau ggcugacguc uaugauauug gucauggcgc cgucauguau guggccaaag 780
ggaaagucuc cugggccccu cguggcgggg augaggcgaa auuugaaacu gucccuaggg 840
aguugaaguu gaucgcgaac caacuccaca ucuccuuccc gccccaccac gcaguggaca 900
ugucuaaguu uguguucaua gccccuggga guggugucuc uaugcggguc gagugcccac 960
acggcugucu ccccgcuaau acugucccug aagguaacug cugguggcgc uuguuugacu 1020
cgcucccacu ggacguucag aacaaagaaa uucgccgugc caaccaauuc ggcuaucaaa 1080
ccaagcaugg ugucgcuggc aaguaccuac aacggaggcu gcaagcuaau ggucuccgag 1140
cagugacuga uacagaugga cccauugucg uacaguauuu cucuguuagg gagagcugga 1200
uccgccacuu cagacuggcg gaagagccua gccucccugg guuugaagac cuccucagaa 1260
uaaggguaga gcccaauacg ucgccauuga gugacaaggg uggaaaaauc uuccgguuug 1320
gcagucacaa augguacggu gcuggaaaga gagcaaggaa agcacgcucu gguaugacca 1380
ccacagucgc ucaccgcgcc uugcccgcuc gugaaaucca gcaagccaaa aagcacgagg 1440
augccggcgc ugauaaggcu gugcaucuca ggcacuauuc uccgccugcc gacgggaacu 1500
gugguuggca cugcauuucc gccaucgcca accgaauggu gaauuccaaa uuugaaacua 1560
cucuucccga gagggugaga ccuucagaug acugggcuac ugacgaggac cuugugaaca 1620
ccauccaaau ucucaagcuc ccugcggccu uggacaggaa cggugcuugu guuggcgcca 1680
aauacgugcu uaagcuggaa ggcgagcauu ggacugucuc ugugacccuu gggauguccc 1740
cuucuuugcu cccccuugaa uguguucagg gcuguuguga gcauaagagc ggacuugguc 1800
ccccagaugc ggucgaaguu uucggauuug acccugccug ccuugaccga cuggcugagg 1860
uaaugcacuu gccuagcagu gucaucccag cugcucuggc cgaaaugucc ggcgacccca 1920
acuguccggc uuccccgguc acuacugugu ggacuguuuc acaauucuuu gcccgccaca 1980
gaggaggaga gcacccugau caggugcgcu uaggaaaaau caucagccuu ugucaaguug 2040
uugaggaaug cuguugccau cagaauaaaa ccaaccgggc caccccggaa gagguugcgg 2100
caaggauuga ucaguaccuc cauggugcaa caagucuuga agaaugcuug auuaggcuug 2160
agaggguuug cccgccgagc gcugcggaca ccuucuuuga uuggaauguu gugcucccug 2220
ggguuggggc uucaacucag acaaccaaac agcuccaugu caaccagugc cgcgcucugg 2280
uuccugucgu gacucaagag ccuuuggaca aagacucagu cccucugacc gccuucucgc 2340
uguccaauug cuacuauccu gcacaaggug acgagguucg ucaccgugag aggcuaaacu 2400
ccguacucuc uaagcuggag gggguuguuc gugaggaaua ugggcucacg ccaacugaac 2460
cuggcccgcg acccgcacua ccgaacgggc ucgucgaacu uaaagaccag auggaggagg 2520
aucugcugaa acuagucaac gcccaggcaa cuucagaaau gauggccugg gcagccgagc 2580
agguugaucu gaaagcuugg gucaaaaacu acccacggug gacaccgcca cccccuccac 2640
caagaguuca gccucgaaaa acaaagucug ucaagagcuu gccagggaac aaaccugucc 2700
ccgcuccacg caggaagguc agaucugauu guggcagccc gauuuugaug ggcgacaaug 2760
uuccugacgg ucgggaagau uugacuguug guggcccccu ugaucuuucg acaccauccg 2820
agccgaugac accucugagu gagccugcac uuaugcccgc guugcaauau auuucuaggc 2880
cagugacauc uuugagugug cuggccccag uuccugcacc gcguagaacu guguccccgac 2940

-continued

| | | | | |
|---|---|---|---|---|
| cggugacgcc | cuugagugag | ccaauuuuug | ugucugcacc | gcgacacaaa | uuucagcagg | 3000 |
| uggaagaagc | gaaucuggcg | gcaacaacgc | ugacgcacca | ggacgaaccu | cuagauuugu | 3060 |
| cugcauccuc | acagacugaa | uaugaggcuu | cuccccuaac | accacugcag | aacaugggua | 3120 |
| uucuggaggu | gggggggcaa | gaagcugagg | aaguucugag | ugaaaucucg | gauacacuga | 3180 |
| augacaucaa | cccugcaccu | gugucaucaa | gcagcucccu | gucaagguu | aagaucacac | 3240 |
| gcccaaaaca | cucugcucaa | gccaucauug | acucgggcgg | gcccugcagu | gggcaucucc | 3300 |
| gaagggaaaa | agaagcaugc | cucagcauca | ugcgugaggc | uugugaugcg | gcuaagcuua | 3360 |
| gugacccugc | cacgcaggaa | uggcuuucuc | gcaugggga | uaggguugac | augcugacuu | 3420 |
| ggcgcaacac | gucugcuuac | caggcguucc | gcaucuuaga | ugguagguuu | gaguuucucc | 3480 |
| caaagaugau | acucgagaca | ccgccgcccu | acccgugugg | guuugugaug | cugccucaca | 3540 |
| cgccugcacc | uuccgugggu | gcagagagug | accuuaccau | ugguucaguc | gccacugaag | 3600 |
| auguccacg | cauccucggg | aaaauagaaa | acgccggcga | gaugcccaac | caggggcucu | 3660 |
| ugacauccuu | cggggaagaa | ccggugugcg | accaaccugu | caaggacucc | uggaugucgu | 3720 |
| cgcggggguu | ugacgagagc | acaacggcuc | cguccgcugg | uacaggugu | gcugacuuac | 3780 |
| ccaccgauuu | gccaccuuca | gaugguuugg | augcggacga | gugggggccg | uuacggacgg | 3840 |
| uaagaaagaa | agcugaaagg | cucuucgacc | aauuagccg | ucagguuuuu | aaccucgucu | 3900 |
| cccaucuccc | uguuuucuuc | ucacaccucu | ucaaaucuga | cagugguuau | ucuccggug | 3960 |
| auuggguuu | ugcagcuuuu | acuuauuuu | gccucuuuu | guguuacagc | uacccauucu | 4020 |
| uugguuugu | ucccucuug | ggguguuuuu | cugggucuuc | ucggcgugug | cgcauggggg | 4080 |
| uuuuggcug | uugguuggcu | uuugcuguug | gccuguucaa | gccugugucc | gacccagucg | 4140 |
| gcacugcuug | ugaguuugac | ucgccagagu | guaggaacgu | ccuucauucu | uuugagcuuc | 4200 |
| ucaaaccuug | ggaccuguu | cgcagccuug | uguggggccc | cgucggucuc | ggccuugcca | 4260 |
| uucuuggcag | guuacugggc | ggggcacgcu | acaucggca | uuuuugcuu | aggcuuggca | 4320 |
| uuguugcaga | uuguaucuug | gcuggagcuu | augugcuuuc | ucaaggugg | uguaaaagu | 4380 |
| gcuggggauc | uuguguaaga | acugcuccua | augaaaucgc | cuucaacgug | ucccuuuua | 4440 |
| cgcgugcgac | caggucguca | cucaucgacc | ugugcgaucg | guuuugugcg | ccaaaaggca | 4500 |
| uggaccccau | uuccucgcu | acugggugg | gcgggugcug | gaccggccga | aguccauug | 4560 |
| agcaaccuc | ugaaaacccc | aucgcguucg | cccaguugga | ugaaaagagg | auuacggcua | 4620 |
| gaacuguggg | cgcucagccu | uaugauccua | accaagccgu | aaagugcuug | cggguguuac | 4680 |
| aggcgggugg | ggcgauagug | gccgaggcag | ucccaaaagu | ggucaagguu | ccgcuauuc | 4740 |
| cauuccgagc | ucccuuuuuu | cccaccggag | ugaagguuga | uccugagugc | aggaucgugg | 4800 |
| ucgaccccga | cacuuuuacu | acagcucucc | ggucugguua | uccaccaca | aaccucgucc | 4860 |
| uuggugugg | ggacuuugcc | caacugaaug | gauuaaaaau | caggcaaauu | uccaagcccu | 4920 |
| cgggaggagg | cccgcaccuc | auugcugccc | ugcauguuc | uugcucgaug | gcguugcaca | 4980 |
| ugcuugcugg | aguuuaugua | acugcaguggg | ggucuugcg | uaccggcacc | aacgauccgu | 5040 |
| ggugcacuaa | cccauucgcc | gucccuggcu | acggaccugg | cucccucugc | acguccagau | 5100 |
| ugugcaucuc | ccaacauggc | cuuacccgc | ccuugacagc | acuuggca | ggauucgguc | 5160 |
| uucaggaaau | ugcccuaguc | guuuugauuu | ucguuuccau | cggaggcaug | gcucauaggu | 5220 |
| ugaguuguaa | ggcugauaug | cugucgcucu | acuugcaau | cgccagcuau | guugggguac | 5280 |
| cccuuaccug | guugcucugu | guguuccuu | gcugguugcg | cugguucucu | uugcacccuc | 5340 |

-continued

| | | | | |
|---|---|---|---|---|
| ucaccauucu | augguuggug | uuuuucuuga | ugucuguaaa | uaugccuucg ggaaucuuaa | 5400 |
| ccguggueuu | auugguugcu | cuuuggcuuc | uaggccguua | uacuaauguu guuggucuug | 5460 |
| uuaccccua | ugauauucau | cauuacacca | auggccccg | cgguguugcc gccuuggcua | 5520 |
| ccgcaccaga | ugggacuuac | uuggccgcug | uccgccgcgc | ugcguugacu ggccgcaccg | 5580 |
| ugcuguuuac | cccgcucag | cuugggucc | ucuugaggg | cgcuuucaga acucgaaagc | 5640 |
| ccucacugaa | caccgucaau | guggucgggu | ccuccauggg | cucuggcgga guuucacua | 5700 |
| ucgaugggaa | aauuaagugc | gugacugccg | cacauguccu | uacggguaau ucagccaggg | 5760 |
| uuuccggggu | cggcuucaau | caaaugcuug | acuugaugu | aaaggggac uucgccauag | 5820 |
| cugauugccc | gaauuggcaa | ggggcugcuc | cuaagaccca | auucugcgag gauggaugga | 5880 |
| cuggccgcgc | cuauuggcug | acauccucug | gcgucgaacc | cggugucauu gggaauggau | 5940 |
| ucgccuucug | cuucaccgcg | ugcggcgauu | ccggucccc | agugaucacc gaagccggug | 6000 |
| agcuugucgg | cguucacaca | ggaucaaaca | aacaaggagg | aggcauuguu acgcgcccu | 6060 |
| cuggccaguu | uugcaaugug | gcacccauca | agcugagcga | auuaagugag uucuuugcug | 6120 |
| gaccuaaggu | cccgcucggu | gaugugaagg | uuggcagcca | cauaauuaaa gacauaugcg | 6180 |
| agguaccuuc | agaucuuugc | gccuugcuug | cugccaaacc | cgaacuggaa ggaggccucu | 6240 |
| ccaccguccca | acuucugugu | uguuuuucc | uccuguggag | aaugauggga caugccugga | 6300 |
| cgcccuugu | ugcuguuggg | uuuuuaucu | ugaaugaggu | cucccagcu guacuggucc | 6360 |
| ggaguguuuu | cuccuuugga | auguuugcgc | uaucuuggcu | cacaccaugg ucugcgcaag | 6420 |
| uucugaugau | caggcuucua | acagcagcuc | uuaacaggaa | cagauuguca cucgccuuuu | 6480 |
| acagccuug | ugcagcgacc | gguuuugucg | cagaucuggc | ggcaacucaa gggcacccgu | 6540 |
| ugcaggcagu | aaugaauuua | aguaccuaug | ccuuccugcc | ucggauaaug gucgugaccu | 6600 |
| caccagucccc | agugauugcg | uggugugug | ugcaccuccu | ugccauaauu uguacuugu | 6660 |
| uuaaguaccg | cugccugcac | aauguccuug | uuggcgaugg | ugcguucucu gcggcuuucu | 6720 |
| ucuugcgaua | cuuugccgag | gggaaauuga | gggaagggu | gucgcaauccc ugcgggauga | 6780 |
| aucaugaguc | gcugacuggu | gcccucgcua | ugagacuuaa | ugacgaggac uuggauuuuc | 6840 |
| uuacgaaaug | gacugauuuu | aaguguuuug | uuucugcauc | caacaugagg aaugcggcgg | 6900 |
| gccaguucau | cgaggcugcc | uaugcuaaag | cacuuagaau | ugaacuugcc caguuggugc | 6960 |
| agguugauaa | gguucgaggu | acuuuggcca | aacuugaagc | uuuugcugau accguggcac | 7020 |
| cccaacucuc | gcccggugac | auuguuguug | cucuuggcca | uacgccuguu ggcgguaucu | 7080 |
| ucgaccuaaa | gguuguagc | accaagcaua | cccuccaagc | cauugagacc agauucuug | 7140 |
| ccgggucaa | aaugaccgug | gcgcgugucg | uugauccaac | cccacacccc ccaccgcac | 7200 |
| ccgugccuau | ccccuucca | ccgaaaguuc | uggagaaugg | ucccaacgcc uggggggaug | 7260 |
| aggaucguuu | gaauaagaag | aagaggcgca | ggauggaagc | cgucggcauc uuuguuaugg | 7320 |
| guggaaagaa | auaucagaaa | uuuugggaca | agaacuccgg | ugauguguuu uaugaggagg | 7380 |
| uccaugauaa | cacagacgcg | uggagugcc | ucagaguuga | caaaccugcc gacuuugacc | 7440 |
| cugagaaggg | aacucugugc | gggcauacua | ccaugaagaa | uaagacuuac aguguacg | 7500 |
| ccucccauc | uggcaagaaa | uuccggucc | cgucuaccc | agagagcaaa aaaaaccaau | 7560 |
| gggaagcugc | gaagcuuucc | guggaacagg | cccuuggcau | gaugaaugec gacggugaac | 7620 |
| ugacagccaa | agaaguggag | aaacugaaaa | gaauaauuga | caaauccag ggccugacua | 7680 |
| aggagcagug | uuuaaacugc | uagccgccag | cggcuugacc | cgcuguggc gcggcggcuu | 7740 |

-continued

```
gguuguuacu gagacagcgg uaaaaauagu caaauuucac aaccggaccu ucacccuagg    7800
accugugaau uuaaaagugg ccagugaggu ugagcuaaaa gacgcggucg agcauaacca    7860
acacccgguu gcaagaccgg uugauggugg uguugugcuc cugcgcuccg caguuccuuc    7920
gcuuauagac gucuuaaucu ccggcgcuga ugcaucuccc aaguuacucg cccgccacgg    7980
gccgggaaac acugggaucg auggcacgcu ugggauuuu gaggccgagg ccacuaaaga     8040
ggaaauugca cucagugcgc aaauaauaca ggcuugugac auuaggcgcg gcgacgcacc    8100
ugaaauuggu cuuccuuaua agcuguaccc ugucaggggc aacccugagc ggguaaaagg    8160
aguuuuacag aauacaaggu uuggagacau accuuauaaa accccagug acacuggaag     8220 cccagugcac gcggcugccu gccucacgcc caaugccacu ccggugacug augggcgcuc    8280
cgucuuggcc acgacuaugc ccuccgguuu ugaguuguau guaccgacca uccagcguc     8340 uguccuugau uaucuugauu cuaggccuga cugccccaaa caguugacag agcacggcug    8400
ugaggacgcc gcauuaagag accucuccaa guaugacuug uccacccaag gcuuuguuu    8460 accuggaguu cuucgccuug ugcguaagua ccuguuugcu caugugggua agugcccgcc    8520
cguucaucgg ccuccacuu acccugccaa gaauucuaug gcuggaauaa augggaacag    8580
guuuccaacc aaggacaucc agagcgucc ugaaaucgac guucugugcg cacaggccgu     8640
gcgggaaaac uggcaaacug uuaccccuug uacccucaag aaacaguauu ugggaagaa    8700 gaagacuagg acaauacucg gcaccaauaa cuucauugcg cuggccaccc gggcagcguu    8760 gaguggguc acccagggcu ucaugaaaaa ggcguuuaac ucgccauug cccucgguaa     8820 aaacaaauuu aaagagcuuc agacuccggu cuuaggcagg ugccuugaag cugaucuugc    8880
auccugcgau cgcuccacac cugcaauugu ccgcugguuu ccgcaaauc uucuuuauga    8940 acuugccugu gcugaagagc accugccguc guacguguug aacugcugcc acgaccuacu    9000
ggucacgcag uccggcgcag uaacuaagag aggugggccug ucgucuggcg acccgaucac    9060 uucuguguc aacaccauuu acagcuuggu gauauaugca caacacaugg ugcucaguua    9120
cuuuaaaagu ggucacccuc auggccuucu guuucuacaa gaccagcuga aguuugagga    9180
caugcucaag guucaaccc ugaucgucua uucggacgac cucguacugu augccgaguc    9240
ucccaccaug ccaaacuacc acuggugggu ugaacaucug aaccgaugc uggguuuuca    9300 gacggaccca aagaagacag ccauaacaga cucgccauca uuucuaggcu guaggauaau   9360
aaauggacgc cagcucgucc cuaaccguga caggauucuc gcggcccucg ccuaccauau    9420
gaaggcaagc aaugucucug aauacacgcg cucggcggcu gcgauacuca uggacagcug    9480
ugcuuguuua gaguaugauc ccgaaugguu ugaaagcuu guaguuggga uagcgcagug    9540
ugcccgcaag gacggcuaca guuucccgg cccgccguuc uucuuguca uguggaaaa    9600 acucagaucc aaucaugagg ggaagaaguc cagaaugugc ggguacgcg ggcccggc      9660 uccguacgcc acugccugug gccucgacgu cuguauuac cacacccacu uccaccagca    9720
uuguccaguc aucaucuggu guggccaccc ggcuggucu gguucuugua gugagugcaa    9780 accccccua gggaaggca caagcccucu agaugaggug uuagaacaag ucccguauaa     9840
gccuccacgg acuguaauca ugcauggga gcaggucuc acccucuug acccaggcag     9900 auaccagacu cgccgcggau uagucuccgu uaggcguggc auuagaggaa augagguga    9960 ucuaccagac ggugauuaug cuagcaccgc ccuacucccu acuuguaaag agauuaacau   10020
ggucgcuguc gccucuaaug uguugcgcag cagguucauc aucggcccgc cugguguggg   10080
gaaaacauac uggcuccuuc aacagguccca ggaugugau gucauuuaca cgccaacuca   10140
```

```
ccagaccaug cucgauauga uuagggcuuu ggggacgugc cgguucaacg ucccagcagg   10200
uacgacgcug caauucccug ccccucccg uaccggcccu uggguucgca uccuagccgg   10260
cgguuggugu ccuggcaaga auuccuuccu ggaugaagca gcguauugua aucaccuuga   10320
ugucuugagg cuucuuagca aaacuacccu caccugucug ggagauuuca acaacuccca   10380
cccagggggu uuugauucuc auugcuaugu uuugacauc augccucaga cucaacugaa   10440
gaccaucugg agauuuggac agaauaucug ugaugccauu cagccagauu acagggacaa   10500
acuugauucc augucaaca caacccgugu aaccacgug gaaaaaccug ucaaguaugg   10560
gcaaguccuc accccuuacc acagggaccg agaggacggc gccaucacaa uugacuccag   10620
ucaaggcgcc acauuugaug ugguuacacu gcauuugccc acuaaagauu cacucaacag   10680
gcaaagagcc cuuguugcua uuaccagggc aagacaugcu aucuuugugu augacccaca   10740
caggcaacug cagagcaugu uugaucuucc ugcgaaaggc acaccgcuca accucgcugu   10800
gcaccgugac gagcagcuga ucgugcuaga uagaaauaac aaagaaugca cgguugcuca   10860
ggcucuaggc aaugggauua aauucagggc cacagacaag cgcguuguag auucucuccg   10920
cgccauuugu gcagaucugg aagggucgag cuccccgcuc cccaaggucg cacacaacuu   10980
gggauuuuau uucucgccug auuugacaca guuugcuaaa cucccgguag aacuugcacc   11040
ccacuggccc gugugacaa cccagaacaa ugaaaagugg ccagaccggu ugguugcuag   11100
ccuucgcccc guccauaagu auagccgcgc gugcaucggu gccggcuaca uggugggccc   11160
cucagucuuu cugggcaccc cugggguugu gucauacuau ucacaaaaau uugucagggg   11220
cgaggcucaa augcuuccgg agacagucuu cagcaccggc cgaauugagg uagauugccg   11280
ugaguaucuu gaugaccggg agcgagaaau ugcugaugcc cuccccaug cuuucauugg   11340 cgacgucaaa ggcacuaccg uuggaggaug ucaccaugucc accuccaaau accuuccgcg   11400
cuuccuuccc aaggaaucag ucgcgguagu cggggggccgguguuca agccccggga aagccgcaaa   11460
agcaguuugc acauuaacag augguaucu cccagaucuc gaagcuuacc uccacccaga   11520
gacccagucc aagugcugga aaaugauguu ggacuucaag gaaguucgac ugauggucug   11580
gaaggacaag acggccuauu ucaacuuga aggccgccau ucaccuggu accagcuugc   11640 aagcuaugcc ucguacaucc gaguuccugu uaacucuacg guguauuugg accccugcau   11700
gggcccugcc cuuugcaaca aagagaguugu cgggccacu cauuggggag cugaccucgc   11760 agucacccu uaugauuacg gugccaaaau cauccugucu agugcauacc auggugaaau   11820
gccccugggg uacaaaaucc uggcgugcgc ggaguucucg cuugacgauc cagugaggua   11880
caaacacacc uggggguuug aaucggauac agcguaucug uacgaguuca ccggaaacgg   11940
ugaggacugg gaggauuaca augaugcguu ucgugcgcgc cagaaaggga aaauuuauaa   12000
ggccacugcc accagcauga gguuucauu uccccgggc ccugucauug aaccaacuuu   12060
aggccugaau ugaaaugaaa uggggcccau gcaaagccuc uuugacaaaa uuggccaacu   12120 uuuugguggau gcuuucacgg aauuuuuggu guccauuguu gauaucauca uauuuuggc   12180 cauuuuguuu ggccuuacca cgcuggcugc gcugguggcu uucugcaucc gauugguuug   12240 cuccgcgggua cuccgugcgc gcccuaccau ucacccugag caauuacaga agauccuaug   12300
aggccuuucu uucucagugc caggugguaua ucccaccug gggaacuaga caucccugg   12360 ggauguuuug gcaccauaag gugucaaccc ugauugauga aaugguguccg cgucggaugu   12420 accgcaccau ggaaaaagca ggacaggcug ccugaaaca gguggugagc gaggccacgc   12480
ugucucgcau uagugguuug gaugugggg cucauuuuca gcaucuugcc gccauugaag   12540
```

-continued

```
ccgagaccug uaaauauuug gccucucggc ugcccaugcu acacaaucug cgcaugacag   12600
ggucaaaugu aaccauagug uauaauagua cuuugaauca gguguuugcu auuuuccaa    12660 ccccuggauc ccggccaaag cuucaugauu ucagcaaug gcuaauagcu gugcacuccu    12720
ccauauuuuc cuccguugcg gcuucuugua cucuuuugu ugugcugugg uugcggauuc    12780
caauacuacg uacuguuuuu gguuccgcu gguuaggggc aauuuuuccu ucgaacucac    12840
ggugaauuac acgugugc cgccuugccu cacccggcaa gcagccgcug aggucuacga    12900
accaggcagg ucucuuuggu gcaggauagg gcaugaccga uguagugagg acgaccauga   12960
cgaucuaggg uucaugguuc cgccuggccu cuccagcgaa ggccacuuga ccaguguuua   13020
cgccugguug gcguuccugu ccuucagcua cacggcccag uuccaucccg agauauuugg   13080
gauagggaau gugagucaag uuuauguuga caucaagcac caauucaucu gcgccguuca   13140
cgacggggag aacgccaccu ugccucguca ugacaauauu ucagccguau uucagaccua   13200
cuaccaacau caagucgacg gcggcaauug guuucaccua gaauggcugc gccccuucuu   13260
uuccucuugg uugguuuuaa auguuucuug guuucucagg cgucgccug caagccaugu    13320 uucaguucaa gucuuucgga caucaaaacc aacacuaccg cagcaucagg cuuuguuguc   13380
cuccaggaca ucagcugccu uaggcauggc gacucguccu cucagacgau ucgcaaaagc   13440
ucucagugcc gcgcggcgau agggacgccc guguacauca cugucacagc caaugucaca   13500
gaugagaauu auuuacauuc uucugaucuc cuuaugcuuu cuucuugccu uucuaugcu    13560 ucugagauga gugaaaaggg auucaaggug auauuuggca augugucagg caucguggcu   13620 gugugugugca acuuuaccag cuacguccaa caugucaagg aguuuaccca acgcuccuug   13680
guggucgauc augugcggcu gcuccauuuc augacaccug agaccaugag gugggcaacc   13740
guuuuagccu guuuuuuugc caucuuacug gcaauuugaa uguucaagua uguggggag    13800 augcuugacc gcggcuguu gcgcgauu gcuucuuug ugguguaucg ugccauuug     13860 uuuugcugcg cucgucaacg ccaacagcaa cagcagcucu caucuucagu ugauuuacaa   13920
cuugacgcua ugugagcuga auggcacaga uuggcugaaa gacaaauuug auugggcagu   13980
ggagacuuuu gucaucuuuc ccguguugac ucacauuguc ucauaugug cacucaccac    14040 uagccauuuc cuugacacag ucggucuggu uacuguguc accgccgggu ucuaccacgg    14100
gcgguauguu cugaguagca cuacgcggu cugcgcucug gccgcauuga uuugcuucgu    14160
cauuaggcuu gcgaagaacu gcaugccug gcgcuacucu uguaccagau auacuaacuu    14220
ccuucuggac acuaagggca gacucuaucg cuggcggucg cccguuauca uagagaaagg   14280
ggguaagguu gaggucgaag gucaccgau cgaccucaaa agauugugc uugauguc     14340 cguggcaacc ccuuuaaccac gaguuucagc ggaacaaugg ggucgucuuu agacgacuuu   14400
ugcuaugaua gcacggcucc acaaaaggug cuuuuggcgu uuccauuac cuacacgcca    14460 gugaugauau augcucuaaa gguaagucgc ggccgacuuu uagggcuucu gcaccuuug    14520 aucuuuucuga auuguacuuu accuucgggu acaugacau ucgugcacuu uaauagcaca   14580
aauaaggucg cgcucacuau gggagcagua guugcacuuc uuuggggggu guacucagcc   14640
auagaaaccu ggaaguucau caccuccaga ugccguuugu gcuugcuagg ccgcaaguac   14700
auucggcccc ccgccaccaa cgucgaaagu gccgcggcuc uucauccgau cgcggcaaau   14760
gauaaccacg cauuugucgu ccggcgucc ggcuccacua cgguuaacgg cacauuggug    14820 cccgggguuga aagccucgu guuggguggc agaaaagcgu uuaaacaggg aguggauaaac   14880 cuugucaaau augccaaaua acaacggcaa gcagcaaaag aaaaaagggg ggaauggcca   14940
```

```
gccagucaau cagcugugcc agaugcuggg uaagaucauc gcccagcaaa accaguccag  15000
aggcaaggga ccggggaaga aaauuaagaa uaaaaacccg gagaagcccc auuuuccucu  15060
agcgacugaa gaugacguca ggcaucacuu caccccuagu gagcggcaau ugugucuguc  15120
gucgauccag acugccuuua accagggcgc uggaaccugu acccuaucag auucagguag  15180
gauaaguuac acuguggagu uuaguuugcc gacgcaucau acugugcgcc ugauccgcgu  15240
cacagcgcca ucaucagcgu aaugggcugg cauuccuuaa gcaccucagu guuagaauug  15300
gaagaaugug uggugaaugg cacugauugg cacugugccu cuaagucacc uauucaauua  15360
gggcgaccgu guggggguua aguuuaauug gcgagaacca ugcggccgaa auu         15413
```